(12) United States Patent
Maffitt et al.

(10) Patent No.: US 6,998,260 B1
(45) Date of Patent: Feb. 14, 2006

(54) RECOMBINANT PROTEOLYTIC TRYPTASES, ACTIVE SITE MUTANTS THEREOF, AND METHODS OF MAKING SAME

(75) Inventors: Mark Maffitt, Madison, WI (US); Andrew L. Niles, Madison, WI (US); Mary Haak-Frendscho, Newark, CA (US)

(73) Assignee: Promega Corporation, Madison, WI (US)

( * ) Notice: Subject to any disclaimer, the term of this patent is extended or adjusted under 35 U.S.C. 154(b) by 707 days.

(21) Appl. No.: 09/598,982

(22) Filed: Jun. 21, 2000

Related U.S. Application Data

(63) Continuation-in-part of application No. 09/079,970, filed on Apr. 15, 1998, now Pat. No. 6,274,366.

(51) Int. Cl.
  C12N 9/64   (2006.01)
  C12N 5/00   (2006.01)
  C12N 15/00  (2006.01)
  C12N 1/14   (2006.01)
  C12P 21/06  (2006.01)

(52) U.S. Cl. .................... 435/226; 435/325; 435/320.1; 435/23; 435/69.1; 435/219; 435/252.3; 435/254.1; 435/254.2; 435/254.23; 536/23.2; 530/350

(58) Field of Classification Search ................. 435/23, 435/69.1, 219, 325, 252.3, 254.1, 254.2, 435/254.23, 226, 320.1; 536/23.2; 530/350
See application file for complete search history.

(56) References Cited

OTHER PUBLICATIONS

Bork , Genome Research, 10:398-400, 2000.*
Broun et al. , Science 282:1315-1317, 1998.*
Seffernick et al. , J. Bacteriol. 183(8):2405-2410, 2001.*
Van de Loo et al. , Proc. Natl. Acad. Sci. 92:6743-6747, 1995.*
Blom, T. and Hellman, L. (1993), *Scand. J. Immunol.* 37:203-208.
Buckholz, R.G. and Gleeson, M.A.G. (1991), *Biotechnology* 9:1067-1072.
Chan, H.; Elrod, K.C.; Numerof, R.P. Sideris, S; and Clark, J.M. (1999), *Protein Express. & Purif.* 15:251-257.
Clark J.M.; Abraham, W.M.; Fishman, C.E.; Foreza, R. Ahmed, A.; Cortes, A.; Warne, R.L.; Moore, W.R; and Tanaka, R.D. (1995), *Am. J. Respir. Crit. Care Med.* 152: 2076-2083.
Holgate S.T. and Church, M.K. (1992), *Br. Med. Bull UK* 48:40-50.
Faber K.N.; Harder, W.; Ab, G.; and Veenhuis, M. (1995), *Yeast* 11:1331-1344.
Harvima, I.T.; Schechter N.M.; Harvima, R.J.; and Fräki, J.E. (1988) Human Skin Tryptase: Purification, Partial Characterization and Comparison with Human Lung Tryptase, *Biochimimica et Biophysica Acta*, 957:71-80.
Huang, C.; Li, L.; Krilis, S.A.; Chanasyk, K.; Tang, Y.; Li, Z.; Hunt, J.E.; and Stevens, R.L. (1999) Human Tryptase α and β/II are Functionally Distrinct Due, in Part, to a Single Amino Acid Difference in One of the Surface Loops that Forms the Substrate-binding Cleft, *J. Biol. Chem.* 274: 19670-19676.
Huang, C.; Guillermo, M.; Vagi, A.; Chanasyk, K.; Ferrazzi, M.; Burklow, C.; Qiu, W.; Feyfant, E.; Sali, A.; and Stevens, R.L. , (2000) Formation of Enzymatically Active, Homotypic, and Heterotypic Tetramers of Mouse Mast Cell Tryptases, *J. Biol. Chem.* 275:351-358.
Ide, H.; Itoh, H.; Tomita, M.; Murakumo, Y.; Kobayashi, T.; Maruyama, H.; Osada, Y.; and Nawa, Y. (1995), *J. Biochem.* 118:210-215.
Miller, J.S.; Moxley, G.; and Schwartz, L.B. (1990), *J. Clin. Invest.* 86:864-870.
Niles, A.L.; Maffitt, M.; Haak-Frendscho, M.; Wheeless, C.J.; and Johnson, D.A. (1998), Recombinant Human Mast Cell Tryptase: Stable Expression in *Pichia pastoris* and Purification of Fully Active Enzyme, *Biotechnol. Appl. Biochem.* 28:125-131.
Nilsson and Schwartz (1994), Mast-Cell Heterogeneity: Structure and Mediators, Blackwell Scientific Publications, Boston, pp. 195-208.
Pallaoro, M.; Fejzo, M.S.; Shayesteh, L; Blount, J.L.; and Caughey, G.H. (1999), Characterization of Genes Encoding Known and Novel Human Mast Cell Tryptases on Chromosome 16p13.3, *J. Biol. Chem.* 6:3355-3362.
Sakai K.; Long, S.D.; Dove-Pettit, D.A.; Cabral, G.A.; and Schwartz, L.B. (1996), *Protein Express. & Purif.* 7:67-73.
Sambrook, J.; Fritsch, E. F.; and Maniatis, T. (1989), *Molecular Cloning: A Laboratory Manual*; Cold Spring Harbor Laboratory Press: New York, NY.

(Continued)

*Primary Examiner*—Rebecca E. Prouty
*Assistant Examiner*—Delia M. Ramirez
(74) *Attorney, Agent, or Firm*—Joseph T. Leone, Esq.; DeWitt Ross & Stevens S.C.

(57) ABSTRACT

Disclosed is a method of expressing enzymatically-active, recombinant proteolytic tryptase in a eukaryotic host cell, expression constructs which drive the production of enzymatically-active tryptase in transformed hosts, and genetically-engineered eukaryotic host cells containing the expression constructs and which express enzymatically-active proteolytic tryptases. Uses for the proteolytic tryptases so produced are also disclosed. Also disclosed is a method of making active site mutants of proteolytic tryptases in a eukaryotic host cell, expression constructs which drive the production of the mutants in transformed eukaryotic host cells, and genetically-engineered eukaryotic host cells containing the expression constructs and which express the active-site mutated form of proteolytic tryptases.

30 Claims, 9 Drawing Sheets

OTHER PUBLICATIONS

Schwartz L.B.; Bradford, T.R.; Littman, B.H.; and Wintroub, B.U. (1985), *J. Immun.* 135:2762-2767.

Schwartz L and Bradford T. (1986) Regulation of tryptase from human lung mast cells by heparin: Stabilization of the active tetramer, *J. Biol. Chem.* 256: 7372-7379.

Schwartz (1995), Structure and Function of Human Mast Cell Tryptase, *Biological and Molecular Aspects of Mast Cell and Basophil Differentiation and Function*, chapter 14:161-173, Raven Press, Ltd: New York.

Scopes, R. K., (1994), Protein Purification, Principles and Practices, Springer-Verlag: New York.

Smith, T.J.; Houghland, M.W.; and Johnson, D.A. (1984), *J. Biol. Chem.* 259(17):11045-11051.

Sommerhoff, C.P.; Bode, W.; Pereira, P.J.B.; Stubbs, M.T.; Stürzebecher, J.; Piechottka, G.P.; Matschiner, G.; and Bergner, A. (1999), "The Structure of the Human βII-tryptase Tetramer: Fo(u)r Better of Worse," *Proc. Natl. Acad. Sci. USA* 96:10984-10991.

Vanderslice P.; Ballinger, S.M.; Tam, E.K.; Goldstein, S.M.; Craik, C.S.; and Caughey, G. H. (1990), *Biochemistry* 87: 3811-3815.

Wung, J.L. and Gascoigne, R.J. (1996), *BioTechniques* 21: 812-816.

\* cited by examiner

```
Tryptase α    MLSLLLLALP VLASRAYAAP APVQALQQAG IVGGQEAPRS KWPWQVSLRV RDRYWMHFCG    (30)
Tryptase β-I  --N-------  ---------  --G----RV- ---------- ---------- ---HGP-----
Tryptase β-II --N-------  ---------  --G----RV- ---------- ---------- ---HGP-----
                                                                           ▲
                                                                           A Tryptase α    GSLIHPQWVL TAAHCLGPDV KDLATLRVQL REQHLYYQDQ LLPVSRIIVH PQFYIIQTGA    (90)
Tryptase β-I  ---------- -----V----  ----A----  ---------- ---------- ----TA-I--
Tryptase β-II ---------- -----V----  ----A----  ---------- ---------- ----TA-I--
                              B                                              C Tryptase α    DIALLELEEP VNISSRVHTV MLPPASETFP PGMPCWVTGW GDVDNDEPLP PPFPLKQVKV    (150)
Tryptase β-I  ---V--H--- ----T----- ---------- ---------- ------R--- ----------
Tryptase β-II -KV--H--- ----T----- ---------- ---------- ------R--- ----------
                         D Tryptase α    PIMENHICDA KYHLGAYTGD DVRIIRDDML CAGNSQRDSC KGDSGGPLVC KVNGTWLQAG    (210)
Tryptase β-I  ---------- ---------- ----V----- ----TR---- ----Q----- ----------
Tryptase β-II ---------- ---------- ----V----- ----TR---- ----Q----- ----------
                                                            1

Tryptase α    VVSWDEGCAQ PNRPGIYTRV TYYLDWIHHY VPKKP (SEQ. ID. NO: 52)
Tryptase β-I  ----G----- ---------- ---------- -----
Tryptase β-II ----G----- ---------- ---------- -----
                2                3
```

FIG. 1

SEQUENCE LISTING

<160> NUMBER OF SEQ ID NOS: 52

<210> SEQ ID NO 1
<211> LENGTH: 735
<212> TYPE: DNA
<213> ORGANISM: Homo sapiens
<220> FEATURE:
<221> NAME/KEY: CDS
<222> LOCATION: (1)..(735)

<400> SEQUENCE: 1

```
atc gtc ggg ggt cag gag gcc ccc agg agc aag tgg ccc tgg cag gtg        48
Ile Val Gly Gly Gln Glu Ala Pro Arg Ser Lys Trp Pro Trp Gln Val
1               5                   10                  15 agc ctg aga gtc cac ggc cca tac tgg atg cac ttc tgc ggg ggc tcc        96
Ser Leu Arg Val His Gly Pro Tyr Trp Met His Phe Cys Gly Gly Ser
                20                  25                  30 ctc atc cac ccc cag tgg gtg ctg acc gca gcg cac tgc gtg gga ccg       144
Leu Ile His Pro Gln Trp Val Leu Thr Ala Ala His Cys Val Gly Pro
            35                  40                  45 gac gtc aag gat ctg gcc gcc ctc agg gtg caa ctg cgg gag cag cac       192
Asp Val Lys Asp Leu Ala Ala Leu Arg Val Gln Leu Arg Glu Gln His
        50                  55                  60 ctc tac tac cag gac cag ctg ctg ccg gtc agc agg atc atc gtg cac       240
Leu Tyr Tyr Gln Asp Gln Leu Leu Pro Val Ser Arg Ile Ile Val His
65                  70                  75                  80 cca cag ttc tac acc gcc cag atc gga gcg gac atc gcc ctg ctg gag       288
Pro Gln Phe Tyr Thr Ala Gln Ile Gly Ala Asp Ile Ala Leu Leu Glu
                85                  90                  95 ctg gag gag ccg gtg aac gtc tcc agc cac gtc cac acg gtc acc ctg       336
Leu Glu Glu Pro Val Asn Val Ser Ser His Val His Thr Val Thr Leu
                100                 105                 110 ccc cct gcc tca gag acc ttc ccc ccg ggg atg ccg tgc tgg gtc act       384
Pro Pro Ala Ser Glu Thr Phe Pro Pro Gly Met Pro Cys Trp Val Thr
            115                 120                 125 ggc tgg ggc gat gtg gac aat gat gag cgc ctc cca ccg cca ttt cct       432
Gly Trp Gly Asp Val Asp Asn Asp Glu Arg Leu Pro Pro Pro Phe Pro
        130                 135                 140 ctg aag cag gtg aag gtc ccc ata atg gaa aac cac att tgt gac gca       480
Leu Lys Gln Val Lys Val Pro Ile Met Glu Asn His Ile Cys Asp Ala
145                 150                 155                 160 aaa tac cac ctt ggc gcc tac acg gga gac gac gtc cgc atc gtc cgt       528
Lys Tyr His Leu Gly Ala Tyr Thr Gly Asp Asp Val Arg Ile Val Arg
                165                 170                 175 gac gac atg ctg tgt gcc ggg aac acc cgg agg gac tca tgc cag ggc       576
```

-continued

| | | | | | | | | | | | | |
|---|---|---|---|---|---|---|---|---|---|---|---|---|
| Asp | Asp | Met | Leu | Cys | Ala | Gly | Asn | Thr | Arg | Arg | Asp | Ser | Cys | Gln | Gly |
| | | | 180 | | | | | 185 | | | | 190 | | | |

```
gac tcc gga ggg ccc ctg gtg tgc aag gtg aat ggc acc tgg ctg cag      624
Asp Ser Gly Gly Pro Leu Val Cys Lys Val Asn Gly Thr Trp Leu Gln
        195                 200                 205 gcg ggc gtg gtc agc tgg ggc gag ggc tgt gcc cag ccc aac cgg cct      672
Ala Gly Val Val Ser Trp Gly Glu Gly Cys Ala Gln Pro Asn Arg Pro
210                 215                 220 ggc atc tac acc cgt gtc acc tac tac ttg gac tgg atc cac cac tat      720
Gly Ile Tyr Thr Arg Val Thr Tyr Tyr Leu Asp Trp Ile His His Tyr
225                 230                 235                 240 gtc ccc aaa aag ccg                                                  735
Val Pro Lys Lys Pro
                245

<210> SEQ ID NO 2
<211> LENGTH: 245
<212> TYPE: PRT
<213> ORGANISM: Homo sapiens

<400> SEQUENCE: 2

Ile Val Gly Gly Gln Glu Ala Pro Arg Ser Lys Trp Pro Trp Gln Val
1               5                   10                  15

Ser Leu Arg Val His Gly Pro Tyr Trp Met His Phe Cys Gly Gly Ser
                20                  25                  30

Leu Ile His Pro Gln Trp Val Leu Thr Ala Ala His Cys Val Gly Pro
            35                  40                  45

Asp Val Lys Asp Leu Ala Ala Leu Arg Val Gln Leu Arg Glu Gln His
        50                  55                  60

Leu Tyr Tyr Gln Asp Gln Leu Leu Pro Val Ser Arg Ile Ile Val His
65                  70                  75                  80

Pro Gln Phe Tyr Thr Ala Gln Ile Gly Ala Asp Ile Ala Leu Leu Glu
                85                  90                  95

Leu Glu Glu Pro Val Asn Val Ser Ser His Val His Thr Val Thr Leu
            100                 105                 110

Pro Pro Ala Ser Glu Thr Phe Pro Pro Gly Met Pro Cys Trp Val Thr
        115                 120                 125

Gly Trp Gly Asp Val Asp Asn Asp Glu Arg Leu Pro Pro Pro Phe Pro
130                 135                 140

Leu Lys Gln Val Lys Val Pro Ile Met Glu Asn His Ile Cys Asp Ala
145                 150                 155                 160

Lys Tyr His Leu Gly Ala Tyr Thr Gly Asp Asp Val Arg Ile Val Arg
                165                 170                 175

Asp Asp Met Leu Cys Ala Gly Asn Thr Arg Arg Asp Ser Cys Gln Gly
            180                 185                 190

Asp Ser Gly Gly Pro Leu Val Cys Lys Val Asn Gly Thr Trp Leu Gln
        195                 200                 205

Ala Gly Val Val Ser Trp Gly Glu Gly Cys Ala Gln Pro Asn Arg Pro
210                 215                 220

Gly Ile Tyr Thr Arg Val Thr Tyr Tyr Leu Asp Trp Ile His His Tyr
225                 230                 235                 240

Val Pro Lys Lys Pro
                245

<210> SEQ ID NO 3
<211> LENGTH: 40
<212> TYPE: DNA
```

```
<213> ORGANISM: Artificial Sequence
<220> FEATURE:
<223> OTHER INFORMATION: PCR primer

<400> SEQUENCE: 3
gggcccctcg agaaaagaat cgtcgggggt caggaggccc                           40

<210> SEQ ID NO 4
<211> LENGTH: 40
<212> TYPE: DNA
<213> ORGANISM: Artificial Sequence
<220> FEATURE:
<223> OTHER INFORMATION: PCR primer

<400> SEQUENCE: 4
ccactatgtc cccaaaaagc cgtgaagcgg ccgccgtcgt                           40

<210> SEQ ID NO 5
<211> LENGTH: 771
<212> TYPE: DNA
<213> ORGANISM: Homo sapiens
<220> FEATURE:
<221> NAME/KEY: CDS
<222> LOCATION: (7)..(753)

<400> SEQUENCE: 5 gggccc ctc gag aaa aga atc gtc ggg ggt cag gag gcc ccc agg agc       48
       Leu Glu Lys Arg Ile Val Gly Gly Gln Glu Ala Pro Arg Ser
         1               5                  10 aag tgg ccc tgg cag gtg agc ctg aga gtc cac ggc cca tac tgg atg      96
Lys Trp Pro Trp Gln Val Ser Leu Arg Val His Gly Pro Tyr Trp Met
 15                  20                  25                  30 cac ttc tgc ggg ggc tcc ctc atc cac ccc cag tgg gtg ctg acc gca     144
His Phe Cys Gly Gly Ser Leu Ile His Pro Gln Trp Val Leu Thr Ala
                 35                  40                  45 gcg cac tgc gtg gga ccg gac gtc aag gat ctg gcc gcc ctc agg gtg     192
Ala His Cys Val Gly Pro Asp Val Lys Asp Leu Ala Ala Leu Arg Val
             50                  55                  60 caa ctg cgg gag cag cac ctc tac tac cag gac cag ctg ctg ccg gtc     240
Gln Leu Arg Glu Gln His Leu Tyr Tyr Gln Asp Gln Leu Leu Pro Val
         65                  70                  75 agc agg atc atc gtg cac cca cag ttc tac acc gcc cag atc gga gcg     288
Ser Arg Ile Ile Val His Pro Gln Phe Tyr Thr Ala Gln Ile Gly Ala
     80                  85                  90 gac atc gcc ctg ctg gag ctg gag gag ccg gtg aac gtc tcc agc cac     336
Asp Ile Ala Leu Leu Glu Leu Glu Glu Pro Val Asn Val Ser Ser His
 95                 100                 105                 110 gtc cac acg gtc acc ctg ccc cct gcc tca gag acc ttc ccc ccg ggg     384
Val His Thr Val Thr Leu Pro Pro Ala Ser Glu Thr Phe Pro Pro Gly
                115                 120                 125 atg ccg tgc tgg gtc act ggc tgg ggc gat gtg gac aat gat gag cgc     432
Met Pro Cys Trp Val Thr Gly Trp Gly Asp Val Asp Asn Asp Glu Arg
            130                 135                 140 ctc cca ccg cca ttt cct ctg aag cag gtg aag gtc ccc ata atg gaa     480
Leu Pro Pro Pro Phe Pro Leu Lys Gln Val Lys Val Pro Ile Met Glu
        145                 150                 155 aac cac att tgt gac gca aaa tac cac ctt ggc gcc tac acg gga gac     528
Asn His Ile Cys Asp Ala Lys Tyr His Leu Gly Ala Tyr Thr Gly Asp
    160                 165                 170 gac gtc cgc atc gtc cgt gac gac atg ctg tgt gcc ggg aac acc cgg     576
Asp Val Arg Ile Val Arg Asp Asp Met Leu Cys Ala Gly Asn Thr Arg
175                 180                 185                 190
```

```
agg gac tca tgc cag ggc gac tcc gga ggg ccc ctg gtg tgc aag gtg      624
Arg Asp Ser Cys Gln Gly Asp Ser Gly Gly Pro Leu Val Cys Lys Val
            195                 200                 205 aat ggc acc tgg ctg cag gcg ggc gtg gtc agc tgg ggc gag ggc tgt      672
Asn Gly Thr Trp Leu Gln Ala Gly Val Val Ser Trp Gly Glu Gly Cys
        210                 215                 220 gcc cag ccc aac cgg cct ggc atc tac acc cgt gtc acc tac tac ttg      720
Ala Gln Pro Asn Arg Pro Gly Ile Tyr Thr Arg Val Thr Tyr Tyr Leu
    225                 230                 235 gac tgg atc cac cac tat gtc ccc aaa aag ccg tgaagcggcc gccgtcgt      771
Asp Trp Ile His His Tyr Val Pro Lys Lys Pro
240                 245

<210> SEQ ID NO 6
<211> LENGTH: 249
<212> TYPE: PRT
<213> ORGANISM: Homo sapiens

<400> SEQUENCE: 6

Leu Glu Lys Arg Ile Val Gly Gly Gln Glu Ala Pro Arg Ser Lys Trp
1               5                   10                  15

Pro Trp Gln Val Ser Leu Arg Val His Gly Pro Tyr Trp Met His Phe
            20                  25                  30

Cys Gly Gly Ser Leu Ile His Pro Gln Trp Val Leu Thr Ala Ala His
        35                  40                  45

Cys Val Gly Pro Asp Val Lys Asp Leu Ala Ala Leu Arg Val Gln Leu
    50                  55                  60

Arg Glu Gln His Leu Tyr Tyr Gln Asp Gln Leu Leu Pro Val Ser Arg
65                  70                  75                  80

Ile Ile Val His Pro Gln Phe Tyr Thr Ala Gln Ile Gly Ala Asp Ile
                85                  90                  95

Ala Leu Leu Glu Leu Glu Glu Pro Val Asn Val Ser Ser His Val His
            100                 105                 110

Thr Val Thr Leu Pro Pro Ala Ser Glu Thr Phe Pro Pro Gly Met Pro
        115                 120                 125

Cys Trp Val Thr Gly Trp Gly Asp Val Asp Asn Asp Glu Arg Leu Pro
    130                 135                 140

Pro Pro Phe Pro Leu Lys Gln Val Lys Val Pro Ile Met Glu Asn His
145                 150                 155                 160

Ile Cys Asp Ala Lys Tyr His Leu Gly Ala Tyr Thr Gly Asp Asp Val
                165                 170                 175

Arg Ile Val Arg Asp Asp Met Leu Cys Ala Gly Asn Thr Arg Arg Asp
            180                 185                 190

Ser Cys Gln Gly Asp Ser Gly Gly Pro Leu Val Cys Lys Val Asn Gly
        195                 200                 205

Thr Trp Leu Gln Ala Gly Val Val Ser Trp Gly Glu Gly Cys Ala Gln
    210                 215                 220

Pro Asn Arg Pro Gly Ile Tyr Thr Arg Val Thr Tyr Tyr Leu Asp Trp
225                 230                 235                 240

Ile His His Tyr Val Pro Lys Lys Pro
                245

<210> SEQ ID NO 7
<211> LENGTH: 27
<212> TYPE: DNA
<213> ORGANISM: Artificial Sequence
<220> FEATURE:
<223> OTHER INFORMATION: Mutagenesis oligonucleotide
```

<400> SEQUENCE: 7
gaggagccgg tgaaggtctc cagccac                                27

<210> SEQ ID NO 8
<211> LENGTH: 771
<212> TYPE: DNA
<213> ORGANISM: Homo sapiens
<220> FEATURE:
<221> NAME/KEY: CDS
<222> LOCATION: (7)..(753)

<400> SEQUENCE: 8

```
gggccc ctc gag aaa aga atc gtc ggg ggt cag gag gcc ccc agg agc       48
       Leu Glu Lys Arg Ile Val Gly Gly Gln Glu Ala Pro Arg Ser
       1               5                  10 aag tgg ccc tgg cag gtg agc ctg aga gtc cac ggc cca tac tgg atg     96
Lys Trp Pro Trp Gln Val Ser Leu Arg Val His Gly Pro Tyr Trp Met
15              20                  25                  30 cac ttc tgc ggg ggc tcc ctc atc cac ccc cag tgg gtg ctg acc gca    144
His Phe Cys Gly Gly Ser Leu Ile His Pro Gln Trp Val Leu Thr Ala
                35                  40                  45 gcg cac tgc gtg gga ccg gac gtc aag gat ctg gcc gcc ctc agg gtg    192
Ala His Cys Val Gly Pro Asp Val Lys Asp Leu Ala Ala Leu Arg Val
            50                  55                  60 caa ctg cgg gag cag cac ctc tac tac cag gac cag ctg ctg ccg gtc    240
Gln Leu Arg Glu Gln His Leu Tyr Tyr Gln Asp Gln Leu Leu Pro Val
        65                  70                  75 agc agg atc atc gtg cac cca cag ttc tac acc gcc cag atc gga gcg    288
Ser Arg Ile Ile Val His Pro Gln Phe Tyr Thr Ala Gln Ile Gly Ala
    80                  85                  90 gac atc gcc ctg ctg gag ctg gag gag ccg gtg aag gtc tcc agc cac    336
Asp Ile Ala Leu Leu Glu Leu Glu Glu Pro Val Lys Val Ser Ser His
95                  100                 105                 110 gtc cac acg gtc acc ctg ccc cct gcc tca gag acc ttc ccc ccg ggg    384
Val His Thr Val Thr Leu Pro Pro Ala Ser Glu Thr Phe Pro Pro Gly
                115                 120                 125 atg ccg tgc tgg gtc act ggc tgg ggc gat gtg gac aat gat gag cgc    432
Met Pro Cys Trp Val Thr Gly Trp Gly Asp Val Asp Asn Asp Glu Arg
            130                 135                 140 ctc cca ccg cca ttt cct ctg aag cag gtg aag gtc ccc ata atg gaa    480
Leu Pro Pro Pro Phe Pro Leu Lys Gln Val Lys Val Pro Ile Met Glu
        145                 150                 155 aac cac att tgt gac gca aaa tac cac ctt ggc gcc tac acg gga gac    528
Asn His Ile Cys Asp Ala Lys Tyr His Leu Gly Ala Tyr Thr Gly Asp
    160                 165                 170 gac gtc cgc atc gtc cgt gac gac atg ctg tgt gcc ggg aac acc cgg    576
Asp Val Arg Ile Val Arg Asp Asp Met Leu Cys Ala Gly Asn Thr Arg
175                 180                 185                 190 agg gac tca tgc cag ggc gac tcc gga ggg ccc ctg gtg tgc aag gtg    624
Arg Asp Ser Cys Gln Gly Asp Ser Gly Gly Pro Leu Val Cys Lys Val
                195                 200                 205 aat ggc acc tgg ctg cag gcg ggc gtg gtc agc tgg ggc gag ggc tgt    672
Asn Gly Thr Trp Leu Gln Ala Gly Val Val Ser Trp Gly Glu Gly Cys
            210                 215                 220 gcc cag ccc aac cgg cct ggc atc tac acc cgt gtc acc tac tac ttg    720
Ala Gln Pro Asn Arg Pro Gly Ile Tyr Thr Arg Val Thr Tyr Tyr Leu
        225                 230                 235 gac tgg atc cac cac tat gtc ccc aaa aag ccg tgaagcggcc gccgtcgt    771
Asp Trp Ile His His Tyr Val Pro Lys Lys Pro
    240                 245
```

-continued

<210> SEQ ID NO 9
<211> LENGTH: 249
<212> TYPE: PRT
<213> ORGANISM: Homo sapiens

<400> SEQUENCE: 9

```
Leu Glu Lys Arg Ile Val Gly Gly Gln Glu Ala Pro Arg Ser Lys Trp
1               5                   10                  15

Pro Trp Gln Val Ser Leu Arg Val His Gly Pro Tyr Trp Met His Phe
            20                  25                  30

Cys Gly Gly Ser Leu Ile His Pro Gln Trp Val Leu Thr Ala Ala His
        35                  40                  45

Cys Val Gly Pro Asp Val Lys Asp Leu Ala Ala Leu Arg Val Gln Leu
    50                  55                  60

Arg Glu Gln His Leu Tyr Tyr Gln Asp Gln Leu Leu Pro Val Ser Arg
65                  70                  75                  80

Ile Ile Val His Pro Gln Phe Tyr Thr Ala Gln Ile Gly Ala Asp Ile
                85                  90                  95

Ala Leu Leu Glu Leu Glu Glu Pro Val Lys Val Ser Ser His Val His
            100                 105                 110

Thr Val Thr Leu Pro Pro Ala Ser Glu Thr Phe Pro Pro Gly Met Pro
        115                 120                 125

Cys Trp Val Thr Gly Trp Gly Asp Val Asp Asn Asp Glu Arg Leu Pro
    130                 135                 140

Pro Pro Phe Pro Leu Lys Gln Val Lys Val Pro Ile Met Glu Asn His
145                 150                 155                 160

Ile Cys Asp Ala Lys Tyr His Leu Gly Ala Tyr Thr Gly Asp Asp Val
                165                 170                 175

Arg Ile Val Arg Asp Asp Met Leu Cys Ala Gly Asn Thr Arg Arg Asp
            180                 185                 190

Ser Cys Gln Gly Asp Ser Gly Gly Pro Leu Val Cys Lys Val Asn Gly
        195                 200                 205

Thr Trp Leu Gln Ala Gly Val Val Ser Trp Gly Glu Gly Cys Ala Gln
    210                 215                 220

Pro Asn Arg Pro Gly Ile Tyr Thr Arg Val Thr Tyr Tyr Leu Asp Trp
225                 230                 235                 240

Ile His His Tyr Val Pro Lys Lys Pro
                245
```

<210> SEQ ID NO 10
<211> LENGTH: 735
<212> TYPE: DNA
<213> ORGANISM: Homo sapiens
<220> FEATURE:
<221> NAME/KEY: CDS
<222> LOCATION: (1)..(735)

<400> SEQUENCE: 10

```
atc gtc ggg ggt cag gag gcc ccc agg agc aag tgg ccc tgg cag gtg     48
Ile Val Gly Gly Gln Glu Ala Pro Arg Ser Lys Trp Pro Trp Gln Val
1               5                   10                  15 agc ctg aga gtc cac ggc cca tac tgg atg cac ttc tgc ggg ggc tcc     96
Ser Leu Arg Val His Gly Pro Tyr Trp Met His Phe Cys Gly Gly Ser
            20                  25                  30 ctc atc cac ccc cag tgg gtg ctg acc gca gcg cac tgc gtg gga ccg    144
Leu Ile His Pro Gln Trp Val Leu Thr Ala Ala His Cys Val Gly Pro
        35                  40                  45
```

-continued

| | | |
|---|---|---|
| gac gtc aag gat ctg gcc gcc ctc agg gtg caa ctg cgg gag cag cac<br>Asp Val Lys Asp Leu Ala Ala Leu Arg Val Gln Leu Arg Glu Gln His<br>     50                     55                 60 | | 192 |
| ctc tac tac cag gac cag ctg ctg ccg gtc agc agg atc atc gtg cac<br>Leu Tyr Tyr Gln Asp Gln Leu Leu Pro Val Ser Arg Ile Ile Val His<br>65                     70                    75                   80 | | 240 |
| cca cag ttc tac acc gcc cag atc gga gcg gac atc gcc ctg ctg gag<br>Pro Gln Phe Tyr Thr Ala Gln Ile Gly Ala Asp Ile Ala Leu Leu Glu<br>                 85                     90                     95 | | 288 |
| ctg gag gag ccg gtg aag gtc tcc agc cac gtc cac acg gtc acc ctg<br>Leu Glu Glu Pro Val Lys Val Ser Ser His Val His Thr Val Thr Leu<br>               100                    105                 110 | | 336 |
| ccc cct gcc tca gag acc ttc ccc ccg ggg atg ccg tgc tgg gtc act<br>Pro Pro Ala Ser Glu Thr Phe Pro Pro Gly Met Pro Cys Trp Val Thr<br>     115                     120                    125 | | 384 |
| ggc tgg ggc gat gtg gac aat gat gag cgc ctc cca ccg cca ttt cct<br>Gly Trp Gly Asp Val Asp Asn Asp Glu Arg Leu Pro Pro Pro Phe Pro<br>130                   135                    140 | | 432 |
| ctg aag cag gtg aag gtc ccc ata atg gaa aac cac att tgt gac gca<br>Leu Lys Gln Val Lys Val Pro Ile Met Glu Asn His Ile Cys Asp Ala<br>145                   150                    155                 160 | | 480 |
| aaa tac cac ctt ggc gcc tac acg gga gac gac gtc cgc atc gtc cgt<br>Lys Tyr His Leu Gly Ala Tyr Thr Gly Asp Asp Val Arg Ile Val Arg<br>               165                    170                 175 | | 528 |
| gac gac atg ctg tgt gcc ggg aac acc cgg agg gac tca tgc cag ggc<br>Asp Asp Met Leu Cys Ala Gly Asn Thr Arg Arg Asp Ser Cys Gln Gly<br>               180                    185                 190 | | 576 |
| gac tcc gga ggg ccc ctg gtg tgc aag gtg aat ggc acc tgg ctg cag<br>Asp Ser Gly Gly Pro Leu Val Cys Lys Val Asn Gly Thr Trp Leu Gln<br>     195                     200                    205 | | 624 |
| gcg ggc gtg gtc agc tgg ggc gag ggc tgt gcc cag ccc aac cgg cct<br>Ala Gly Val Val Ser Trp Gly Glu Gly Cys Ala Gln Pro Asn Arg Pro<br>210                   215                    220 | | 672 |
| ggc atc tac acc cgt gtc acc tac tac ttg gac tgg atc cac cac tat<br>Gly Ile Tyr Thr Arg Val Thr Tyr Tyr Leu Asp Trp Ile His His Tyr<br>225                   230                    235                 240 | | 720 |
| gtc ccc aaa aag ccg<br>Val Pro Lys Lys Pro<br>               245 | | 735 |

<210> SEQ ID NO 11
<211> LENGTH: 245
<212> TYPE: PRT
<213> ORGANISM: Homo sapiens

<400> SEQUENCE: 11

Ile Val Gly Gly Gln Glu Ala Pro Arg Ser Lys Trp Pro Trp Gln Val
1                        5                         10                       15

Ser Leu Arg Val His Gly Pro Tyr Trp Met His Phe Cys Gly Gly Ser
               20                    25                    30

Leu Ile His Pro Gln Trp Val Leu Thr Ala Ala His Cys Val Gly Pro
               35                    40                    45

Asp Val Lys Asp Leu Ala Ala Leu Arg Val Gln Leu Arg Glu Gln His
     50                     55                    60

Leu Tyr Tyr Gln Asp Gln Leu Leu Pro Val Ser Arg Ile Ile Val His
65                     70                    75                   80

Pro Gln Phe Tyr Thr Ala Gln Ile Gly Ala Asp Ile Ala Leu Leu Glu
               85                    90                    95

Leu Glu Glu Pro Val Lys Val Ser Ser His Val His Thr Val Thr Leu
             100                 105                 110

Pro Pro Ala Ser Glu Thr Phe Pro Pro Gly Met Pro Cys Trp Val Thr
             115                 120                 125

Gly Trp Gly Asp Val Asp Asn Asp Glu Arg Leu Pro Pro Phe Pro
         130                 135                 140

Leu Lys Gln Val Lys Val Pro Ile Met Glu Asn His Ile Cys Asp Ala
145                 150                 155                 160

Lys Tyr His Leu Gly Ala Tyr Thr Gly Asp Asp Val Arg Ile Val Arg
                 165                 170                 175

Asp Asp Met Leu Cys Ala Gly Asn Thr Arg Arg Asp Ser Cys Gln Gly
             180                 185                 190

Asp Ser Gly Gly Pro Leu Val Cys Lys Val Asn Gly Thr Trp Leu Gln
             195                 200                 205

Ala Gly Val Val Ser Trp Gly Glu Gly Cys Ala Gln Pro Asn Arg Pro
         210                 215                 220

Gly Ile Tyr Thr Arg Val Thr Tyr Tyr Leu Asp Trp Ile His His Tyr
225                 230                 235                 240

Val Pro Lys Lys Pro
                245

<210> SEQ ID NO 12
<211> LENGTH: 33
<212> TYPE: DNA
<213> ORGANISM: Artificial Sequence
<220> FEATURE:
<223> OTHER INFORMATION: Mutagenesis oligonucleotide

<400> SEQUENCE: 12
gtgctgaccg ccgcggcgtg cgtgggaccg gac                        33

<210> SEQ ID NO 13
<211> LENGTH: 33
<212> TYPE: DNA
<213> ORGANISM: Artificial Sequence
<220> FEATURE:
<223> OTHER INFORMATION: Mutagenesis oligonucleotide

<400> SEQUENCE: 13
gtccggtccc acgcacgccg cggcggtcag cac                        33

<210> SEQ ID NO 14
<211> LENGTH: 33
<212> TYPE: DNA
<213> ORGANISM: Artificial Sequence
<220> FEATURE:
<223> OTHER INFORMATION: Mutagenesis oligonucleotide

<400> SEQUENCE: 14
gcccagatcg gagcggcaat cgccctgctg gag                        33

<210> SEQ ID NO 15
<211> LENGTH: 33
<212> TYPE: DNA
<213> ORGANISM: Artificial Sequence
<220> FEATURE:
<223> OTHER INFORMATION: Mutagenesis oligonucleotide

<400> SEQUENCE: 15
ctccagcagg gcgattgccg ctccgatctg ggc                        33

```
<210> SEQ ID NO 16
<211> LENGTH: 30
<212> TYPE: DNA
<213> ORGANISM: Artificial Sequence
<220> FEATURE:
<223> OTHER INFORMATION: Mutagenesis oligonucleotide

<400> SEQUENCE: 16
tgtcaaggcg acgccggcgg acctctggtg                                              30

<210> SEQ ID NO 17
<211> LENGTH: 30
<212> TYPE: DNA
<213> ORGANISM: Artificial Sequence
<220> FEATURE:
<223> OTHER INFORMATION: Mutagenesis oligonucleotide

<400> SEQUENCE: 17
caccagaggt ccgccggcgt cgccttgaca                                              30

<210> SEQ ID NO 18
<211> LENGTH: 28
<212> TYPE: DNA
<213> ORGANISM: Artificial Sequence
<220> FEATURE:
<223> OTHER INFORMATION: Mutagenesis oligonucleotide

<400> SEQUENCE: 18
caaggagacg ccggcggacc actggtgt                                                28

<210> SEQ ID NO 19
<211> LENGTH: 36
<212> TYPE: DNA
<213> ORGANISM: Artificial Sequence
<220> FEATURE:
<223> OTHER INFORMATION: Mutagenesis oligonucleotide

<400> SEQUENCE: 19
gcacaccagg ggcccgccgg cgtcgccctg gcatga                                       36

<210> SEQ ID NO 20
<211> LENGTH: 771
<212> TYPE: DNA
<213> ORGANISM: Homo sapiens
<220> FEATURE:
<221> NAME/KEY: CDS
<222> LOCATION: (7)..(753)

<400> SEQUENCE: 20 gggccc ctc gag aaa aga atc gtc ggg ggt cag gag gcc ccc agg agc       48
       Leu Glu Lys Arg Ile Val Gly Gly Gln Glu Ala Pro Arg Ser
         1               5                  10 aag tgg ccc tgg cag gtg agc ctg aga gtc cac ggc cca tac tgg atg     96
Lys Trp Pro Trp Gln Val Ser Leu Arg Val His Gly Pro Tyr Trp Met
 15              20                  25                  30 cac ttc tgc ggg ggc tcc ctc atc cac ccc cag tgg gtg ctg acc gcc   144
His Phe Cys Gly Gly Ser Leu Ile His Pro Gln Trp Val Leu Thr Ala
                 35                  40                  45 gcg gcg tgc gtg gga ccg gac gtc aag gat ctg gcc gcc ctc agg gtg   192
Ala Ala Cys Val Gly Pro Asp Val Lys Asp Leu Ala Ala Leu Arg Val
             50                  55                  60 caa ctg cgg gag cag cac ctc tac tac cag gac cag ctg ctg ccg gtc   240
Gln Leu Arg Glu Gln His Leu Tyr Tyr Gln Asp Gln Leu Leu Pro Val
         65                  70                  75 agc agg atc atc gtg cac cca cag ttc tac acc gcc cag atc gga gcg   288
```

```
                                    -continued

Ser Arg Ile Ile Val His Pro Gln Phe Tyr Thr Ala Gln Ile Gly Ala
 80                  85                  90 gac atc gcc ctg ctg gag ctg gag gag ccg gtg aag gtc tcc agc cac    336
Asp Ile Ala Leu Leu Glu Leu Glu Glu Pro Val Lys Val Ser Ser His
 95                 100                 105                 110 gtc cac acg gtc acc ctg ccc cct gcc tca gag acc ttc ccc ccg ggg    384
Val His Thr Val Thr Leu Pro Pro Ala Ser Glu Thr Phe Pro Pro Gly
                115                 120                 125 atg ccg tgc tgg gtc act ggc tgg ggc gat gtg gac aat gat gag cgc    432
Met Pro Cys Trp Val Thr Gly Trp Gly Asp Val Asp Asn Asp Glu Arg
            130                 135                 140 ctc cca ccg cca ttt cct ctg aag cag gtg aag gtc ccc ata atg gaa    480
Leu Pro Pro Pro Phe Pro Leu Lys Gln Val Lys Val Pro Ile Met Glu
        145                 150                 155 aac cac att tgt gac gca aaa tac cac ctt ggc gcc tac acg gga gac    528
Asn His Ile Cys Asp Ala Lys Tyr His Leu Gly Ala Tyr Thr Gly Asp
    160                 165                 170 gac gtc cgc atc gtc cgt gac gac atg ctg tgt gcc ggg aac acc cgg    576
Asp Val Arg Ile Val Arg Asp Asp Met Leu Cys Ala Gly Asn Thr Arg
175                 180                 185                 190 agg gac tca tgc cag ggc gac tcc gga ggg ccc ctg gtg tgc aag gtg    624
Arg Asp Ser Cys Gln Gly Asp Ser Gly Gly Pro Leu Val Cys Lys Val
                195                 200                 205 aat ggc acc tgg ctg cag gcg ggc gtg gtc agc tgg ggc gag ggc tgt    672
Asn Gly Thr Trp Leu Gln Ala Gly Val Val Ser Trp Gly Glu Gly Cys
            210                 215                 220 gcc cag ccc aac cgg cct ggc atc tac acc cgt gtc acc tac tac ttg    720
Ala Gln Pro Asn Arg Pro Gly Ile Tyr Thr Arg Val Thr Tyr Tyr Leu
        225                 230                 235 gac tgg atc cac cac tat gtc ccc aaa aag ccg tgaagcggcc gccgtcgt    771
Asp Trp Ile His His Tyr Val Pro Lys Lys Pro
    240                 245

<210> SEQ ID NO 21
<211> LENGTH: 249
<212> TYPE: PRT
<213> ORGANISM: Homo sapiens

<400> SEQUENCE: 21

Leu Glu Lys Arg Ile Val Gly Gly Gln Glu Ala Pro Arg Ser Lys Trp
  1               5                  10                  15

Pro Trp Gln Val Ser Leu Arg Val His Gly Pro Tyr Trp Met His Phe
                 20                  25                  30

Cys Gly Gly Ser Leu Ile His Pro Gln Trp Val Leu Thr Ala Ala Ala
             35                  40                  45

Cys Val Gly Pro Asp Val Lys Asp Leu Ala Ala Leu Arg Val Gln Leu
         50                  55                  60

Arg Glu Gln His Leu Tyr Tyr Gln Asp Gln Leu Leu Pro Val Ser Arg
 65                  70                  75                  80

Ile Ile Val His Pro Gln Phe Tyr Thr Ala Gln Ile Gly Ala Asp Ile
                 85                  90                  95

Ala Leu Leu Glu Leu Glu Pro Val Lys Val Ser Ser His Val His
            100                 105                 110

Thr Val Thr Leu Pro Pro Ala Ser Glu Thr Phe Pro Pro Gly Met Pro
        115                 120                 125

Cys Trp Val Thr Gly Trp Gly Asp Val Asp Asn Asp Glu Arg Leu Pro
    130                 135                 140

Pro Pro Phe Pro Leu Lys Gln Val Lys Val Pro Ile Met Glu Asn His
```

```
             145                 150                 155                 160
Ile Cys Asp Ala Lys Tyr His Leu Gly Ala Tyr Thr Gly Asp Asp Val
                165                 170                 175

Arg Ile Val Arg Asp Asp Met Leu Cys Ala Gly Asn Thr Arg Arg Asp
                180                 185                 190

Ser Cys Gln Gly Asp Ser Gly Gly Pro Leu Val Cys Lys Val Asn Gly
            195                 200                 205

Thr Trp Leu Gln Ala Gly Val Val Ser Trp Gly Glu Gly Cys Ala Gln
        210                 215                 220

Pro Asn Arg Pro Gly Ile Tyr Thr Arg Val Thr Tyr Tyr Leu Asp Trp
225                 230                 235                 240

Ile His His Tyr Val Pro Lys Lys Pro
                245

<210> SEQ ID NO 22
<211> LENGTH: 771
<212> TYPE: DNA
<213> ORGANISM: Homo sapiens
<220> FEATURE:
<221> NAME/KEY: CDS
<222> LOCATION: (7)..(753)

<400> SEQUENCE: 22 gggccc ctc gag aaa aga atc gtc ggg ggt cag gag gcc ccc agg agc          48
       Leu Glu Lys Arg Ile Val Gly Gly Gln Glu Ala Pro Arg Ser
         1               5                  10 aag tgg ccc tgg cag gtg agc ctg aga gtc cac ggc cca tac tgg atg         96
Lys Trp Pro Trp Gln Val Ser Leu Arg Val His Gly Pro Tyr Trp Met
 15                  20                  25                  30 cac ttc tgc ggg ggc tcc ctc atc cac ccc cag tgg gtg ctg acc gca        144
His Phe Cys Gly Gly Ser Leu Ile His Pro Gln Trp Val Leu Thr Ala
                 35                  40                  45 gcg cac tgc gtg gga ccg gac gtc aag gat ctg gcc gcc ctc agg gtg        192
Ala His Cys Val Gly Pro Asp Val Lys Asp Leu Ala Ala Leu Arg Val
             50                  55                  60 caa ctg cgg gag cag cac ctc tac tac cag gac cag ctg ctg ccg gtc        240
Gln Leu Arg Glu Gln His Leu Tyr Tyr Gln Asp Gln Leu Leu Pro Val
         65                  70                  75 agc agg atc atc gtg cac cca cag ttc tac acc gcc cag atc gga gcg        288
Ser Arg Ile Ile Val His Pro Gln Phe Tyr Thr Ala Gln Ile Gly Ala
     80                  85                  90 gca atc gcc ctg ctg gag ctg gag gag ccg gtg aag gtc tcc agc cac        336
Ala Ile Ala Leu Leu Glu Leu Glu Glu Pro Val Lys Val Ser Ser His
 95                 100                 105                 110 gtc cac acg gtc acc ctg ccc cct gcc tca gag acc ttc ccc ccg ggg        384
Val His Thr Val Thr Leu Pro Pro Ala Ser Glu Thr Phe Pro Pro Gly
                115                 120                 125 atg ccg tgc tgg gtc act ggc tgg ggc gat gtg gac aat gat gag cgc        432
Met Pro Cys Trp Val Thr Gly Trp Gly Asp Val Asp Asn Asp Glu Arg
            130                 135                 140 ctc cca ccg cca ttt cct ctg aag cag gtg aag gtc ccc ata atg gaa        480
Leu Pro Pro Pro Phe Pro Leu Lys Gln Val Lys Val Pro Ile Met Glu
        145                 150                 155 aac cac att tgt gac gca aaa tac cac ctt ggc gcc tac acg gga gac        528
Asn His Ile Cys Asp Ala Lys Tyr His Leu Gly Ala Tyr Thr Gly Asp
160                 165                 170 gac gtc cgc atc gtc cgt gac gac atg ctg tgt gcc ggg aac acc cgg        576
Asp Val Arg Ile Val Arg Asp Asp Met Leu Cys Ala Gly Asn Thr Arg
175                 180                 185                 190
```

```
agg gac tca tgc cag ggc gac tcc gga ggg ccc ctg gtg tgc aag gtg    624
Arg Asp Ser Cys Gln Gly Asp Ser Gly Gly Pro Leu Val Cys Lys Val
            195                 200                 205 aat ggc acc tgg ctg cag gcg ggc gtg gtc agc tgg ggc gag ggc tgt    672
Asn Gly Thr Trp Leu Gln Ala Gly Val Val Ser Trp Gly Glu Gly Cys
        210                 215                 220 gcc cag ccc aac cgg cct ggc atc tac acc cgt gtc acc tac tac ttg    720
Ala Gln Pro Asn Arg Pro Gly Ile Tyr Thr Arg Val Thr Tyr Tyr Leu
    225                 230                 235 gac tgg atc cac cac tat gtc ccc aaa aag ccg tgaagcggcc gccgtcgt    771
Asp Trp Ile His His Tyr Val Pro Lys Lys Pro
240                 245
```

<210> SEQ ID NO 23
<211> LENGTH: 249
<212> TYPE: PRT
<213> ORGANISM: Homo sapiens

<400> SEQUENCE: 23

```
Leu Glu Lys Arg Ile Val Gly Gly Gln Glu Ala Pro Arg Ser Lys Trp
1               5                   10                  15

Pro Trp Gln Val Ser Leu Arg Val His Gly Pro Tyr Trp Met His Phe
            20                  25                  30

Cys Gly Gly Ser Leu Ile His Pro Gln Trp Val Leu Thr Ala Ala His
        35                  40                  45

Cys Val Gly Pro Asp Val Lys Asp Leu Ala Ala Leu Arg Val Gln Leu
    50                  55                  60

Arg Glu Gln His Leu Tyr Tyr Gln Asp Gln Leu Leu Pro Val Ser Arg
65                  70                  75                  80

Ile Ile Val His Pro Gln Phe Tyr Thr Ala Gln Ile Gly Ala Ala Ile
                85                  90                  95

Ala Leu Leu Glu Leu Glu Glu Pro Val Lys Val Ser Ser His Val His
            100                 105                 110

Thr Val Thr Leu Pro Pro Ala Ser Glu Thr Phe Pro Pro Gly Met Pro
        115                 120                 125

Cys Trp Val Thr Gly Trp Gly Asp Val Asp Asn Asp Glu Arg Leu Pro
    130                 135                 140

Pro Pro Phe Pro Leu Lys Gln Val Lys Val Pro Ile Met Glu Asn His
145                 150                 155                 160

Ile Cys Asp Ala Lys Tyr His Leu Gly Ala Tyr Thr Gly Asp Asp Val
                165                 170                 175

Arg Ile Val Arg Asp Asp Met Leu Cys Ala Gly Asn Thr Arg Arg Asp
            180                 185                 190

Ser Cys Gln Gly Asp Ser Gly Gly Pro Leu Val Cys Lys Val Asn Gly
        195                 200                 205

Thr Trp Leu Gln Ala Gly Val Val Ser Trp Gly Glu Gly Cys Ala Gln
    210                 215                 220

Pro Asn Arg Pro Gly Ile Tyr Thr Arg Val Thr Tyr Tyr Leu Asp Trp
225                 230                 235                 240

Ile His His Tyr Val Pro Lys Lys Pro
                245
```

<210> SEQ ID NO 24
<211> LENGTH: 771
<212> TYPE: DNA
<213> ORGANISM: Homo sapiens
<220> FEATURE:
<221> NAME/KEY: CDS

<222> LOCATION: (7)..(753)

<400> SEQUENCE: 24

| | | | | | | | | | | | | | | | |
|---|---|---|---|---|---|---|---|---|---|---|---|---|---|---|---|
| gggccc | ctc | gag | aaa | aga | atc | gtc | ggg | ggt | cag | gag | gcc | ccc | agg | agc | 48 |
| | Leu | Glu | Lys | Arg | Ile | Val | Gly | Gly | Gln | Glu | Ala | Pro | Arg | Ser | |
| | 1 | | | 5 | | | | | 10 | | | | | | |

| aag | tgg | ccc | tgg | cag | gtg | agc | ctg | aga | gtc | cac | ggc | cca | tac | tgg | atg | 96 |
|---|---|---|---|---|---|---|---|---|---|---|---|---|---|---|---|---|
| Lys | Trp | Pro | Trp | Gln | Val | Ser | Leu | Arg | Val | His | Gly | Pro | Tyr | Trp | Met | |
| 15 | | | | 20 | | | | | 25 | | | | | | 30 | |

| cac | ttc | tgc | ggg | ggc | tcc | ctc | atc | cac | ccc | cag | tgg | gtg | ctg | acc | gca | 144 |
|---|---|---|---|---|---|---|---|---|---|---|---|---|---|---|---|---|
| His | Phe | Cys | Gly | Gly | Ser | Leu | Ile | His | Pro | Gln | Trp | Val | Leu | Thr | Ala | |
| | | | | 35 | | | | | 40 | | | | | 45 | | |

| gcg | cac | tgc | gtg | gga | ccg | gac | gtc | aag | gat | ctg | gcc | gcc | ctc | agg | gtg | 192 |
|---|---|---|---|---|---|---|---|---|---|---|---|---|---|---|---|---|
| Ala | His | Cys | Val | Gly | Pro | Asp | Val | Lys | Asp | Leu | Ala | Ala | Leu | Arg | Val | |
| | | 50 | | | | | 55 | | | | | 60 | | | | |

| caa | ctg | cgg | gag | cag | cac | ctc | tac | tac | cag | gac | cag | ctg | ctg | ccg | gtc | 240 |
|---|---|---|---|---|---|---|---|---|---|---|---|---|---|---|---|---|
| Gln | Leu | Arg | Glu | Gln | His | Leu | Tyr | Tyr | Gln | Asp | Gln | Leu | Leu | Pro | Val | |
| 65 | | | | | 70 | | | | | 75 | | | | | | |

| agc | agg | atc | atc | gtg | cac | cca | cag | ttc | tac | acc | gcc | cag | atc | gga | gcg | 288 |
|---|---|---|---|---|---|---|---|---|---|---|---|---|---|---|---|---|
| Ser | Arg | Ile | Ile | Val | His | Pro | Gln | Phe | Tyr | Thr | Ala | Gln | Ile | Gly | Ala | |
| 80 | | | | | 85 | | | | | 90 | | | | | | |

| gac | atc | gcc | ctg | ctg | gag | ctg | gag | gag | ccg | gtg | aag | gtc | tcc | agc | cac | 336 |
|---|---|---|---|---|---|---|---|---|---|---|---|---|---|---|---|---|
| Asp | Ile | Ala | Leu | Leu | Glu | Leu | Glu | Glu | Pro | Val | Lys | Val | Ser | Ser | His | |
| 95 | | | | | 100 | | | | | 105 | | | | | 110 | |

| gtc | cac | acg | gtc | acc | ctg | ccc | cct | gcc | tca | gag | acc | ttc | ccc | ccg | ggg | 384 |
|---|---|---|---|---|---|---|---|---|---|---|---|---|---|---|---|---|
| Val | His | Thr | Val | Thr | Leu | Pro | Pro | Ala | Ser | Glu | Thr | Phe | Pro | Pro | Gly | |
| | | | | 115 | | | | | 120 | | | | | 125 | | |

| atg | ccg | tgc | tgg | gtc | act | ggc | tgg | ggc | gat | gtg | gac | aat | gat | gag | cgc | 432 |
|---|---|---|---|---|---|---|---|---|---|---|---|---|---|---|---|---|
| Met | Pro | Cys | Trp | Val | Thr | Gly | Trp | Gly | Asp | Val | Asp | Asn | Asp | Glu | Arg | |
| | | | | 130 | | | | | 135 | | | | | 140 | | |

| ctc | cca | ccg | cca | ttt | cct | ctg | aag | cag | gtg | aag | gtc | ccc | ata | atg | gaa | 480 |
|---|---|---|---|---|---|---|---|---|---|---|---|---|---|---|---|---|
| Leu | Pro | Pro | Pro | Phe | Pro | Leu | Lys | Gln | Val | Lys | Val | Pro | Ile | Met | Glu | |
| | | 145 | | | | | 150 | | | | | 155 | | | | |

| aac | cac | att | tgt | gac | gca | aaa | tac | cac | ctt | ggc | gcc | tac | acg | gga | gac | 528 |
|---|---|---|---|---|---|---|---|---|---|---|---|---|---|---|---|---|
| Asn | His | Ile | Cys | Asp | Ala | Lys | Tyr | His | Leu | Gly | Ala | Tyr | Thr | Gly | Asp | |
| | 160 | | | | | 165 | | | | | 170 | | | | | |

| gac | gtc | cgc | atc | gtc | cgt | gac | gac | atg | ctg | tgt | gcc | ggg | aac | acc | cgg | 576 |
|---|---|---|---|---|---|---|---|---|---|---|---|---|---|---|---|---|
| Asp | Val | Arg | Ile | Val | Arg | Asp | Asp | Met | Leu | Cys | Ala | Gly | Asn | Thr | Arg | |
| 175 | | | | | 180 | | | | | 185 | | | | | 190 | |

| agg | gac | tca | tgt | caa | ggc | gac | gcc | ggc | gga | cct | ctg | gtg | tgc | aag | gtg | 624 |
|---|---|---|---|---|---|---|---|---|---|---|---|---|---|---|---|---|
| Arg | Asp | Ser | Cys | Gln | Gly | Asp | Ala | Gly | Gly | Pro | Leu | Val | Cys | Lys | Val | |
| | | | | 195 | | | | | 200 | | | | | 205 | | |

| aat | ggc | acc | tgg | ctg | cag | gcg | ggc | gtg | gtc | agc | tgg | ggc | gag | ggc | tgt | 672 |
|---|---|---|---|---|---|---|---|---|---|---|---|---|---|---|---|---|
| Asn | Gly | Thr | Trp | Leu | Gln | Ala | Gly | Val | Val | Ser | Trp | Gly | Glu | Gly | Cys | |
| | | 210 | | | | | 215 | | | | | 220 | | | | |

| gcc | cag | ccc | aac | cgg | cct | ggc | atc | tac | acc | cgt | gtc | acc | tac | tac | ttg | 720 |
|---|---|---|---|---|---|---|---|---|---|---|---|---|---|---|---|---|
| Ala | Gln | Pro | Asn | Arg | Pro | Gly | Ile | Tyr | Thr | Arg | Val | Thr | Tyr | Tyr | Leu | |
| | | 225 | | | | | 230 | | | | | 235 | | | | |

| gac | tgg | atc | cac | cac | tat | gtc | ccc | aaa | aag | ccg | tgaagcggcc | gccgtcgt | | | | 771 |
|---|---|---|---|---|---|---|---|---|---|---|---|---|---|---|---|---|
| Asp | Trp | Ile | His | His | Tyr | Val | Pro | Lys | Lys | Pro | | | | | | |
| | 240 | | | | | 245 | | | | | | | | | | |

<210> SEQ ID NO 25
<211> LENGTH: 249
<212> TYPE: PRT
<213> ORGANISM: Homo sapiens

<400> SEQUENCE: 25

| Leu | Glu | Lys | Arg | Ile | Val | Gly | Gly | Gln | Glu | Ala | Pro | Arg | Ser | Lys | Trp |
|---|---|---|---|---|---|---|---|---|---|---|---|---|---|---|---|
| 1 | | | | 5 | | | | | 10 | | | | | 15 | |

```
Pro Trp Gln Val Ser Leu Arg Val His Gly Pro Tyr Trp Met His Phe
        20                  25                  30

Cys Gly Gly Ser Leu Ile His Pro Gln Trp Val Leu Thr Ala Ala His
            35                  40                  45

Cys Val Gly Pro Asp Val Lys Asp Leu Ala Ala Leu Arg Val Gln Leu
 50                  55                  60

Arg Glu Gln His Leu Tyr Tyr Gln Asp Gln Leu Leu Pro Val Ser Arg
 65                  70                  75                  80

Ile Ile Val His Pro Gln Phe Tyr Thr Ala Gln Ile Gly Ala Asp Ile
                85                  90                  95

Ala Leu Leu Glu Leu Glu Pro Val Lys Val Ser Ser His Val His
            100                 105                 110

Thr Val Thr Leu Pro Pro Ala Ser Glu Thr Phe Pro Pro Gly Met Pro
            115                 120                 125

Cys Trp Val Thr Gly Trp Gly Asp Val Asp Asn Asp Glu Arg Leu Pro
130                 135                 140

Pro Pro Phe Pro Leu Lys Gln Val Lys Val Pro Ile Met Glu Asn His
145                 150                 155                 160

Ile Cys Asp Ala Lys Tyr His Leu Gly Ala Tyr Thr Gly Asp Asp Val
                165                 170                 175

Arg Ile Val Arg Asp Asp Met Leu Cys Ala Gly Asn Thr Arg Arg Asp
            180                 185                 190

Ser Cys Gln Gly Asp Ala Gly Gly Pro Leu Val Cys Lys Val Asn Gly
            195                 200                 205

Thr Trp Leu Gln Ala Gly Val Val Ser Trp Gly Glu Gly Cys Ala Gln
            210                 215                 220

Pro Asn Arg Pro Gly Ile Tyr Thr Arg Val Thr Tyr Tyr Leu Asp Trp
225                 230                 235                 240

Ile His His Tyr Val Pro Lys Lys Pro
                245

<210> SEQ ID NO 26
<211> LENGTH: 771
<212> TYPE: DNA
<213> ORGANISM: Homo sapiens
<220> FEATURE:
<221> NAME/KEY: CDS
<222> LOCATION: (7)..(753)

<400> SEQUENCE: 26 gggccc ctc gag aaa aga atc gtc ggg ggt cag gag gcc ccc agg agc        48
       Leu Glu Lys Arg Ile Val Gly Gly Gln Glu Ala Pro Arg Ser
        1               5                   10 aag tgg ccc tgg cag gtg agc ctg aga gtc cac ggc cca tac tgg atg       96
Lys Trp Pro Trp Gln Val Ser Leu Arg Val His Gly Pro Tyr Trp Met
 15                  20                  25                  30 cac ttc tgc ggg ggc tcc ctc atc cac ccc cag tgg gtg ctg acc gca      144
His Phe Cys Gly Gly Ser Leu Ile His Pro Gln Trp Val Leu Thr Ala
                 35                  40                  45 gcg cac tgc gtg gga ccg gac gtc aag gat ctg gcc gcc ctc agg gtg      192
Ala His Cys Val Gly Pro Asp Val Lys Asp Leu Ala Ala Leu Arg Val
             50                  55                  60 caa ctg cgg gag cag cac ctc tac tac cag gac cag ctg ctg ccg gtc      240
Gln Leu Arg Glu Gln His Leu Tyr Tyr Gln Asp Gln Leu Leu Pro Val
         65                  70                  75 agc agg atc atc gtg cac cca cag ttc tac acc gcc cag atc gga gcg      288
Ser Arg Ile Ile Val His Pro Gln Phe Tyr Thr Ala Gln Ile Gly Ala
     80                  85                  90
```

```
gac atc gcc ctg ctg gag ctg gag gag ccg gtg aag gtc tcc agc cac       336
Asp Ile Ala Leu Leu Glu Leu Glu Glu Pro Val Lys Val Ser Ser His
 95                 100                 105                 110 gtc cac acg gtc acc ctg ccc cct gcc tca gag acc ttc ccc ccg ggg       384
Val His Thr Val Thr Leu Pro Pro Ala Ser Glu Thr Phe Pro Pro Gly
                115                 120                 125 atg ccg tgc tgg gtc act ggc tgg ggc gat gtg gac aat gat gag cgc       432
Met Pro Cys Trp Val Thr Gly Trp Gly Asp Val Asp Asn Asp Glu Arg
            130                 135                 140 ctc cca ccg cca ttt cct ctg aag cag gtg aag gtc ccc ata atg gaa       480
Leu Pro Pro Pro Phe Pro Leu Lys Gln Val Lys Val Pro Ile Met Glu
        145                 150                 155 aac cac att tgt gac gca aaa tac cac ctt ggc gcc tac acg gga gac       528
Asn His Ile Cys Asp Ala Lys Tyr His Leu Gly Ala Tyr Thr Gly Asp
    160                 165                 170 gac gtc cgc atc gtc cgt gac gac atg ctg tgt gcc ggg aac acc cgg       576
Asp Val Arg Ile Val Arg Asp Asp Met Leu Cys Ala Gly Asn Thr Arg
175                 180                 185                 190 agg gac tca tgc caa gga gac gcc ggc gga cca ctg gtg tgc aag gtg       624
Arg Asp Ser Cys Gln Gly Asp Ala Gly Gly Pro Leu Val Cys Lys Val
                195                 200                 205 aat ggc acc tgg ctg cag gcg ggc gtg gtc agc tgg ggc gag ggc tgt       672
Asn Gly Thr Trp Leu Gln Ala Gly Val Val Ser Trp Gly Glu Gly Cys
            210                 215                 220 gcc cag ccc aac cgg cct ggc atc tac acc cgt gtc acc tac tac ttg       720
Ala Gln Pro Asn Arg Pro Gly Ile Tyr Thr Arg Val Thr Tyr Tyr Leu
        225                 230                 235 gac tgg atc cac cac tat gtc ccc aaa aag ccg tgaagcggcc gccgtcgt      771
Asp Trp Ile His His Tyr Val Pro Lys Lys Pro
    240                 245

<210> SEQ ID NO 27
<211> LENGTH: 249
<212> TYPE: PRT
<213> ORGANISM: Homo sapiens

<400> SEQUENCE: 27

Leu Glu Lys Arg Ile Val Gly Gly Gln Glu Ala Pro Arg Ser Lys Trp
1               5                   10                  15

Pro Trp Gln Val Ser Leu Arg Val His Gly Pro Tyr Trp Met His Phe
            20                  25                  30

Cys Gly Gly Ser Leu Ile His Pro Gln Trp Val Leu Thr Ala Ala His
        35                  40                  45

Cys Val Gly Pro Asp Val Lys Asp Leu Ala Ala Leu Arg Val Gln Leu
    50                  55                  60

Arg Glu Gln His Leu Tyr Tyr Gln Asp Gln Leu Leu Pro Val Ser Arg
65                  70                  75                  80

Ile Ile Val His Pro Gln Phe Tyr Thr Ala Gln Ile Gly Ala Asp Ile
                85                  90                  95

Ala Leu Leu Glu Leu Glu Glu Pro Val Lys Val Ser Ser His Val His
            100                 105                 110

Thr Val Thr Leu Pro Pro Ala Ser Glu Thr Phe Pro Pro Gly Met Pro
        115                 120                 125

Cys Trp Val Thr Gly Trp Gly Asp Val Asp Asn Asp Glu Arg Leu Pro
    130                 135                 140

Pro Pro Phe Pro Leu Lys Gln Val Lys Val Pro Ile Met Glu Asn His
145                 150                 155                 160
```

```
Ile Cys Asp Ala Lys Tyr His Leu Gly Ala Tyr Thr Gly Asp Asp Val
            165                 170                 175

Arg Ile Val Arg Asp Asp Met Leu Cys Ala Gly Asn Thr Arg Arg Asp
            180                 185                 190

Ser Cys Gln Gly Asp Ala Gly Gly Pro Leu Val Cys Lys Val Asn Gly
        195                 200                 205

Thr Trp Leu Gln Ala Gly Val Val Ser Trp Gly Glu Gly Cys Ala Gln
    210                 215                 220

Pro Asn Arg Pro Gly Ile Tyr Thr Arg Val Thr Tyr Leu Asp Trp
225                 230                 235                 240

Ile His His Tyr Val Pro Lys Lys Pro
                245

<210> SEQ ID NO 28
<211> LENGTH: 735
<212> TYPE: DNA
<213> ORGANISM: Homo sapiens
<220> FEATURE:
<221> NAME/KEY: CDS
<222> LOCATION: (1)..(735)

<400> SEQUENCE: 28 atc gtc ggg ggt cag gag gcc ccc agg agc aag tgg ccc tgg cag gtg        48
Ile Val Gly Gly Gln Glu Ala Pro Arg Ser Lys Trp Pro Trp Gln Val
1               5                   10                  15 agc ctg aga gtc cac ggc cca tac tgg atg cac ttc tgc ggg ggc tcc        96
Ser Leu Arg Val His Gly Pro Tyr Trp Met His Phe Cys Gly Gly Ser
            20                  25                  30 ctc atc cac ccc cag tgg gtg ctg acc gcc gcg gcg tgc gtg gga ccg       144
Leu Ile His Pro Gln Trp Val Leu Thr Ala Ala Ala Cys Val Gly Pro
        35                  40                  45 gac gtc aag gat ctg gcc gcc ctc agg gtg caa ctg cgg gag cag cac       192
Asp Val Lys Asp Leu Ala Ala Leu Arg Val Gln Leu Arg Glu Gln His
    50                  55                  60 ctc tac tac cag gac cag ctg ctg ccg gtc agc agg atc atc gtg cac       240
Leu Tyr Tyr Gln Asp Gln Leu Leu Pro Val Ser Arg Ile Ile Val His
65                  70                  75                  80 cca cag ttc tac acc gcc cag atc gga gcg gac atc gcc ctg ctg gag       288
Pro Gln Phe Tyr Thr Ala Gln Ile Gly Ala Asp Ile Ala Leu Leu Glu
                85                  90                  95 ctg gag gag ccg gtg aag gtc tcc agc cac gtc cac acg gtc acc ctg       336
Leu Glu Glu Pro Val Lys Val Ser Ser His Val His Thr Val Thr Leu
            100                 105                 110 ccc cct gcc tca gag acc ttc ccc ccg ggg atg ccg tgc tgg gtc act       384
Pro Pro Ala Ser Glu Thr Phe Pro Pro Gly Met Pro Cys Trp Val Thr
        115                 120                 125 ggc tgg ggc gat gtg gac aat gat gag cgc ctc cca ccg cca ttt cct       432
Gly Trp Gly Asp Val Asp Asn Asp Glu Arg Leu Pro Pro Pro Phe Pro
    130                 135                 140 ctg aag cag gtg aag gtc ccc ata atg gaa aac cac att tgt gac gca       480
Leu Lys Gln Val Lys Val Pro Ile Met Glu Asn His Ile Cys Asp Ala
145                 150                 155                 160 aaa tac cac ctt ggc gcc tac acg gga gac gac gtc cgc atc gtc cgt       528
Lys Tyr His Leu Gly Ala Tyr Thr Gly Asp Asp Val Arg Ile Val Arg
                165                 170                 175 gac gac atg ctg tgt gcc ggg aac acc cgg agg gac tca tgc cag ggc       576
Asp Asp Met Leu Cys Ala Gly Asn Thr Arg Arg Asp Ser Cys Gln Gly
            180                 185                 190 gac tcc gga ggg ccc ctg gtg tgc aag gtg aat ggc acc tgg ctg cag       624
Asp Ser Gly Gly Pro Leu Val Cys Lys Val Asn Gly Thr Trp Leu Gln
```

```
                    195                 200                 205
gcg ggc gtg gtc agc tgg ggc gag ggc tgt gcc cag ccc aac cgg cct       672
Ala Gly Val Val Ser Trp Gly Glu Gly Cys Ala Gln Pro Asn Arg Pro
210                 215                 220 ggc atc tac acc cgt gtc acc tac tac ttg gac tgg atc cac cac tat       720
Gly Ile Tyr Thr Arg Val Thr Tyr Tyr Leu Asp Trp Ile His His Tyr
225                 230                 235                 240 gtc ccc aaa aag ccg                                                   735
Val Pro Lys Lys Pro
            245
```

<210> SEQ ID NO 29
<211> LENGTH: 245
<212> TYPE: PRT
<213> ORGANISM: Homo sapiens

<400> SEQUENCE: 29

```
Ile Val Gly Gly Gln Glu Ala Pro Arg Ser Lys Trp Pro Trp Gln Val
1               5                   10                  15

Ser Leu Arg Val His Gly Pro Tyr Trp Met His Phe Cys Gly Gly Ser
            20                  25                  30

Leu Ile His Pro Gln Trp Val Leu Thr Ala Ala Cys Val Gly Pro
        35                  40                  45

Asp Val Lys Asp Leu Ala Ala Leu Arg Val Gln Leu Arg Glu Gln His
    50                  55                  60

Leu Tyr Tyr Gln Asp Gln Leu Leu Pro Val Ser Arg Ile Ile Val His
65                  70                  75                  80

Pro Gln Phe Tyr Thr Ala Gln Ile Gly Ala Asp Ile Ala Leu Leu Glu
                85                  90                  95

Leu Glu Glu Pro Val Lys Val Ser Ser His Val His Thr Val Thr Leu
            100                 105                 110

Pro Pro Ala Ser Glu Thr Phe Pro Pro Gly Met Pro Cys Trp Val Thr
        115                 120                 125

Gly Trp Gly Asp Val Asp Asn Asp Glu Arg Leu Pro Pro Pro Phe Pro
    130                 135                 140

Leu Lys Gln Val Lys Val Pro Ile Met Glu Asn His Ile Cys Asp Ala
145                 150                 155                 160

Lys Tyr His Leu Gly Ala Tyr Thr Gly Asp Asp Val Arg Ile Val Arg
                165                 170                 175

Asp Asp Met Leu Cys Ala Gly Asn Thr Arg Arg Asp Ser Cys Gln Gly
            180                 185                 190

Asp Ser Gly Gly Pro Leu Val Cys Lys Val Asn Gly Thr Trp Leu Gln
        195                 200                 205

Ala Gly Val Val Ser Trp Gly Glu Gly Cys Ala Gln Pro Asn Arg Pro
    210                 215                 220

Gly Ile Tyr Thr Arg Val Thr Tyr Tyr Leu Asp Trp Ile His His Tyr
225                 230                 235                 240

Val Pro Lys Lys Pro
            245
```

<210> SEQ ID NO 30
<211> LENGTH: 735
<212> TYPE: DNA
<213> ORGANISM: Homo sapiens
<220> FEATURE:
<221> NAME/KEY: CDS
<222> LOCATION: (1)..(735)

```
<400> SEQUENCE: 30 atc gtc ggg ggt cag gag gcc ccc agg agc aag tgg ccc tgg cag gtg        48
Ile Val Gly Gly Gln Glu Ala Pro Arg Ser Lys Trp Pro Trp Gln Val
 1               5                  10                  15 agc ctg aga gtc cac ggc cca tac tgg atg cac ttc tgc ggg ggc tcc        96
Ser Leu Arg Val His Gly Pro Tyr Trp Met His Phe Cys Gly Gly Ser
             20                  25                  30 ctc atc cac ccc cag tgg gtg ctg acc gcg cac tgc gtg gga ccg           144
Leu Ile His Pro Gln Trp Val Leu Thr Ala His Cys Val Gly Pro
         35                  40                  45 gac gtc aag gat ctg gcc gcc ctc agg gtg caa ctg cgg gag cag cac       192
Asp Val Lys Asp Leu Ala Ala Leu Arg Val Gln Leu Arg Glu Gln His
 50                  55                  60 ctc tac tac cag gac cag ctg ctg ccg gtc agc agg atc atc gtg cac       240
Leu Tyr Tyr Gln Asp Gln Leu Leu Pro Val Ser Arg Ile Ile Val His
 65                  70                  75                  80 cca cag ttc tac acc gcc cag atc gga gcg gca atc gcc ctg ctg gag       288
Pro Gln Phe Tyr Thr Ala Gln Ile Gly Ala Ala Ile Ala Leu Leu Glu
             85                  90                  95 ctg gag gag ccg gtg aag gtc tcc agc cac gtc cac acg gtc acc ctg       336
Leu Glu Glu Pro Val Lys Val Ser Ser His Val His Thr Val Thr Leu
            100                 105                 110 ccc cct gcc tca gag acc ttc ccc ccg ggg atg ccg tgc tgg gtc act       384
Pro Pro Ala Ser Glu Thr Phe Pro Pro Gly Met Pro Cys Trp Val Thr
        115                 120                 125 ggc tgg ggc gat gtg gac aat gat gag cgc ctc cca ccg cca ttt cct       432
Gly Trp Gly Asp Val Asp Asn Asp Glu Arg Leu Pro Pro Pro Phe Pro
130                 135                 140 ctg aag cag gtg aag gtc ccc ata atg gaa aac cac att tgt gac gca       480
Leu Lys Gln Val Lys Val Pro Ile Met Glu Asn His Ile Cys Asp Ala
145                 150                 155                 160 aaa tac cac ctt ggc gcc tac acg gga gac gac gtc cgc atc gtc cgt       528
Lys Tyr His Leu Gly Ala Tyr Thr Gly Asp Asp Val Arg Ile Val Arg
                165                 170                 175 gac gac atg ctg tgt gcc ggg aac acc cgg agg gac tca tgc cag ggc       576
Asp Asp Met Leu Cys Ala Gly Asn Thr Arg Arg Asp Ser Cys Gln Gly
            180                 185                 190 gac tcc gga ggg ccc ctg gtg tgc aag gtg aat ggc acc tgg ctg cag       624
Asp Ser Gly Gly Pro Leu Val Cys Lys Val Asn Gly Thr Trp Leu Gln
        195                 200                 205 gcg ggc gtg gtc agc tgg ggc gag ggc tgt gcc cag ccc aac cgg cct       672
Ala Gly Val Val Ser Trp Gly Glu Gly Cys Ala Gln Pro Asn Arg Pro
    210                 215                 220 ggc atc tac acc cgt gtc acc tac tac ttg gac tgg atc cac cac tat       720
Gly Ile Tyr Thr Arg Val Thr Tyr Tyr Leu Asp Trp Ile His His Tyr
225                 230                 235                 240 gtc ccc aaa aag ccg                                                   735
Val Pro Lys Lys Pro
                245

<210> SEQ ID NO 31
<211> LENGTH: 245
<212> TYPE: PRT
<213> ORGANISM: Homo sapiens

<400> SEQUENCE: 31

Ile Val Gly Gly Gln Glu Ala Pro Arg Ser Lys Trp Pro Trp Gln Val
 1               5                  10                  15

Ser Leu Arg Val His Gly Pro Tyr Trp Met His Phe Cys Gly Gly Ser
             20                  25                  30
```

```
Leu Ile His Pro Gln Trp Val Leu Thr Ala Ala His Cys Val Gly Pro
         35                  40                  45

Asp Val Lys Asp Leu Ala Ala Leu Arg Val Gln Leu Arg Glu Gln His
     50                  55                  60

Leu Tyr Tyr Gln Asp Gln Leu Leu Pro Val Ser Arg Ile Ile Val His
 65                  70                  75                  80

Pro Gln Phe Tyr Thr Ala Gln Ile Gly Ala Ala Ile Ala Leu Leu Glu
                 85                  90                  95

Leu Glu Glu Pro Val Lys Val Ser Ser His Val His Thr Val Thr Leu
             100                 105                 110

Pro Pro Ala Ser Glu Thr Phe Pro Pro Gly Met Pro Cys Trp Val Thr
         115                 120                 125

Gly Trp Gly Asp Val Asp Asn Asp Glu Arg Leu Pro Pro Phe Pro
     130                 135                 140

Leu Lys Gln Val Lys Val Pro Ile Met Glu Asn His Ile Cys Asp Ala
145                 150                 155                 160

Lys Tyr His Leu Gly Ala Tyr Thr Gly Asp Asp Val Arg Ile Val Arg
                 165                 170                 175

Asp Asp Met Leu Cys Ala Gly Asn Thr Arg Arg Asp Ser Cys Gln Gly
             180                 185                 190

Asp Ser Gly Gly Pro Leu Val Cys Lys Val Asn Gly Thr Trp Leu Gln
         195                 200                 205

Ala Gly Val Val Ser Trp Gly Glu Gly Cys Ala Gln Pro Asn Arg Pro
     210                 215                 220

Gly Ile Tyr Thr Arg Val Thr Tyr Leu Asp Trp Ile His His Tyr
225                 230                 235                 240

Val Pro Lys Lys Pro
             245

<210> SEQ ID NO 32
<211> LENGTH: 735
<212> TYPE: DNA
<213> ORGANISM: Homo sapiens
<220> FEATURE:
<221> NAME/KEY: CDS
<222> LOCATION: (1)..(735)

<400> SEQUENCE: 32 atc gtc ggg ggt cag gag gcc ccc agg agc aag tgg ccc tgg cag gtg    48
Ile Val Gly Gly Gln Glu Ala Pro Arg Ser Lys Trp Pro Trp Gln Val
 1               5                  10                  15 agc ctg aga gtc cac ggc cca tac tgg atg cac ttc tgc ggg ggc tcc    96
Ser Leu Arg Val His Gly Pro Tyr Trp Met His Phe Cys Gly Gly Ser
             20                  25                  30 ctc atc cac ccc cag tgg gtg ctg acc gca gcg cac tgc gtg gga ccg   144
Leu Ile His Pro Gln Trp Val Leu Thr Ala Ala His Cys Val Gly Pro
         35                  40                  45 gac gtc aag gat ctg gcc gcc ctc agg gtg caa ctg cgg gag cag cac   192
Asp Val Lys Asp Leu Ala Ala Leu Arg Val Gln Leu Arg Glu Gln His
     50                  55                  60 ctc tac tac cag gac cag ctg ctg ccg gtc agc agg atc atc gtg cac   240
Leu Tyr Tyr Gln Asp Gln Leu Leu Pro Val Ser Arg Ile Ile Val His
 65                  70                  75                  80 cca cag ttc tac acc gcc cag atc gga gcg gac atc gcc ctg ctg gag   288
Pro Gln Phe Tyr Thr Ala Gln Ile Gly Ala Asp Ile Ala Leu Leu Glu
                 85                  90                  95 ctg gag gag ccg gtg aag gtc tcc agc cac gtc cac acg gtc acc ctg   336
```

-continued

| | | | | | | | | | | | | |
|---|---|---|---|---|---|---|---|---|---|---|---|---|
| Leu | Glu | Glu | Pro | Val | Lys | Val | Ser | Ser | His | Val | His | Thr | Val | Thr | Leu |
| | | | 100 | | | | | 105 | | | | | 110 | | |

```
ccc cct gcc tca gag acc ttc ccc ccg ggg atg ccg tgc tgg gtc act       384
Pro Pro Ala Ser Glu Thr Phe Pro Pro Gly Met Pro Cys Trp Val Thr
        115                 120                 125 ggc tgg ggc gat gtg gac aat gat gag cgc ctc cca ccg cca ttt cct       432
Gly Trp Gly Asp Val Asp Asn Asp Glu Arg Leu Pro Pro Pro Phe Pro
130                 135                 140 ctg aag cag gtg aag gtc ccc ata atg gaa aac cac att tgt gac gca       480
Leu Lys Gln Val Lys Val Pro Ile Met Glu Asn His Ile Cys Asp Ala
145                 150                 155                 160 aaa tac cac ctt ggc gcc tac acg gga gac gac gtc cgc atc gtc cgt       528
Lys Tyr His Leu Gly Ala Tyr Thr Gly Asp Asp Val Arg Ile Val Arg
                165                 170                 175 gac gac atg ctg tgt gcc ggg aac acc cgg agg gac tca tgt caa ggc       576
Asp Asp Met Leu Cys Ala Gly Asn Thr Arg Arg Asp Ser Cys Gln Gly
            180                 185                 190 gac gcc ggc gga cct ctg gtg tgc aag gtg aat ggc acc tgg ctg cag       624
Asp Ala Gly Gly Pro Leu Val Cys Lys Val Asn Gly Thr Trp Leu Gln
        195                 200                 205 gcg ggc gtg gtc agc tgg ggc gag ggc tgt gcc cag ccc aac cgg cct       672
Ala Gly Val Val Ser Trp Gly Glu Gly Cys Ala Gln Pro Asn Arg Pro
    210                 215                 220 ggc atc tac acc cgt gtc acc tac tac ttg gac tgg atc cac cac tat       720
Gly Ile Tyr Thr Arg Val Thr Tyr Tyr Leu Asp Trp Ile His His Tyr
225                 230                 235                 240 gtc ccc aaa aag ccg                                                   735
Val Pro Lys Lys Pro
                245
```

<210> SEQ ID NO 33
<211> LENGTH: 245
<212> TYPE: PRT
<213> ORGANISM: Homo sapiens

<400> SEQUENCE: 33

```
Ile Val Gly Gly Gln Glu Ala Pro Arg Ser Lys Trp Pro Trp Gln Val
1               5                   10                  15

Ser Leu Arg Val His Gly Pro Tyr Trp Met His Phe Cys Gly Gly Ser
            20                  25                  30

Leu Ile His Pro Gln Trp Val Leu Thr Ala Ala His Cys Val Gly Pro
        35                  40                  45

Asp Val Lys Asp Leu Ala Ala Leu Arg Val Gln Leu Arg Glu Gln His
    50                  55                  60

Leu Tyr Tyr Gln Asp Gln Leu Leu Pro Val Ser Arg Ile Ile Val His
65                  70                  75                  80

Pro Gln Phe Tyr Thr Ala Gln Ile Gly Ala Asp Ile Ala Leu Leu Glu
                85                  90                  95

Leu Glu Glu Pro Val Lys Val Ser Ser His Val His Thr Val Thr Leu
            100                 105                 110

Pro Pro Ala Ser Glu Thr Phe Pro Pro Gly Met Pro Cys Trp Val Thr
        115                 120                 125

Gly Trp Gly Asp Val Asp Asn Asp Glu Arg Leu Pro Pro Pro Phe Pro
    130                 135                 140

Leu Lys Gln Val Lys Val Pro Ile Met Glu Asn His Ile Cys Asp Ala
145                 150                 155                 160

Lys Tyr His Leu Gly Ala Tyr Thr Gly Asp Asp Val Arg Ile Val Arg
                165                 170                 175
```

```
Asp Asp Met Leu Cys Ala Gly Asn Thr Arg Arg Asp Ser Cys Gln Gly
            180                 185                 190

Asp Ala Gly Gly Pro Leu Val Cys Lys Val Asn Gly Thr Trp Leu Gln
        195                 200                 205

Ala Gly Val Val Ser Trp Gly Glu Gly Cys Ala Gln Pro Asn Arg Pro
    210                 215                 220

Gly Ile Tyr Thr Arg Val Thr Tyr Tyr Leu Asp Trp Ile His His Tyr
225                 230                 235                 240

Val Pro Lys Lys Pro
            245

<210> SEQ ID NO 34
<211> LENGTH: 735
<212> TYPE: DNA
<213> ORGANISM: Homo sapiens
<220> FEATURE:
<221> NAME/KEY: CDS
<222> LOCATION: (1)..(735)

<400> SEQUENCE: 34
```

| | | | | | | | | | | | | | | | | |
|---|---|---|---|---|---|---|---|---|---|---|---|---|---|---|---|---|
| atc | gtc | ggg | ggt | cag | gag | gcc | ccc | agg | agc | aag | tgg | ccc | tgg | cag | gtg | 48 |
| Ile | Val | Gly | Gly | Gln | Glu | Ala | Pro | Arg | Ser | Lys | Trp | Pro | Trp | Gln | Val | |
| 1 | | | | 5 | | | | | 10 | | | | | 15 | | |

```
agc ctg aga gtc cac ggc cca tac tgg atg cac ttc tgc ggg ggc tcc    96
Ser Leu Arg Val His Gly Pro Tyr Trp Met His Phe Cys Gly Gly Ser
            20                  25                  30 ctc atc cac ccc cag tgg gtg ctg acc gca gcg cac tgc gtg gga ccg   144
Leu Ile His Pro Gln Trp Val Leu Thr Ala Ala His Cys Val Gly Pro
        35                  40                  45 gac gtc aag gat ctg gcc gcc ctc agg gtg caa ctg cgg gag cag cac   192
Asp Val Lys Asp Leu Ala Ala Leu Arg Val Gln Leu Arg Glu Gln His
    50                  55                  60 ctc tac tac cag gac cag ctg ctg ccg gtc agc agg atc atc gtg cac   240
Leu Tyr Tyr Gln Asp Gln Leu Leu Pro Val Ser Arg Ile Ile Val His
65                  70                  75                  80 cca cag ttc tac acc gcc cag atc gga gcg gac atc gcc ctg ctg gag   288
Pro Gln Phe Tyr Thr Ala Gln Ile Gly Ala Asp Ile Ala Leu Leu Glu
                85                  90                  95 ctg gag gag ccg gtg aag gtc tcc agc cac gtc cac acg gtc acc ctg   336
Leu Glu Glu Pro Val Lys Val Ser Ser His Val His Thr Val Thr Leu
            100                 105                 110 ccc cct gcc tca gag acc ttc ccc ccg ggg atg ccg tgc tgg gtc act   384
Pro Pro Ala Ser Glu Thr Phe Pro Pro Gly Met Pro Cys Trp Val Thr
        115                 120                 125 ggc tgg ggc gat gtg gac aat gat gag cgc ctc cca ccg cca ttt cct   432
Gly Trp Gly Asp Val Asp Asn Asp Glu Arg Leu Pro Pro Pro Phe Pro
    130                 135                 140 ctg aag cag gtg aag gtc ccc ata atg gaa aac cac att tgt gac gca   480
Leu Lys Gln Val Lys Val Pro Ile Met Glu Asn His Ile Cys Asp Ala
145                 150                 155                 160 aaa tac cac ctt ggc gcc tac acg gga gac gac gtc cgc atc gtc cgt   528
Lys Tyr His Leu Gly Ala Tyr Thr Gly Asp Asp Val Arg Ile Val Arg
                165                 170                 175 gac gac atg ctg tgt gcc ggg aac acc cgg agg gac tca tgc caa gga   576
Asp Asp Met Leu Cys Ala Gly Asn Thr Arg Arg Asp Ser Cys Gln Gly
            180                 185                 190 gac gcc ggc gga cca ctg gtg tgc aag gtg aat ggc acc tgg ctg cag   624
Asp Ala Gly Gly Pro Leu Val Cys Lys Val Asn Gly Thr Trp Leu Gln
        195                 200                 205
```

```
gcg ggc gtg gtc agc tgg ggc gag ggc tgt gcc cag ccc aac cgg cct      672
Ala Gly Val Val Ser Trp Gly Glu Gly Cys Ala Gln Pro Asn Arg Pro
    210             215                 220 ggc atc tac acc cgt gtc acc tac tac ttg gac tgg atc cac cac tat      720
Gly Ile Tyr Thr Arg Val Thr Tyr Tyr Leu Asp Trp Ile His His Tyr
225             230                 235                 240 gtc ccc aaa aag ccg                                                  735
Val Pro Lys Lys Pro
            245
```

<210> SEQ ID NO 35
<211> LENGTH: 245
<212> TYPE: PRT
<213> ORGANISM: Homo sapiens

<400> SEQUENCE: 35

```
Ile Val Gly Gly Gln Glu Ala Pro Arg Ser Lys Trp Pro Trp Gln Val
1               5                   10                  15

Ser Leu Arg Val His Gly Pro Tyr Trp Met His Phe Cys Gly Gly Ser
                20                  25                  30

Leu Ile His Pro Gln Trp Val Leu Thr Ala Ala His Cys Val Gly Pro
            35                  40                  45

Asp Val Lys Asp Leu Ala Ala Leu Arg Val Gln Leu Arg Glu Gln His
        50                  55                  60

Leu Tyr Tyr Gln Asp Gln Leu Leu Pro Val Ser Arg Ile Ile Val His
65                  70                  75                  80

Pro Gln Phe Tyr Thr Ala Gln Ile Gly Ala Asp Ile Ala Leu Leu Glu
                85                  90                  95

Leu Glu Glu Pro Val Lys Val Ser Ser His Val His Thr Val Thr Leu
            100                 105                 110

Pro Pro Ala Ser Glu Thr Phe Pro Pro Gly Met Pro Cys Trp Val Thr
        115                 120                 125

Gly Trp Gly Asp Val Asp Asn Asp Glu Arg Leu Pro Pro Phe Pro
130                 135                 140

Leu Lys Gln Val Lys Val Pro Ile Met Glu Asn His Ile Cys Asp Ala
145                 150                 155                 160

Lys Tyr His Leu Gly Ala Tyr Thr Gly Asp Asp Val Arg Ile Val Arg
                165                 170                 175

Asp Asp Met Leu Cys Ala Gly Asn Thr Arg Arg Asp Ser Cys Gln Gly
            180                 185                 190

Asp Ala Gly Gly Pro Leu Val Cys Lys Val Asn Gly Thr Trp Leu Gln
        195                 200                 205

Ala Gly Val Val Ser Trp Gly Glu Gly Cys Ala Gln Pro Asn Arg Pro
    210             215                 220

Gly Ile Tyr Thr Arg Val Thr Tyr Tyr Leu Asp Trp Ile His His Tyr
225             230                 235                 240

Val Pro Lys Lys Pro
            245
```

<210> SEQ ID NO 36
<211> LENGTH: 771
<212> TYPE: DNA
<213> ORGANISM: Homo sapiens
<220> FEATURE:
<221> NAME/KEY: CDS
<222> LOCATION: (7)..(753)

<400> SEQUENCE: 36

-continued

```
gggccc ctc gag aaa aga atc gtc ggg ggt cag gag gcc ccc agg agc         48
       Leu Glu Lys Arg Ile Val Gly Gly Gln Glu Ala Pro Arg Ser
       1               5                   10 aag tgg ccc tgg cag gtg agc ctg aga gtc cac ggc cca tac tgg atg        96
Lys Trp Pro Trp Gln Val Ser Leu Arg Val His Gly Pro Tyr Trp Met
15              20                  25                  30 cac ttc tgc ggg ggc tcc ctc atc cac ccc cag tgg gtg ctg acc gcc       144
His Phe Cys Gly Gly Ser Leu Ile His Pro Gln Trp Val Leu Thr Ala
                35                  40                  45 gcg gcg tgc gtg gga ccg gac gtc aag gat ctg gcc gcc ctc agg gtg       192
Ala Ala Cys Val Gly Pro Asp Val Lys Asp Leu Ala Ala Leu Arg Val
            50                  55                  60 caa ctg cgg gag cag cac ctc tac tac cag gac cag ctg ctg ccg gtc       240
Gln Leu Arg Glu Gln His Leu Tyr Tyr Gln Asp Gln Leu Leu Pro Val
65                  70                  75 agc agg atc atc gtg cac cca cag ttc tac acc gcc cag atc gga gcg       288
Ser Arg Ile Ile Val His Pro Gln Phe Tyr Thr Ala Gln Ile Gly Ala
        80                  85                  90 gac atc gcc ctg ctg gag ctg gag gag ccg gtg aac gtc tcc agc cac       336
Asp Ile Ala Leu Leu Glu Leu Glu Glu Pro Val Asn Val Ser Ser His
95                  100                 105                 110 gtc cac acg gtc acc ctg ccc cct gcc tca gag acc ttc ccc ccg ggg       384
Val His Thr Val Thr Leu Pro Pro Ala Ser Glu Thr Phe Pro Pro Gly
                115                 120                 125 atg ccg tgc tgg gtc act ggc tgg ggc gat gtg gac aat gat gag cgc       432
Met Pro Cys Trp Val Thr Gly Trp Gly Asp Val Asp Asn Asp Glu Arg
            130                 135                 140 ctc cca ccg cca ttt cct ctg aag cag gtg aag gtc ccc ata atg gaa       480
Leu Pro Pro Pro Phe Pro Leu Lys Gln Val Lys Val Pro Ile Met Glu
        145                 150                 155 aac cac att tgt gac gca aaa tac cac ctt ggc gcc tac acg gga gac       528
Asn His Ile Cys Asp Ala Lys Tyr His Leu Gly Ala Tyr Thr Gly Asp
160                 165                 170 gac gtc cgc atc gtc cgt gac gac atg ctg tgt gcc ggg aac acc cgg       576
Asp Val Arg Ile Val Arg Asp Asp Met Leu Cys Ala Gly Asn Thr Arg
175                 180                 185                 190 agg gac tca tgc cag ggc gac tcc gga ggg ccc ctg gtg tgc aag gtg       624
Arg Asp Ser Cys Gln Gly Asp Ser Gly Gly Pro Leu Val Cys Lys Val
                195                 200                 205 aat ggc acc tgg ctg cag gcg ggc gtg gtc agc tgg ggc gag ggc tgt       672
Asn Gly Thr Trp Leu Gln Ala Gly Val Val Ser Trp Gly Glu Gly Cys
            210                 215                 220 gcc cag ccc aac cgg cct ggc atc tac acc cgt gtc acc tac tac ttg       720
Ala Gln Pro Asn Arg Pro Gly Ile Tyr Thr Arg Val Thr Tyr Tyr Leu
        225                 230                 235 gac tgg atc cac cac tat gtc ccc aaa aag ccg tgaagcggcc gccgtcgt      771
Asp Trp Ile His His Tyr Val Pro Lys Lys Pro
240                 245

<210> SEQ ID NO 37
<211> LENGTH: 249
<212> TYPE: PRT
<213> ORGANISM: Homo sapiens

<400> SEQUENCE: 37

Leu Glu Lys Arg Ile Val Gly Gly Gln Glu Ala Pro Arg Ser Lys Trp
1               5                   10                  15

Pro Trp Gln Val Ser Leu Arg Val His Gly Pro Tyr Trp Met His Phe
                20                  25                  30

Cys Gly Gly Ser Leu Ile His Pro Gln Trp Val Leu Thr Ala Ala Ala
```

-continued

```
                35                  40                  45
Cys Val Gly Pro Asp Val Lys Asp Leu Ala Ala Leu Arg Val Gln Leu
 50                  55                  60

Arg Glu Gln His Leu Tyr Tyr Gln Asp Gln Leu Leu Pro Val Ser Arg
 65                  70                  75                  80

Ile Ile Val His Pro Gln Phe Tyr Thr Ala Gln Ile Gly Ala Asp Ile
                 85                  90                  95

Ala Leu Leu Glu Leu Glu Glu Pro Val Asn Val Ser Ser His Val His
            100                 105                 110

Thr Val Thr Leu Pro Pro Ala Ser Glu Thr Phe Pro Pro Gly Met Pro
        115                 120                 125

Cys Trp Val Thr Gly Trp Gly Asp Val Asp Asn Asp Glu Arg Leu Pro
130                 135                 140

Pro Pro Phe Pro Leu Lys Gln Val Lys Val Pro Ile Met Glu Asn His
145                 150                 155                 160

Ile Cys Asp Ala Lys Tyr His Leu Gly Ala Tyr Thr Gly Asp Asp Val
                165                 170                 175

Arg Ile Val Arg Asp Asp Met Leu Cys Ala Gly Asn Thr Arg Arg Asp
            180                 185                 190

Ser Cys Gln Gly Asp Ser Gly Gly Pro Leu Val Cys Lys Val Asn Gly
        195                 200                 205

Thr Trp Leu Gln Ala Gly Val Val Ser Trp Gly Glu Gly Cys Ala Gln
210                 215                 220

Pro Asn Arg Pro Gly Ile Tyr Thr Arg Val Thr Tyr Tyr Leu Asp Trp
225                 230                 235                 240

Ile His His Tyr Val Pro Lys Lys Pro
                245

<210> SEQ ID NO 38
<211> LENGTH: 771
<212> TYPE: DNA
<213> ORGANISM: Homo sapiens
<220> FEATURE:
<221> NAME/KEY: CDS
<222> LOCATION: (7)..(753)

<400> SEQUENCE: 38 gggccc ctc gag aaa aga atc gtc ggg ggt cag gag gcc ccc agg agc      48
       Leu Glu Lys Arg Ile Val Gly Gly Gln Glu Ala Pro Arg Ser
        1               5                  10 aag tgg ccc tgg cag gtg agc ctg aga gtc cac ggc cca tac tgg atg    96
Lys Trp Pro Trp Gln Val Ser Leu Arg Val His Gly Pro Tyr Trp Met
 15                  20                  25                  30 cac ttc tgc ggg ggc tcc ctc atc cac ccc cag tgg gtg ctg acc gca   144
His Phe Cys Gly Gly Ser Leu Ile His Pro Gln Trp Val Leu Thr Ala
                 35                  40                  45 gcg cac tgc gtg gga ccg gac gtc aag gat ctg gcc gcc ctc agg gtg   192
Ala His Cys Val Gly Pro Asp Val Lys Asp Leu Ala Ala Leu Arg Val
             50                  55                  60 caa ctg cgg gag cag cac ctc tac tac cag gac cag ctg ctg ccg gtc   240
Gln Leu Arg Glu Gln His Leu Tyr Tyr Gln Asp Gln Leu Leu Pro Val
 65                  70                  75 agc agg atc atc gtg cac cca cag ttc tac acc gcc cag atc gga gcg   288
Ser Arg Ile Ile Val His Pro Gln Phe Tyr Thr Ala Gln Ile Gly Ala
             80                  85                  90 gca atc gcc ctg ctg gag ctg gag gag ccg gtg aac gtc tcc agc cac   336
Ala Ile Ala Leu Leu Glu Leu Glu Glu Pro Val Asn Val Ser Ser His
 95                 100                 105                 110
```

```
gtc cac acg gtc acc ctg ccc cct gcc tca gag acc ttc ccc ccg ggg      384
Val His Thr Val Thr Leu Pro Pro Ala Ser Glu Thr Phe Pro Pro Gly
            115                 120                 125 atg ccg tgc tgg gtc act ggc tgg ggc gat gtg gac aat gat gag cgc      432
Met Pro Cys Trp Val Thr Gly Trp Gly Asp Val Asp Asn Asp Glu Arg
    130                 135                 140 ctc cca ccg cca ttt cct ctg aag cag gtg aag gtc ccc ata atg gaa      480
Leu Pro Pro Pro Phe Pro Leu Lys Gln Val Lys Val Pro Ile Met Glu
        145                 150                 155 aac cac att tgt gac gca aaa tac cac ctt ggc gcc tac acg gga gac      528
Asn His Ile Cys Asp Ala Lys Tyr His Leu Gly Ala Tyr Thr Gly Asp
160                 165                 170 gac gtc cgc atc gtc cgt gac gac atg ctg tgt gcc ggg aac acc cgg      576
Asp Val Arg Ile Val Arg Asp Asp Met Leu Cys Ala Gly Asn Thr Arg
175                 180                 185                 190 agg gac tca tgc cag ggc gac tcc gga ggg ccc ctg gtg tgc aag gtg      624
Arg Asp Ser Cys Gln Gly Asp Ser Gly Gly Pro Leu Val Cys Lys Val
                195                 200                 205 aat ggc acc tgg ctg cag gcg ggc gtg gtc agc tgg ggc gag ggc tgt      672
Asn Gly Thr Trp Leu Gln Ala Gly Val Val Ser Trp Gly Glu Gly Cys
            210                 215                 220 gcc cag ccc aac cgg cct ggc atc tac acc cgt gtc acc tac tac ttg      720
Ala Gln Pro Asn Arg Pro Gly Ile Tyr Thr Arg Val Thr Tyr Tyr Leu
    225                 230                 235 gac tgg atc cac cac tat gtc ccc aaa aag ccg tgaagcggcc gccgtcgt      771
Asp Trp Ile His His Tyr Val Pro Lys Lys Pro
        240                 245

<210> SEQ ID NO 39
<211> LENGTH: 249
<212> TYPE: PRT
<213> ORGANISM: Homo sapiens

<400> SEQUENCE: 39

Leu Glu Lys Arg Ile Val Gly Gly Gln Glu Ala Pro Arg Ser Lys Trp
1               5                   10                  15

Pro Trp Gln Val Ser Leu Arg Val His Gly Pro Tyr Trp Met His Phe
            20                  25                  30

Cys Gly Gly Ser Leu Ile His Pro Gln Trp Val Leu Thr Ala Ala His
        35                  40                  45

Cys Val Gly Pro Asp Val Lys Asp Leu Ala Ala Leu Arg Val Gln Leu
    50                  55                  60

Arg Glu Gln His Leu Tyr Tyr Gln Asp Gln Leu Leu Pro Val Ser Arg
65                  70                  75                  80

Ile Ile Val His Pro Gln Phe Tyr Thr Ala Gln Ile Gly Ala Ala Ile
                85                  90                  95

Ala Leu Leu Glu Leu Glu Glu Pro Val Asn Val Ser Ser His Val His
            100                 105                 110

Thr Val Thr Leu Pro Pro Ala Ser Glu Thr Phe Pro Pro Gly Met Pro
        115                 120                 125

Cys Trp Val Thr Gly Trp Gly Asp Val Asp Asn Asp Glu Arg Leu Pro
    130                 135                 140

Pro Pro Phe Pro Leu Lys Gln Val Lys Val Pro Ile Met Glu Asn His
145                 150                 155                 160

Ile Cys Asp Ala Lys Tyr His Leu Gly Ala Tyr Thr Gly Asp Asp Val
                165                 170                 175

Arg Ile Val Arg Asp Asp Met Leu Cys Ala Gly Asn Thr Arg Arg Asp
```

-continued

```
                180                 185                 190
Ser Cys Gln Gly Asp Ser Gly Gly Pro Leu Val Cys Lys Val Asn Gly
            195                 200                 205

Thr Trp Leu Gln Ala Gly Val Val Ser Trp Gly Glu Gly Cys Ala Gln
        210                 215                 220

Pro Asn Arg Pro Gly Ile Tyr Thr Arg Val Thr Tyr Leu Asp Trp
225                 230                 235                 240

Ile His His Tyr Val Pro Lys Lys Pro
                245

<210> SEQ ID NO 40
<211> LENGTH: 771
<212> TYPE: DNA
<213> ORGANISM: Homo sapiens
<220> FEATURE:
<221> NAME/KEY: CDS
<222> LOCATION: (7)..(753)

<400> SEQUENCE: 40 gggccc ctc gag aaa aga atc gtc ggg ggt cag gag gcc ccc agg agc       48
       Leu Glu Lys Arg Ile Val Gly Gly Gln Glu Ala Pro Arg Ser
       1               5                   10 aag tgg ccc tgg cag gtg agc ctg aga gtc cac ggc cca tac tgg atg    96
Lys Trp Pro Trp Gln Val Ser Leu Arg Val His Gly Pro Tyr Trp Met
15              20                  25                  30 cac ttc tgc ggg ggc tcc ctc atc cac ccc cag tgg gtg ctg acc gca   144
His Phe Cys Gly Gly Ser Leu Ile His Pro Gln Trp Val Leu Thr Ala
                35                  40                  45 gcg cac tgc gtg gga ccg gac gtc aag gat ctg gcc gcc ctc agg gtg   192
Ala His Cys Val Gly Pro Asp Val Lys Asp Leu Ala Ala Leu Arg Val
            50                  55                  60 caa ctg cgg gag cag cac ctc tac tac cag gac cag ctg ctg ccg gtc   240
Gln Leu Arg Glu Gln His Leu Tyr Tyr Gln Asp Gln Leu Leu Pro Val
        65                  70                  75 agc agg atc atc gtg cac cca cag ttc tac acc gcc cag atc gga gcg   288
Ser Arg Ile Ile Val His Pro Gln Phe Tyr Thr Ala Gln Ile Gly Ala
    80                  85                  90 gac atc gcc ctg ctg gag ctg gag gag ccg gtg aac gtc tcc agc cac   336
Asp Ile Ala Leu Leu Glu Leu Glu Glu Pro Val Asn Val Ser Ser His
95                  100                 105                 110 gtc cac acg gtc acc ctg ccc cct gcc tca gag acc ttc ccc ccg ggg   384
Val His Thr Val Thr Leu Pro Pro Ala Ser Glu Thr Phe Pro Pro Gly
                115                 120                 125 atg ccg tgc tgg gtc act ggc tgg ggc gat gtg gac aat gat gag cgc   432
Met Pro Cys Trp Val Thr Gly Trp Gly Asp Val Asp Asn Asp Glu Arg
            130                 135                 140 ctc cca ccg cca ttt cct ctg aag cag gtg aag gtc ccc ata atg gaa   480
Leu Pro Pro Pro Phe Pro Leu Lys Gln Val Lys Val Pro Ile Met Glu
        145                 150                 155 aac cac att tgt gac gca aaa tac cac ctt ggc gcc tac acg gga gac   528
Asn His Ile Cys Asp Ala Lys Tyr His Leu Gly Ala Tyr Thr Gly Asp
    160                 165                 170 gac gtc cgc atc gtc cgt gac gac atg ctg tgt gcc ggg aac acc cgg   576
Asp Val Arg Ile Val Arg Asp Asp Met Leu Cys Ala Gly Asn Thr Arg
175                 180                 185                 190 agg gac tca tgt caa ggc gac gcc ggc gga cct ctg gtg tgc aag gtg   624
Arg Asp Ser Cys Gln Gly Asp Ala Gly Gly Pro Leu Val Cys Lys Val
                195                 200                 205 aat ggc acc tgg ctg cag gcg ggc gtg gtc agc tgg ggc gag ggc tgt   672
Asn Gly Thr Trp Leu Gln Ala Gly Val Val Ser Trp Gly Glu Gly Cys
```

```
                    210                 215                 220
gcc cag ccc aac cgg cct ggc atc tac acc cgt gtc acc tac tac ttg        720
Ala Gln Pro Asn Arg Pro Gly Ile Tyr Thr Arg Val Thr Tyr Tyr Leu
            225                 230                 235 gac tgg atc cac cac tat gtc ccc aaa aag ccg tgaagcggcc gccgtcgt        771
Asp Trp Ile His His Tyr Val Pro Lys Lys Pro
    240                 245
```

<210> SEQ ID NO 41
<211> LENGTH: 249
<212> TYPE: PRT
<213> ORGANISM: Homo sapiens

<400> SEQUENCE: 41

```
Leu Glu Lys Arg Ile Val Gly Gly Gln Glu Ala Pro Arg Ser Lys Trp
1               5                   10                  15

Pro Trp Gln Val Ser Leu Arg Val His Gly Pro Tyr Trp Met His Phe
            20                  25                  30

Cys Gly Gly Ser Leu Ile His Pro Gln Trp Val Leu Thr Ala Ala His
        35                  40                  45

Cys Val Gly Pro Asp Val Lys Asp Leu Ala Ala Leu Arg Val Gln Leu
    50                  55                  60

Arg Glu Gln His Leu Tyr Tyr Gln Asp Gln Leu Leu Pro Val Ser Arg
65                  70                  75                  80

Ile Ile Val His Pro Gln Phe Tyr Thr Ala Gln Ile Gly Ala Asp Ile
                85                  90                  95

Ala Leu Leu Glu Leu Glu Glu Pro Val Asn Val Ser Ser His Val His
            100                 105                 110

Thr Val Thr Leu Pro Pro Ala Ser Glu Thr Phe Pro Pro Gly Met Pro
        115                 120                 125

Cys Trp Val Thr Gly Trp Gly Asp Val Asp Asn Asp Glu Arg Leu Pro
    130                 135                 140

Pro Pro Phe Pro Leu Lys Gln Val Lys Val Pro Ile Met Glu Asn His
145                 150                 155                 160

Ile Cys Asp Ala Lys Tyr His Leu Gly Ala Tyr Thr Gly Asp Asp Val
                165                 170                 175

Arg Ile Val Arg Asp Asp Met Leu Cys Ala Gly Asn Thr Arg Arg Asp
            180                 185                 190

Ser Cys Gln Gly Asp Ala Gly Gly Pro Leu Val Cys Lys Val Asn Gly
        195                 200                 205

Thr Trp Leu Gln Ala Gly Val Val Ser Trp Gly Glu Gly Cys Ala Gln
    210                 215                 220

Pro Asn Arg Pro Gly Ile Tyr Thr Arg Val Thr Tyr Tyr Leu Asp Trp
225                 230                 235                 240

Ile His His Tyr Val Pro Lys Lys Pro
                245
```

<210> SEQ ID NO 42
<211> LENGTH: 771
<212> TYPE: DNA
<213> ORGANISM: Homo sapiens
<220> FEATURE:
<221> NAME/KEY: CDS
<222> LOCATION: (7)..(753)

<400> SEQUENCE: 42

```
gggccc ctc gag aaa aga atc gtc ggg ggt cag gag gcc ccc agg agc         48
       Leu Glu Lys Arg Ile Val Gly Gly Gln Glu Ala Pro Arg Ser
```

```
                    1               5                   10
aag tgg ccc tgg cag gtg agc ctg aga gtc cac ggc cca tac tgg atg        96
Lys Trp Pro Trp Gln Val Ser Leu Arg Val His Gly Pro Tyr Trp Met
 15                  20                  25                  30 cac ttc tgc ggg ggc tcc ctc atc cac ccc cag tgg gtg ctg acc gca       144
His Phe Cys Gly Gly Ser Leu Ile His Pro Gln Trp Val Leu Thr Ala
                 35                  40                  45 gcg cac tgc gtg gga ccg gac gtc aag gat ctg gcc gcc ctc agg gtg       192
Ala His Cys Val Gly Pro Asp Val Lys Asp Leu Ala Ala Leu Arg Val
             50                  55                  60 caa ctg cgg gag cag cac ctc tac tac cag gac cag ctg ctg ccg gtc       240
Gln Leu Arg Glu Gln His Leu Tyr Tyr Gln Asp Gln Leu Leu Pro Val
         65                  70                  75 agc agg atc atc gtg cac cca cag ttc tac acc gcc cag atc gga gcg       288
Ser Arg Ile Ile Val His Pro Gln Phe Tyr Thr Ala Gln Ile Gly Ala
     80                  85                  90 gac atc gcc ctg ctg gag ctg gag gag ccg gtg aac gtc tcc agc cac       336
Asp Ile Ala Leu Leu Glu Leu Glu Glu Pro Val Asn Val Ser Ser His
 95                 100                 105                 110 gtc cac acg gtc acc ctg ccc cct gcc tca gag acc ttc ccc ccg ggg       384
Val His Thr Val Thr Leu Pro Pro Ala Ser Glu Thr Phe Pro Pro Gly
                115                 120                 125 atg ccg tgc tgg gtc act ggc tgg ggc gat gtg gac aat gat gag cgc       432
Met Pro Cys Trp Val Thr Gly Trp Gly Asp Val Asp Asn Asp Glu Arg
            130                 135                 140 ctc cca ccg cca ttt cct ctg aag cag gtg aag gtc ccc ata atg gaa       480
Leu Pro Pro Pro Phe Pro Leu Lys Gln Val Lys Val Pro Ile Met Glu
        145                 150                 155 aac cac att tgt gac gca aaa tac cac ctt ggc gcc tac acg gga gac       528
Asn His Ile Cys Asp Ala Lys Tyr His Leu Gly Ala Tyr Thr Gly Asp
    160                 165                 170 gac gtc cgc atc gtc cgt gac gac atg ctg tgt gcc ggg aac acc cgg       576
Asp Val Arg Ile Val Arg Asp Asp Met Leu Cys Ala Gly Asn Thr Arg
175                 180                 185                 190 agg gac tca tgc caa gga gac gcc ggc gga cca ctg gtg tgc aag gtg       624
Arg Asp Ser Cys Gln Gly Asp Ala Gly Gly Pro Leu Val Cys Lys Val
                195                 200                 205 aat ggc acc tgg ctg cag gcg ggc gtg gtc agc tgg ggc gag ggc tgt       672
Asn Gly Thr Trp Leu Gln Ala Gly Val Val Ser Trp Gly Glu Gly Cys
            210                 215                 220 gcc cag ccc aac cgg cct ggc atc tac acc cgt gtc acc tac tac ttg       720
Ala Gln Pro Asn Arg Pro Gly Ile Tyr Thr Arg Val Thr Tyr Tyr Leu
        225                 230                 235 gac tgg atc cac cac tat gtc ccc aaa aag ccg tgaagcggcc gccgtcgt      771
Asp Trp Ile His His Tyr Val Pro Lys Lys Pro
    240                 245
```

<210> SEQ ID NO 43
<211> LENGTH: 249
<212> TYPE: PRT
<213> ORGANISM: Homo sapiens

<400> SEQUENCE: 43

```
Leu Glu Lys Arg Ile Val Gly Gly Gln Glu Ala Pro Arg Ser Lys Trp
 1               5                  10                  15

Pro Trp Gln Val Ser Leu Arg Val His Gly Pro Tyr Trp Met His Phe
                20                  25                  30

Cys Gly Gly Ser Leu Ile His Pro Gln Trp Val Leu Thr Ala Ala His
            35                  40                  45
```

-continued

```
Cys Val Gly Pro Asp Val Lys Asp Leu Ala Ala Leu Arg Val Gln Leu
 50                  55                  60

Arg Glu Gln His Leu Tyr Tyr Gln Asp Gln Leu Leu Pro Val Ser Arg
 65                  70                  75                  80

Ile Ile Val His Pro Gln Phe Tyr Thr Ala Gln Ile Gly Ala Asp Ile
                 85                  90                  95

Ala Leu Leu Glu Leu Glu Glu Pro Val Asn Val Ser Ser His Val His
                100                 105                 110

Thr Val Thr Leu Pro Pro Ala Ser Glu Thr Phe Pro Pro Gly Met Pro
            115                 120                 125

Cys Trp Val Thr Gly Trp Gly Asp Val Asp Asn Asp Glu Arg Leu Pro
130                 135                 140

Pro Pro Phe Pro Leu Lys Gln Val Lys Val Pro Ile Met Glu Asn His
145                 150                 155                 160

Ile Cys Asp Ala Lys Tyr His Leu Gly Ala Tyr Thr Gly Asp Asp Val
                165                 170                 175

Arg Ile Val Arg Asp Asp Met Leu Cys Ala Gly Asn Thr Arg Arg Asp
                180                 185                 190

Ser Cys Gln Gly Asp Ala Gly Gly Pro Leu Val Cys Lys Val Asn Gly
            195                 200                 205

Thr Trp Leu Gln Ala Gly Val Val Ser Trp Gly Glu Gly Cys Ala Gln
210                 215                 220

Pro Asn Arg Pro Gly Ile Tyr Thr Arg Val Thr Tyr Tyr Leu Asp Trp
225                 230                 235                 240

Ile His His Tyr Val Pro Lys Lys Pro
                245
```

```
<210> SEQ ID NO 44
<211> LENGTH: 735
<212> TYPE: DNA
<213> ORGANISM: Homo sapiens
<220> FEATURE:
<221> NAME/KEY: CDS
<222> LOCATION: (1)..(735)

<400> SEQUENCE: 44 atc gtc ggg ggt cag gag gcc ccc agg agc aag tgg ccc tgg cag gtg     48
Ile Val Gly Gly Gln Glu Ala Pro Arg Ser Lys Trp Pro Trp Gln Val
 1               5                  10                  15 agc ctg aga gtc cac ggc cca tac tgg atg cac ttc tgc ggg ggc tcc     96
Ser Leu Arg Val His Gly Pro Tyr Trp Met His Phe Cys Gly Gly Ser
                 20                  25                  30 ctc atc cac ccc cag tgg gtg ctg acc gcc gcg gcg tgc gtg gga ccg    144
Leu Ile His Pro Gln Trp Val Leu Thr Ala Ala Ala Cys Val Gly Pro
             35                  40                  45 gac gtc aag gat ctg gcc gcc ctc agg gtg caa ctg cgg gag cag cac    192
Asp Val Lys Asp Leu Ala Ala Leu Arg Val Gln Leu Arg Glu Gln His
 50                  55                  60 ctc tac tac cag gac cag ctg ctg ccg gtc agc agg atc atc gtg cac    240
Leu Tyr Tyr Gln Asp Gln Leu Leu Pro Val Ser Arg Ile Ile Val His
 65                  70                  75                  80 cca cag ttc tac acc gcc cag atc gga gcg gac atc gcc ctg ctg gag    288
Pro Gln Phe Tyr Thr Ala Gln Ile Gly Ala Asp Ile Ala Leu Leu Glu
                 85                  90                  95 ctg gag gag ccg gtg aac gtc tcc agc cac gtc cac acg gtc acc ctg    336
Leu Glu Glu Pro Val Asn Val Ser Ser His Val His Thr Val Thr Leu
                100                 105                 110 ccc cct gcc tca gag acc ttc ccc ccg ggg atg ccg tgc tgg gtc act    384
```

```

Pro Pro Ala Ser Glu Thr Phe Pro Pro Gly Met Pro Cys Trp Val Thr
        115                 120                 125 ggc tgg ggc gat gtg gac aat gat gag cgc ctc cca ccg cca ttt cct        432
Gly Trp Gly Asp Val Asp Asn Asp Glu Arg Leu Pro Pro Pro Phe Pro
130                 135                 140 ctg aag cag gtg aag gtc ccc ata atg gaa aac cac att tgt gac gca        480
Leu Lys Gln Val Lys Val Pro Ile Met Glu Asn His Ile Cys Asp Ala
145                 150                 155                 160 aaa tac cac ctt ggc gcc tac acg gga gac gac gtc cgc atc gtc cgt        528
Lys Tyr His Leu Gly Ala Tyr Thr Gly Asp Asp Val Arg Ile Val Arg
            165                 170                 175 gac gac atg ctg tgt gcc ggg aac acc cgg agg gac tca tgc cag ggc        576
Asp Asp Met Leu Cys Ala Gly Asn Thr Arg Arg Asp Ser Cys Gln Gly
        180                 185                 190 gac tcc gga ggg ccc ctg gtg tgc aag gtg aat ggc acc tgg ctg cag        624
Asp Ser Gly Gly Pro Leu Val Cys Lys Val Asn Gly Thr Trp Leu Gln
    195                 200                 205 gcg ggc gtg gtc agc tgg ggc gag ggc tgt gcc cag ccc aac cgg cct        672
Ala Gly Val Val Ser Trp Gly Glu Gly Cys Ala Gln Pro Asn Arg Pro
210                 215                 220 ggc atc tac acc cgt gtc acc tac tac ttg gac tgg atc cac cac tat        720
Gly Ile Tyr Thr Arg Val Thr Tyr Tyr Leu Asp Trp Ile His His Tyr
225                 230                 235                 240 gtc ccc aaa aag ccg                                                    735
Val Pro Lys Lys Pro
            245

<210> SEQ ID NO 45
<211> LENGTH: 245
<212> TYPE: PRT
<213> ORGANISM: Homo sapiens

<400> SEQUENCE: 45

Ile Val Gly Gly Gln Glu Ala Pro Arg Ser Lys Trp Pro Trp Gln Val
1               5                   10                  15

Ser Leu Arg Val His Gly Pro Tyr Trp Met His Phe Cys Gly Gly Ser
            20                  25                  30

Leu Ile His Pro Gln Trp Val Leu Thr Ala Ala Ala Cys Val Gly Pro
        35                  40                  45

Asp Val Lys Asp Leu Ala Ala Leu Arg Val Gln Leu Arg Glu Gln His
    50                  55                  60

Leu Tyr Tyr Gln Asp Gln Leu Leu Pro Val Ser Arg Ile Ile Val His
65                  70                  75                  80

Pro Gln Phe Tyr Thr Ala Gln Ile Gly Ala Asp Ile Ala Leu Leu Glu
                85                  90                  95

Leu Glu Glu Pro Val Asn Val Ser Ser His Val His Thr Val Thr Leu
            100                 105                 110

Pro Pro Ala Ser Glu Thr Phe Pro Pro Gly Met Pro Cys Trp Val Thr
        115                 120                 125

Gly Trp Gly Asp Val Asp Asn Asp Glu Arg Leu Pro Pro Pro Phe Pro
130                 135                 140

Leu Lys Gln Val Lys Val Pro Ile Met Glu Asn His Ile Cys Asp Ala
145                 150                 155                 160

Lys Tyr His Leu Gly Ala Tyr Thr Gly Asp Asp Val Arg Ile Val Arg
                165                 170                 175

Asp Asp Met Leu Cys Ala Gly Asn Thr Arg Arg Asp Ser Cys Gln Gly
            180                 185                 190
```

```
Asp Ser Gly Gly Pro Leu Val Cys Lys Val Asn Gly Thr Trp Leu Gln
        195                 200                 205

Ala Gly Val Val Ser Trp Gly Glu Gly Cys Ala Gln Pro Asn Arg Pro
    210                 215                 220

Gly Ile Tyr Thr Arg Val Thr Tyr Tyr Leu Asp Trp Ile His His Tyr
225                 230                 235                 240

Val Pro Lys Lys Pro
                245

<210> SEQ ID NO 46
<211> LENGTH: 735
<212> TYPE: DNA
<213> ORGANISM: Homo sapiens
<220> FEATURE:
<221> NAME/KEY: CDS
<222> LOCATION: (1)..(735)

<400> SEQUENCE: 46 atc gtc ggg ggt cag gag gcc ccc agg agc aag tgg ccc tgg cag gtg        48
Ile Val Gly Gly Gln Glu Ala Pro Arg Ser Lys Trp Pro Trp Gln Val
1               5                   10                  15 agc ctg aga gtc cac ggc cca tac tgg atg cac ttc tgc ggg ggc tcc        96
Ser Leu Arg Val His Gly Pro Tyr Trp Met His Phe Cys Gly Gly Ser
            20                  25                  30 ctc atc cac ccc cag tgg gtg ctg acc gca gcg cac tgc gtg gga ccg       144
Leu Ile His Pro Gln Trp Val Leu Thr Ala Ala His Cys Val Gly Pro
        35                  40                  45 gac gtc aag gat ctg gcc gcc ctc agg gtg caa ctg cgg gag cag cac       192
Asp Val Lys Asp Leu Ala Ala Leu Arg Val Gln Leu Arg Glu Gln His
    50                  55                  60 ctc tac tac cag gac cag ctg ctg ccg gtc agc agg atc atc gtg cac       240
Leu Tyr Tyr Gln Asp Gln Leu Leu Pro Val Ser Arg Ile Ile Val His
65                  70                  75                  80 cca cag ttc tac acc gcc cag atc gga gcg gca atc gcc ctg ctg gag       288
Pro Gln Phe Tyr Thr Ala Gln Ile Gly Ala Ala Ile Ala Leu Leu Glu
                85                  90                  95 ctg gag gag ccg gtg aac gtc tcc agc cac gtc cac acg gtc acc ctg       336
Leu Glu Glu Pro Val Asn Val Ser Ser His Val His Thr Val Thr Leu
            100                 105                 110 ccc cct gcc tca gag acc ttc ccc ccg ggg atg ccg tgc tgg gtc act       384
Pro Pro Ala Ser Glu Thr Phe Pro Pro Gly Met Pro Cys Trp Val Thr
        115                 120                 125 ggc tgg ggc gat gtg gac aat gat gag cgc ctc cca ccg cca ttt cct       432
Gly Trp Gly Asp Val Asp Asn Asp Glu Arg Leu Pro Pro Pro Phe Pro
    130                 135                 140 ctg aag cag gtg aag gtc ccc ata atg gaa aac cac att tgt gac gca       480
Leu Lys Gln Val Lys Val Pro Ile Met Glu Asn His Ile Cys Asp Ala
145                 150                 155                 160 aaa tac cac ctt ggc gcc tac acg gga gac gac gtc cgc atc gtc cgt       528
Lys Tyr His Leu Gly Ala Tyr Thr Gly Asp Asp Val Arg Ile Val Arg
                165                 170                 175 gac gac atg ctg tgt gcc ggg aac acc cgg agg gac tca tgc cag ggc       576
Asp Asp Met Leu Cys Ala Gly Asn Thr Arg Arg Asp Ser Cys Gln Gly
            180                 185                 190 gac tcc gga ggg ccc ctg gtg tgc aag gtg aat ggc acc tgg ctg cag       624
Asp Ser Gly Gly Pro Leu Val Cys Lys Val Asn Gly Thr Trp Leu Gln
        195                 200                 205 gcg ggc gtg gtc agc tgg ggc gag ggc tgt gcc cag ccc aac cgg cct       672
Ala Gly Val Val Ser Trp Gly Glu Gly Cys Ala Gln Pro Asn Arg Pro
    210                 215                 220
```

```
ggc atc tac acc cgt gtc acc tac tac ttg gac tgg atc cac cac tat    720
Gly Ile Tyr Thr Arg Val Thr Tyr Tyr Leu Asp Trp Ile His His Tyr
225                 230                 235                 240 gtc ccc aaa aag ccg                                                735
Val Pro Lys Lys Pro
            245
```

<210> SEQ ID NO 47
<211> LENGTH: 245
<212> TYPE: PRT
<213> ORGANISM: Homo sapiens

<400> SEQUENCE: 47

```
Ile Val Gly Gly Gln Glu Ala Pro Arg Ser Lys Trp Pro Trp Gln Val
1               5                   10                  15

Ser Leu Arg Val His Gly Pro Tyr Trp Met His Phe Cys Gly Gly Ser
                20                  25                  30

Leu Ile His Pro Gln Trp Val Leu Thr Ala Ala His Cys Val Gly Pro
            35                  40                  45

Asp Val Lys Asp Leu Ala Ala Leu Arg Val Gln Leu Arg Glu Gln His
        50                  55                  60

Leu Tyr Tyr Gln Asp Gln Leu Leu Pro Val Ser Arg Ile Ile Val His
65                  70                  75                  80

Pro Gln Phe Tyr Thr Ala Gln Ile Gly Ala Ala Ile Ala Leu Leu Glu
                85                  90                  95

Leu Glu Glu Pro Val Asn Val Ser Ser His Val His Thr Val Thr Leu
            100                 105                 110

Pro Pro Ala Ser Glu Thr Phe Pro Pro Gly Met Pro Cys Trp Val Thr
        115                 120                 125

Gly Trp Gly Asp Val Asp Asn Asp Glu Arg Leu Pro Pro Pro Phe Pro
130                 135                 140

Leu Lys Gln Val Lys Val Pro Ile Met Glu Asn His Ile Cys Asp Ala
145                 150                 155                 160

Lys Tyr His Leu Gly Ala Tyr Thr Gly Asp Asp Val Arg Ile Val Arg
                165                 170                 175

Asp Asp Met Leu Cys Ala Gly Asn Thr Arg Arg Asp Ser Cys Gln Gly
            180                 185                 190

Asp Ser Gly Gly Pro Leu Val Cys Lys Val Asn Gly Thr Trp Leu Gln
        195                 200                 205

Ala Gly Val Val Ser Trp Gly Glu Gly Cys Ala Gln Pro Asn Arg Pro
210                 215                 220

Gly Ile Tyr Thr Arg Val Thr Tyr Tyr Leu Asp Trp Ile His His Tyr
225                 230                 235                 240

Val Pro Lys Lys Pro
            245
```

<210> SEQ ID NO 48
<211> LENGTH: 735
<212> TYPE: DNA
<213> ORGANISM: Homo sapiens
<220> FEATURE:
<221> NAME/KEY: CDS
<222> LOCATION: (1)..(735)

<400> SEQUENCE: 48

```
atc gtc ggg ggt cag gag gcc ccc agg agc aag tgg ccc tgg cag gtg    48
Ile Val Gly Gly Gln Glu Ala Pro Arg Ser Lys Trp Pro Trp Gln Val
1               5                   10                  15
```

-continued

| | |
|---|---|
| agc ctg aga gtc cac ggc cca tac tgg atg cac ttc tgc ggg ggc tcc<br>Ser Leu Arg Val His Gly Pro Tyr Trp Met His Phe Cys Gly Gly Ser<br>20                  25                  30 | 96 |
| ctc atc cac ccc cag tgg gtg ctg acc gca gcg cac tgc gtg gga ccg<br>Leu Ile His Pro Gln Trp Val Leu Thr Ala Ala His Cys Val Gly Pro<br>    35                  40                  45 | 144 |
| gac gtc aag gat ctg gcc gcc ctc agg gtg caa ctg cgg gag cag cac<br>Asp Val Lys Asp Leu Ala Ala Leu Arg Val Gln Leu Arg Glu Gln His<br>50                  55                  60 | 192 |
| ctc tac tac cag gac cag ctg ctg ccg gtc agc agg atc atc gtg cac<br>Leu Tyr Tyr Gln Asp Gln Leu Leu Pro Val Ser Arg Ile Ile Val His<br>65                  70                  75                  80 | 240 |
| cca cag ttc tac acc gcc cag atc gga gcg gac atc gcc ctg ctg gag<br>Pro Gln Phe Tyr Thr Ala Gln Ile Gly Ala Asp Ile Ala Leu Leu Glu<br>                85                  90                  95 | 288 |
| ctg gag gag ccg gtg aac gtc tcc agc cac gtc cac acg gtc acc ctg<br>Leu Glu Glu Pro Val Asn Val Ser Ser His Val His Thr Val Thr Leu<br>            100                 105                 110 | 336 |
| ccc cct gcc tca gag acc ttc ccc ccg ggg atg ccg tgc tgg gtc act<br>Pro Pro Ala Ser Glu Thr Phe Pro Pro Gly Met Pro Cys Trp Val Thr<br>        115                 120                 125 | 384 |
| ggc tgg ggc gat gtg gac aat gat gag cgc ctc cca ccg cca ttt cct<br>Gly Trp Gly Asp Val Asp Asn Asp Glu Arg Leu Pro Pro Pro Phe Pro<br>130                 135                 140 | 432 |
| ctg aag cag gtg aag gtc ccc ata atg gaa aac cac att tgt gac gca<br>Leu Lys Gln Val Lys Val Pro Ile Met Glu Asn His Ile Cys Asp Ala<br>145                 150                 155                 160 | 480 |
| aaa tac cac ctt ggc gcc tac acg gga gac gac gtc cgc atc gtc cgt<br>Lys Tyr His Leu Gly Ala Tyr Thr Gly Asp Asp Val Arg Ile Val Arg<br>                165                 170                 175 | 528 |
| gac gac atg ctg tgt gcc ggg aac acc cgg agg gac tca tgt caa ggc<br>Asp Asp Met Leu Cys Ala Gly Asn Thr Arg Arg Asp Ser Cys Gln Gly<br>            180                 185                 190 | 576 |
| gac gcc ggc gga cct ctg gtg tgc aag gtg aat ggc acc tgg ctg cag<br>Asp Ala Gly Gly Pro Leu Val Cys Lys Val Asn Gly Thr Trp Leu Gln<br>        195                 200                 205 | 624 |
| gcg ggc gtg gtc agc tgg ggc gag ggc tgt gcc cag ccc aac cgg cct<br>Ala Gly Val Val Ser Trp Gly Glu Gly Cys Ala Gln Pro Asn Arg Pro<br>210                 215                 220 | 672 |
| ggc atc tac acc cgt gtc acc tac tac ttg gac tgg atc cac cac tat<br>Gly Ile Tyr Thr Arg Val Thr Tyr Tyr Leu Asp Trp Ile His His Tyr<br>225                 230                 235                 240 | 720 |
| gtc ccc aaa aag ccg<br>Val Pro Lys Lys Pro<br>                245 | 735 |

<210> SEQ ID NO 49
<211> LENGTH: 245
<212> TYPE: PRT
<213> ORGANISM: Homo sapiens

<400> SEQUENCE: 49

Ile Val Gly Gly Gln Glu Ala Pro Arg Ser Lys Trp Pro Trp Gln Val
1               5                   10                  15

Ser Leu Arg Val His Gly Pro Tyr Trp Met His Phe Cys Gly Gly Ser
                20                  25                  30

Leu Ile His Pro Gln Trp Val Leu Thr Ala Ala His Cys Val Gly Pro
            35                  40                  45

Asp Val Lys Asp Leu Ala Ala Leu Arg Val Gln Leu Arg Glu Gln His
        50                  55                  60

-continued

```
Leu Tyr Tyr Gln Asp Gln Leu Leu Pro Val Ser Arg Ile Ile Val His
 65                  70                  75                  80

Pro Gln Phe Tyr Thr Ala Gln Ile Gly Ala Asp Ile Ala Leu Leu Glu
                 85                  90                  95

Leu Glu Glu Pro Val Asn Val Ser Ser His Val His Thr Val Thr Leu
            100                 105                 110

Pro Pro Ala Ser Glu Thr Phe Pro Pro Gly Met Pro Cys Trp Val Thr
        115                 120                 125

Gly Trp Gly Asp Val Asp Asn Asp Glu Arg Leu Pro Pro Pro Phe Pro
130                 135                 140

Leu Lys Gln Val Lys Val Pro Ile Met Glu Asn His Ile Cys Asp Ala
145                 150                 155                 160

Lys Tyr His Leu Gly Ala Tyr Thr Gly Asp Asp Val Arg Ile Val Arg
                165                 170                 175

Asp Asp Met Leu Cys Ala Gly Asn Thr Arg Arg Asp Ser Cys Gln Gly
            180                 185                 190

Asp Ala Gly Gly Pro Leu Val Cys Lys Val Asn Gly Thr Trp Leu Gln
        195                 200                 205

Ala Gly Val Val Ser Trp Gly Glu Gly Cys Ala Gln Pro Asn Arg Pro
210                 215                 220

Gly Ile Tyr Thr Arg Val Thr Tyr Tyr Leu Asp Trp Ile His His Tyr
225                 230                 235                 240

Val Pro Lys Lys Pro
                245
```

<210> SEQ ID NO 50
<211> LENGTH: 735
<212> TYPE: DNA
<213> ORGANISM: Homo sapiens
<220> FEATURE:
<221> NAME/KEY: CDS
<222> LOCATION: (1)..(735)

<400> SEQUENCE: 50

```
atc gtc ggg ggt cag gag gcc ccc agg agc aag tgg ccc tgg cag gtg      48
Ile Val Gly Gly Gln Glu Ala Pro Arg Ser Lys Trp Pro Trp Gln Val
 1               5                  10                  15 agc ctg aga gtc cac ggc cca tac tgg atg cac ttc tgc ggg ggc tcc      96
Ser Leu Arg Val His Gly Pro Tyr Trp Met His Phe Cys Gly Gly Ser
                 20                  25                  30 ctc atc cac ccc cag tgg gtg ctg acc gca gcg cac tgc gtg gga ccg     144
Leu Ile His Pro Gln Trp Val Leu Thr Ala Ala His Cys Val Gly Pro
             35                  40                  45 gac gtc aag gat ctg gcc gcc ctc agg gtg caa ctg cgg gag cag cac     192
Asp Val Lys Asp Leu Ala Ala Leu Arg Val Gln Leu Arg Glu Gln His
 50                  55                  60 ctc tac tac cag gac cag ctg ctg ccg gtc agc agg atc atc gtg cac     240
Leu Tyr Tyr Gln Asp Gln Leu Leu Pro Val Ser Arg Ile Ile Val His
 65                  70                  75                  80 cca cag ttc tac acc gcc cag atc gga gcg gac atc gcc ctg ctg gag     288
Pro Gln Phe Tyr Thr Ala Gln Ile Gly Ala Asp Ile Ala Leu Leu Glu
                 85                  90                  95 ctg gag gag ccg gtg aac gtc tcc agc cac gtc cac acg gtc acc ctg     336
Leu Glu Glu Pro Val Asn Val Ser Ser His Val His Thr Val Thr Leu
            100                 105                 110 ccc cct gcc tca gag acc ttc ccc ccg ggg atg ccg tgc tgg gtc act     384
Pro Pro Ala Ser Glu Thr Phe Pro Pro Gly Met Pro Cys Trp Val Thr
        115                 120                 125
```

```
ggc tgg ggc gat gtg gac aat gat gag cgc ctc cca ccg cca ttt cct    432
Gly Trp Gly Asp Val Asp Asn Asp Glu Arg Leu Pro Pro Pro Phe Pro
    130                 135                 140 ctg aag cag gtg aag gtc ccc ata atg gaa aac cac att tgt gac gca    480
Leu Lys Gln Val Lys Val Pro Ile Met Glu Asn His Ile Cys Asp Ala
145                 150                 155                 160 aaa tac cac ctt ggc gcc tac acg gga gac gac gtc cgc atc gtc cgt    528
Lys Tyr His Leu Gly Ala Tyr Thr Gly Asp Asp Val Arg Ile Val Arg
                165                 170                 175 gac gac atg ctg tgt gcc ggg aac acc cgg agg gac tca tgc caa gga    576
Asp Asp Met Leu Cys Ala Gly Asn Thr Arg Arg Asp Ser Cys Gln Gly
            180                 185                 190 gac gcc ggc gga cca ctg gtg tgc aag gtg aat ggc acc tgg ctg cag    624
Asp Ala Gly Gly Pro Leu Val Cys Lys Val Asn Gly Thr Trp Leu Gln
        195                 200                 205 gcg ggc gtg gtc agc tgg ggc gag ggc tgt gcc cag ccc aac cgg cct    672
Ala Gly Val Val Ser Trp Gly Glu Gly Cys Ala Gln Pro Asn Arg Pro
    210                 215                 220 ggc atc tac acc cgt gtc acc tac tac ttg gac tgg atc cac cac tat    720
Gly Ile Tyr Thr Arg Val Thr Tyr Tyr Leu Asp Trp Ile His His Tyr
225                 230                 235                 240 gtc ccc aaa aag ccg                                                735
Val Pro Lys Lys Pro
                245

<210> SEQ ID NO 51
<211> LENGTH: 245
<212> TYPE: PRT
<213> ORGANISM: Homo sapiens

<400> SEQUENCE: 51

Ile Val Gly Gly Gln Glu Ala Pro Arg Ser Lys Trp Pro Trp Gln Val
1               5                   10                  15

Ser Leu Arg Val His Gly Pro Tyr Trp Met His Phe Cys Gly Gly Ser
            20                  25                  30

Leu Ile His Pro Gln Trp Val Leu Thr Ala Ala His Cys Val Gly Pro
        35                  40                  45

Asp Val Lys Asp Leu Ala Ala Leu Arg Val Gln Leu Arg Glu Gln His
    50                  55                  60

Leu Tyr Tyr Gln Asp Gln Leu Leu Pro Val Ser Arg Ile Ile Val His
65                  70                  75                  80

Pro Gln Phe Tyr Thr Ala Gln Ile Gly Ala Asp Ile Ala Leu Leu Glu
                85                  90                  95

Leu Glu Glu Pro Val Asn Val Ser Ser His Val His Thr Val Thr Leu
            100                 105                 110

Pro Pro Ala Ser Glu Thr Phe Pro Pro Gly Met Pro Cys Trp Val Thr
        115                 120                 125

Gly Trp Gly Asp Val Asp Asn Asp Glu Arg Leu Pro Pro Phe Pro
    130                 135                 140

Leu Lys Gln Val Lys Val Pro Ile Met Glu Asn His Ile Cys Asp Ala
145                 150                 155                 160

Lys Tyr His Leu Gly Ala Tyr Thr Gly Asp Asp Val Arg Ile Val Arg
                165                 170                 175

Asp Asp Met Leu Cys Ala Gly Asn Thr Arg Arg Asp Ser Cys Gln Gly
            180                 185                 190

Asp Ala Gly Gly Pro Leu Val Cys Lys Val Asn Gly Thr Trp Leu Gln
        195                 200                 205
```

```
Ala Gly Val Val Ser Trp Gly Glu Gly Cys Ala Gln Pro Asn Arg Pro
    210                 215                 220

Gly Ile Tyr Thr Arg Val Thr Tyr Tyr Leu Asp Trp Ile His His Tyr
225                 230                 235                 240

Val Pro Lys Lys Pro
            245

<210> SEQ ID NO 52
<211> LENGTH: 275
<212> TYPE: PRT
<213> ORGANISM: Homo sapiens
<220> FEATURE:
<221> NAME/KEY: VARIANT
<222> LOCATION: (3)..(3)
<223> OTHER INFORMATION: Beta I and Beta II are N at this residue
<220> FEATURE:
<221> NAME/KEY: VARIANT
<222> LOCATION: (23)..(23)
<223> OTHER INFORMATION: Beta I and Beta II are G at this residue
<220> FEATURE:
<221> NAME/KEY: VARIANT
<222> LOCATION: (28)..(28)
<223> OTHER INFORMATION: Beta I and Beta II are R at this residue
<220> FEATURE:
<221> NAME/KEY: VARIANT
<222> LOCATION: (29)..(29)
<223> OTHER INFORMATION: Beta I and Beta II are V at this residue
<220> FEATURE:
<221> NAME/KEY: VARIANT
<222> LOCATION: (51)..(53)
<223> OTHER INFORMATION: Beta I and Beta II are HGP at these residues
<220> FEATURE:
<221> NAME/KEY: VARIANT
<222> LOCATION: (76)..(76)
<223> OTHER INFORMATION: Beta I and Beta II are V at this residue
<220> FEATURE:
<221> NAME/KEY: VARIANT
<222> LOCATION: (85)..(85)
<223> OTHER INFORMATION: Beta I and Beta II are A at this residue
<220> FEATURE:
<221> NAME/KEY: VARIANT
<222> LOCATION: (115)..(116)
<223> OTHER INFORMATION: Beta I and Beta II are TA at these residues
<220> FEATURE:
<221> NAME/KEY: VARIANT
<222> LOCATION: (118)..(118)
<223> OTHER INFORMATION: Beta I and Beta II are I at this residue
<220> FEATURE:
<221> NAME/KEY: VARIANT
<222> LOCATION: (132)..(132)
<223> OTHER INFORMATION: Beta II is K at this residue
<220> FEATURE:
<221> NAME/KEY: VARIANT
<222> LOCATION: (133)..(133)
<223> OTHER INFORMATION: Beta I and Beta II are V at this residue
<220> FEATURE:
<221> NAME/KEY: VARIANT
<222> LOCATION: (136)..(136)
<223> OTHER INFORMATION: Beta I and Beta II are H at this residue
<220> FEATURE:
<221> NAME/KEY: VARIANT
<222> LOCATION: (141)..(141)
<223> OTHER INFORMATION: Beta I and Beta II are T at this residue
<220> FEATURE:
<221> NAME/KEY: VARIANT
<222> LOCATION: (168)..(168)
<223> OTHER INFORMATION: Beta I and Beta II are R at this residue
<220> FEATURE:
<221> NAME/KEY: VARIANT
<222> LOCATION: (204)..(204)
<223> OTHER INFORMATION: Beta I and Beta II are V at this residue
<220> FEATURE:
<221> NAME/KEY: VARIANT
<222> LOCATION: (215)..(216)
<223> OTHER INFORMATION: Beta I and Beta II are TR at these residues
```

-continued

```
<220> FEATURE:
<221> NAME/KEY: VARIANT
<222> LOCATION: (221)..(221)
<223> OTHER INFORMATION: Beta I and Beta II are Q at this residue
<220> FEATURE:
<221> NAME/KEY: VARIANT
<222> LOCATION: (245)..(245)
<223> OTHER INFORMATION: Beta I and Beta II are G at this residue

<400> SEQUENCE: 52

Met Leu Ser Leu Leu Leu Ala Leu Pro Val Leu Ala Ser Arg Ala
1               5                   10                  15

Tyr Ala Ala Pro Ala Pro Val Gln Ala Leu Gln Gln Ala Gly Ile Val
            20                  25                  30

Gly Gly Gln Glu Ala Pro Arg Ser Lys Trp Pro Trp Gln Val Ser Leu
        35                  40                  45

Arg Val Arg Asp Arg Tyr Trp Met His Phe Cys Gly Gly Ser Leu Ile
    50                  55                  60

His Pro Gln Trp Val Leu Thr Ala Ala His Cys Leu Gly Pro Asp Val
65                  70                  75                  80

Lys Asp Leu Ala Thr Leu Arg Val Gln Leu Arg Glu Gln His Leu Tyr
                85                  90                  95

Tyr Gln Asp Gln Leu Leu Pro Val Ser Arg Ile Ile Val His Pro Gln
            100                 105                 110

Phe Tyr Ile Ile Gln Thr Gly Ala Asp Ile Ala Leu Leu Glu Leu Glu
        115                 120                 125

Glu Pro Val Asn Ile Ser Ser Arg Val His Thr Val Met Leu Pro Pro
    130                 135                 140

Ala Ser Glu Thr Phe Pro Pro Gly Met Pro Cys Trp Val Thr Gly Trp
145                 150                 155                 160

Gly Asp Val Asp Asn Asp Glu Pro Leu Pro Pro Pro Phe Pro Leu Lys
                165                 170                 175

Gln Val Lys Val Pro Ile Met Glu Asn His Ile Cys Asp Ala Lys Tyr
            180                 185                 190

His Leu Gly Ala Tyr Thr Gly Asp Asp Val Arg Ile Ile Arg Asp Asp
        195                 200                 205

Met Leu Cys Ala Gly Asn Ser Gln Arg Asp Ser Cys Lys Gly Asp Ser
    210                 215                 220

Gly Gly Pro Leu Val Cys Lys Val Asn Gly Thr Trp Leu Gln Ala Gly
225                 230                 235                 240

Val Val Ser Trp Asp Glu Gly Cys Ala Gln Pro Asn Arg Pro Gly Ile
                245                 250                 255

Tyr Thr Arg Val Thr Tyr Tyr Leu Asp Trp Ile His His Tyr Val Pro
            260                 265                 270

Lys Lys Pro
        275
```

RECOMBINANT PROTEOLYTIC TRYPTASES, ACTIVE SITE MUTANTS THEREOF, AND METHODS OF MAKING SAME

This is a Continuation-in-part of application Ser. No. 09/079,970, filed Apr. 15, 1998, now U.S. Pat. No. 6,274,366.

FIELD OF THE INVENTION

The invention is directed to a method of making an enzymatically-active recombinant proteolytic tryptase in a genetically-engineered microbial host, expression constructs encoding the enzymatically-active proteolytic tryptase, and genetically-engineered eukaryotes which express the enzymatically-active recombinant proteolytic tryptase. The invention is also directed to a method of making an active site mutant of a recombinant proteolytic tryptase in a genetically-engineered microbial host, expression constructs encoding the mutated proteolytic tryptase lacking enzymatic activity due to the active site mutation, and genetically-engineered eukaryotes which express the mutated recombinant proteolytic tryptase having the active site mutation.

BIBLIOGRAPHY

Complete bibliographic citations to the references noted herein are included in the Bibliography section, immediately preceding the Sequence Listing.

DESCRIPTION OF THE RELATED ART

Mast cell β-tryptase is a neutral serine protease of presently unknown biological function in vivo. However, it has been implicated in asthma, angiogenesis, and tissue remodeling. It constitutes up to 20% w/v of the total granule protein of mast cells. β-tryptase is selectively stored in mast cell granules and is released upon mast cell degranulation. Because β-tryptase is unique to mast cells, it has gained favor as a specific marker of mast cell-mediated pathology. For a complete discussion regarding mast cell heterogeneity, structure, and mediators, see Nilsson and Schwartz (1994).

In asthma, mast cells have long been implicated in the acute immunological reactions that occur immediately following allergen challenge, see, for example, Holgate and Church (1992). In an allergic sheep model, J. M. Clark et al. (1995) have shown that tryptase has a role as an important mediator in antigen-induced airway responses.

A number of proteins have been reported to be substrates for tryptase cleavage in vitro, including the α- and β-chains of fibrinogen, see Schwartz et al.(1985). Tryptase cleaves fibrinogen into fragments that lack clotting activity, potentially acting as an anticoagulant at sites of mast cell degranulation.

Purified native human β-tryptase is a tetrameric endoprotease of approximately 134 kDa. Each of the four subunits is approximately 31 to 34 kDa in size. As noted in Schwartz (1995), human tryptase was first purified to apparent homogeneity from dispersed and enriched lung mast cells in 1981. However, further research has shown that there are at least two different types, or groups, of mammalian tryptase: a proteolytic tryptase and a non-proteolytic tryptase. The proteolytic tryptases, in their protryptase form, are able to be cleaved to yield active tryptases. Cleavable proteolytic tryptase includes β-tryptases, β-like tryptases, and transmembrane tryptases. β-tryptases can be further divided into two predominant β isoforms: β-I and β-II. The β-I isoform has previously been referred to as skin tryptase, and the β-II isoform has previously been referred to as lung tryptase. This new nomenclature is used herein.

In contrast to the cleavable proteolytic tryptase, a second type of tryptase, non-proteolytic tryptase, is not able to be cleaved. Thus, the non-proteolytic tryptase is not enzymatically active. The non-proteolytic tryptase includes α-tryptase. Huang et al. (1999) attribute the cleavability in proteolytic tryptase to amino acids R-V at amino acids −3 and −2 from amino acid 1 (the first amino acid of the cleaved proteolytic tryptase). R-V is present in β-tryptase, whereas it is absent in α-tryptase. Moreover, the proteolytic and non-proteolytic tryptase are from distinct genes.

Human tryptase is conventionally isolated from cadaveric lung tissue, as described by Smith et al. (1984).

A number of researchers have reported cloning cDNAs which encode human tryptase, see Miller et al. (1990), Vanderslice et al. (1990), and Blom and Hellman (1993), as well as rat mast cell tryptase, see Ide et al. (1995).

However, previous attempts at expressing human tryptase, particularly expressing active tryptase, using either bacterial or baculovirus expression systems are plagued with a myriad of problems, including protein folding problems that result in a lack of enzymatic activity. These failures are due, at least in part, to the fact that the tryptase enzyme is extensively modified post-translationally to yield the active form of the enzyme. Consequently, the specific activity of a recombinant tryptase produced in a prokaryote would be expected to be low due to the lack of post-translational glycosylation. As a further consequence, previous attempts to produce enzymatically-active recombinant human tryptase have proven to be far less than ideal because the methods require post-expression chemical modifications and subsequent purification to activate the enzyme precursor.

For instance, Sakai et al. (1996) report the expression and purification of recombinant human α-tryptase and β-tryptase precursors in a baculovirus system. However, the tryptase precursors formed are inactive.

Regarding the use of methylotrophic yeasts (e.g., *Hansenula polymorpha, Kluyveromyces lactis, Pichia pastoris, Schizosaccharomyces pombe, Schwanniomyces occidentalis* and *Yarrowia lipolytica*) as hosts for the production of heterologous proteins, the characteristics of these organisms and their suitability for such use has been extensively reviewed in the relevant literature. See, for example, Faber et al. (1995) and Buckholz and Gleeson (1991).

Chan et al. (1999) have cloned protryptase in a methylotrophic yeast. The expressed product of Chan et al. is a protryptase monomer that must be exogenously processed to form an active tetrameric tryptase. This conversion requires an additional two column purification method, including a heparin- and dipeptidyl peptidase I-dependent activation step. These exogenous processing steps result in very low expression levels, large losses in the amount of enzyme at each step, and a very low final yield of purified enzyme.

Previous cloned tryptases do not include the cleavage site. Thus, the cloned tryptase lacked the RV at amino acids −3 and −2. Therefore, these cloned tryptases do not cleave. Because these previous tryptase systems do not cleave, the previous tryptases do not spontaneously form enzymatically-active tetramers.

The active sites of proteolytic tryptases have not been previously determined. While amino acids 44, 91, and 194 are conserved in proteolytic tryptases, and implicated to exist in the enzymatic active site, there has been no previous demonstration that these three amino acids are required for activity.

Huang et al. (1999) have mutated α-tryptase and expressed it in insect cells to determine the importance of residue 215, which is in one of the surface loops that forms the substrate-binding cleft of α-tryptase. Expression of heterologous α-tryptase in insect cells by Huang et al. requires several ex vivo post-translational steps to activate the protein.

SUMMARY OF THE INVENTION

Expression of tryptase in yeast provides the only expression system in which an enzymatically-active proteolytic tryptase, (e.g., β-I, β-II, β-like), and active site mutants of proteolytic tryptase, are produced. To produce the various active proteolytic tryptases, a DNA expression construction is used to shuttle DNA between bacteria and yeast. For example, site-directed mutagenesis of tryptase-encoding DNA can be done in conventional E. coli hosts, and the mutated DNA then transferred to a suitable eukaryotic host for expression of the novel tryptase.

A preferred embodiment of the invention is directed to a DNA expression construct comprising, in 5' to 3' order: a promoter, the promoter operationally linked to a secretion signal sequence, the secretion signal sequence operationally-linked to a DNA sequence encoding a proteolytic tryptase having an active site mutation, and wherein the expression construct drives expression of a mature proteolytic tryptase that lacks enzymatic activity in hosts transformed to contain the expression construct, the lack of enzymatic activity being due to the active site mutation.

Another preferred embodiment of the invention is directed to a DNA expression construct comprising, in 5' to 3' order: a promoter selected from the group consisting of AOX1, GAP, MOX, FMD, ADH, LAC4, XPR2, LEU2, GAM1, PGK1, GAL7, GADPH, CYC1, and CUP1, the promoter operationally linked to a secretion signal sequence, the secretion signal sequence operationally-linked to a DNA sequence encoding proteolytic tryptase having an active site mutation, the DNA sequence operationally linked to a terminator sequence.

According to the present invention, DNA encoding proteolytic tryptase is mutated in one of three active site amino acids (amino acids 44, 91, and 194) of proteolytic tryptase. The mutated DNA is cloned into a eukaryotic expression construct, and transformed into a suitable eukaryotic host cell, preferably a yeast host cell. Successfully transformed host cells express, post-translationally process, and secrete the active site-mutated form of mature tryptase, preferably upon induction of expression.

Another embodiment of the invention is directed to a recombinant protein lacking tryptase enzymatic activity which is produced by organisms transformed to contain and express the expression construct. Preferably, the DNA expression construct has a mutation at one of three putative active sites within the proteolytic tryptase gene: histidine at amino acid 44, aspartic acid at amino acid 91, and serine at amino acid 194. The mutation preferably changes the amino acid at these positions to alanine.

The invention is further drawn to a method of generating polyclonal or monoclonal anti-human proteolytic tryptase antibodies. A preferred embodiment comprises inoculating an animal with the active site mutants of the proteolytic tryptase produced by organisms transformed to contain and express the expression construct. Other recombinant methods of producing antibodies can also be used including, but not limited to, phage display technology, library screening, and a combination of these two methods. The invention is also drawn to polyclonal, monoclonal, or chimeric anti-human proteolytic tryptase antibodies produced thereby.

Another embodiment of the invention is directed to a DNA expression construct comprising, in 5' to 3' order: a promoter, the promoter operationally linked to a secretion signal sequence, the secretion signal sequence operationally-linked to a DNA sequence encoding proteolytic tryptase, wherein the expression construct drives the expression of mature proteolytic tryptase that has enzymatic activity in hosts transformed to contain the expression construct.

Yet another embodiment of the invention is drawn to a DNA expression construct comprising, in 5' to 3' order: a promoter, the promoter operationally linked to a secretion signal sequence, the secretion signal sequence operationally-linked to a DNA sequence encoding human tryptase β-II having a nucleotide sequence encoding the polypeptide of SEQ ID NO. 6, and wherein the expression construct drives the expression of mature β-II tryptase that has enzymatic activity in hosts transformed to contain the expression construct. The mutation of β-I tryptase at amino acid 102 generates the β-II tryptase sequence identically. There are no other changes throughout the rest of the coding region of β-II tryptase. Although the mutation is generated as a mutation of β-I tryptase, it is referred to hereinafter as β-II tryptase and is identical to the coding region of β-II tryptase. The recombinant β-II tryptase is expressed off the DNA construct which is integrated into the yeast genome. In a preferred embodiment, the genetically engineered yeast cell comprises a Pichia pastoris host cell transformed to contain and express the β-II tryptase expression construct as described herein.

The invention entails operationally linking DNA sequences that encode the mature form of proteolytic tryptase immediately downstream (i.e., in the 3' direction) and in-frame to a secretion signal sequence to yield an expression construct. The expression construct, a preferred embodiment of which is a plasmid designated pPIC9-HumTryN102K, then is transformed into a suitable host, preferably a strain of yeast and most preferably a strain of the genus Pichia. Hosts so transformed express and secrete the β-II tryptase encoded by the expression construct. The β-II tryptase expressed is correctly processed by the host cell and secreted into the cell medium as an alternate isoform of tryptase.

The invention takes advantage of the fact that native tryptase is synthesized as a proprotein. The modified tryptase amplicon described herein lacks the sequences that encode the N-terminal amino acid prosequence. By cloning this sequence as an in-frame fusion to an N-terminal yeast secretion signal sequence, there is no need to subject the secreted tryptase protein to an activation process. It is secreted as a mature monomer that is cleaved and self-assembling and that spontaneously forms an active tetrameric enzyme without any further exogenous manipulation required.

To accomplish this result, the signal peptide cleavage site is positioned immediately adjacent to the N-terminus of mature tryptase protein. Cleavage of the signal peptide by action of a eukaryotic host cell protease then removes the signal peptide from the tryptase as it is secreted. The result is secretion of an enzymatically-active, mature form of tryptase containing the same amino terminal residues found in mature native tryptase molecules isolated from human tissues.

A distinct advantage of the method of producing proteolytic tryptase described herein is that the tryptase so produced, unlike previous methods, does not require any exogenous or human-aided post-expression or post-purification modifications or manipulations to initiate tryptase activity. In the invention, the monomer is cleaved as it is secreted. The self-assembly of the monomers into the active tetramer occurs after secretion from the cell. This occurs automatically after secretion. The proteolytic tryptase produced according to the invention has enzymatic activity which compares favorably with cadaveric tryptase.

Other distinct advantages of the method of producing proteolytic tryptase described herein is that the tryptase so produced has high levels of expression. Unlike conventional purification processes in which the enzyme is purified from cadavers, the method described herein and the resultant tryptase lacks the impurities that are commonly found in cadaveric tryptase. There is also a lack of the biohazards associated with using materials of cadaveric sources. The method described herein and resultant tryptase also has a higher uniformity of the purified tryptase and lower batch-to-batch variation. The resultant tryptase also has greater specific activity.

The ready availability of enzymatically-active proteolytic tryptase afforded by the invention immediately provides previously unattained advantages on several fronts. These include facilitating the large scale screening of combinatorial libraries for specific tryptase inhibitors as potential therapeutics, as well as advancing the understanding of the biological significance of tryptase in mast cell-mediated diseases.

The active site mutations of proteolytic tryptase provided by the invention furnish a tool with which to further understanding of the structural and functional properties of this unique protease. Active site refers to a site that is required for enzymatic activity. It is not limited to the surface loop of the active site. The active site mutants described herein are able to form tetramers.

The method according to the invention can be used to produce large standardized lots (>100 mg or >5 liters of yeast culture) of tryptase having defined specifications. The method can also easily be scaled to produce tryptase from microgram to gram or kilogram quantities. Using conventional methods to purify tryptase from cadavers, one human lung would result in only about 10 milligrams tryptase.

The quantity of tryptase produced in the preferred *Pichia* transformant is sufficiently large to enable larger-scale tryptase studies than were possible in the past, such as pharmacological studies, combinatorial library screens, and X-ray crystallographic studies. The large quantity of tryptase produced also allows for the development of tryptase agonists and/or antagonists.

These and other aims, objects, and advantages of the invention will become apparent upon a complete reading of the following Detailed Description of the Invention and attached claims.

BRIEF DESCRIPTION OF THE DRAWINGS

FIG. 1 is an amino acid alignment of proteolytic and non-proteolytic tryptases. The—▼—designates the first amino acid in each mature tryptase. The notations A, B, C, D, 3, 1, and 2 denote the seven loops predicted to form the substrate-binding cleft of each tryptase based on the structure of bovine pancreatic trypsin and human β-II tryptase.

DETAILED DESCRIPTION OF THE INVENTION

Figure 2:
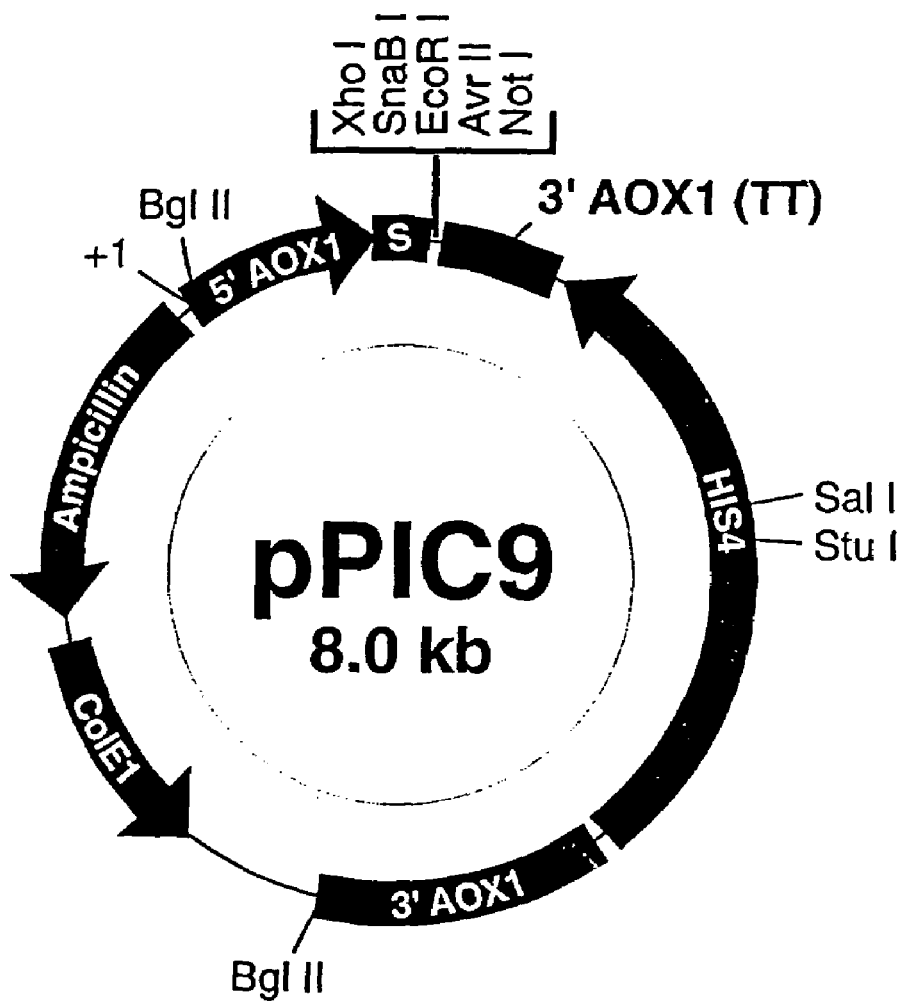
FIG. 2 is a schematic diagram of pPIC9.

Definitions:

To provide a clear and consistent understanding of the specification and claims, the following definitions are used herein. Terms not expressly described have their standard meaning as understood by those skilled in the art.

Active site mutant—Active site refers to a site that is required for enzymatic activity. It is not limited to the surface loop of the active site. As used herein, the active sites of proteolytic tryptase are amino acids 44, 91, and 194 or their comparable amino acids in the proteolytic tryptases. The active site mutants of proteolytic tryptase described herein are able to be cleaved and to form tetramers. The active site mutants lack enzymatic activity. This lack of activity is not due to the inability to form a mature tetramer, but instead is due to the mutation in the active site.

Enzymatically-active proteolytic tryptase—As applied to the expression of heterologous proteins from a genetically-engineered host cell, a protein is enzymatically active when it does not require post-expression or post-isolation chemical processing such as artificial cleavage of a secretion signal peptide or artificial glycosylation in order for the expressed/isolated protein to have the desired activity. Proteolytic tryptase must be correctly formed into the tetrameric form to be enzymatically active. Used synonymously with "mature proteolytic tryptase."

Expression construct—A DNA construct containing at least one sub-sequence encoding a protein or peptide of interest which is operationally linked to one or more regulatory sub-sequences which drive expression of the encoded protein or peptide when the construct is transformed into a suitable host cell. Such constructs also may contain sub-sequences encoding means for selecting host cells transformed to contain the construct, such as sub-sequences which confer antibiotic resistance or dietary limitations to transformed cells.

Host cells—In general, any eukaryotic cell amenable to transformation, including, but not limited to, organisms of the genera *Hansenula, Kluyveromyces, Pichia, Saccharomyces, Schizosaccharomyces, Schwanniomyces, Yarrowia*, and the like, including *Hansenula polymorpha, Kluyveromyces lactis, Pichia pastoris, Saccharomyces cerevisiae, Schizosaccharomyces pombe, Schwanniomyces occidentalis* and *Yarrowia lipolytica*. It is preferred that the host be of the genus *Pichia* and most preferred that the host cell be a *Pichia pastoris* having the characteristics of ATCC 20864.

Mature, Proteolytic Tryptase—As applied to the expression of heterologous proteins from a genetically-engineered host cell, a protein is enzymatically active when it does not require post-expression or post-isolation chemical processing such as artificial cleavage of a secretion signal peptide or artificial glycosylation in order for the expressed/isolated protein to have the desired activity. Proteolytic tryptase must be correctly formed into the tetrameric form to be enzymatically active. Used synonymously with "enzymatically-active proteolytic tryptase."

Non-proteolytic tryptase—A form of tryptase that is not cleavable and does not self-assemble. Examples of non-proteolytic tryptase include, but are not limited to, α-tryptase. It should be noted that tryptase nomenclature in the prior art has not been consistent.

Operationally linked—When referring to joined DNA sequences, denotes that the sequences are in the same reading frame and that upstream regulatory sequences will perform as such in relation to downstream structural sequences. DNA sequences which are operationally linked are not necessarily physically linked directly to one another but may be separated by intervening nucleotides which do not interfere with the operational relationship of the linked sequences.

*Pichia pastoris*—Any strain of the species *Pichia pastoris*, including, but not limited to, those strains having the characteristics of the deposited strains bearing American Type Culture Collection (ATCC, 10801 University Blvd., Manassas, Va., 20110-2209, U.S.A.) Accession Numbers 2604, 20864 (synonymous with strain GS115), 28485, 60372, 66390–66395, 76273, and 76274, as well as *Pichia pastoris* strain KM71, available commercially from Invitrogen Corporation (San Diego, Calif., U.S.A.). ATCC 20864 (strain GS115) and strain KM71 are the preferred host cell types.

Polymerase Chain Reaction (PCR)— A technique in which cycles of denaturation, annealing with a primer pair, and extension with DNA polymerase are used to generate a large number of copies of a desired polynucleotide sequence. See U.S. Pat. Nos. 4,683,195 and 4,683,202 for a description of the reaction.

Promoter—A DNA sequence at which RNA polymerase binds and which directs the specific transcription of downstream (i.e., 3') DNA sequences into corresponding RNA sequences. A promoter functions as the start signal for RNA synthesis. The promoter itself is not transcribed.

Proteolytic tryptase—A tryptase that is cleavable in its protryptase form and that is self-assemblying, wherein monomers are assembled into tetramers without any exogenouse or human-aided post-expression or post-purification modifications or manipulations to initiate tryptase activity. Examples of proteolytic tryptases include, but are not limited to, β—I tryptase (formerly referred to as skin tryptase) β-II tryptase (formerly referred to as lung tryptase), β-like tryptases, and transmembrane tryptase. It should be noted that tryptase nomenclature in the prior art has not been consistent.

Secretion signal peptide—An N-terminal extension of generally from 10 to 85 predominately hydrophobic amino acid residues. The secretion signal peptide is encoded by the secretion signal sequence and initiates a secretory pathway resulting in mobilization of the mature protein out of the cytoplasmic compartment. The secretion signal peptide is cleaved from the mature protein chain post-translation and forms no part of the mature protein. The expressed protein must be secreted in order to form the enzymatically-active tetrameric form of proteolytic-tryptase.

Secretion signal sequence—A DNA sequence located between the transcription start site of an operon and the first structural gene. The secretion signal encodes a short peptide called the secretion signal peptide.

Self-assembling tetrametic tryptase—A tryptase that is cleavable and that self-assembles. Included in this term are proteolytic tryptases. While the inventors do not wish to be limited to a particular mode of self-assembly, it is believed R-V at amino acids −3 and −2 from amino acid 1 (the first amino acid of the cleaved proteolytic tryptase) are essential to this activity.

Terminator—A DNA sequence situated at the 3' end of a transcribed sequence that signals the end of transcription.

Tryptase: Unless expressly identified otherwise, proteolytic tryptase.

Genetic Engineering:

Many of the steps noted below for the manipulation of DNA, including digesting with restriction endonucleases, amplifying by PCR, hybridizing, ligating, separating and isolating by gel electrophoresis, transforming cells with heterologous DNA, selecting successful transformants, and the like, are well known and widely practiced by those skilled in the art and are not extensively elaborated upon herein. Unless otherwise noted, the DNA protocols utilized herein are described in *Sambrook, Fritsch, and Maniatis* (1989).

Recombinant, Enzymatically-Active Proteolytic Tryptase

Proteolytic tryptases are cleavable and self-assembling tryptases that form into enzymatically-active tetramers. Non-proteolytic tryptases are not cleavable. Cleavage is required for spontaneous assembly. Thus, non-proteolytic tryptases do not self-assemble. As is shown in the amino acid alignment of FIG. 1 (see SEQ. ID. NO: 52), the proteolytic tryptases of humans share certain sequence similarities. In particular, the amino acids RV are found at amino acids at positions −3 and −2 from amino acid 1, which is shown as the ▼ symbol in FIG. 1. The ▼ symbol is the first amino acid of the cleaved proteolytic tryptase, and corresponds to residue 31 of SEQ. ID. NO: 52. The RV motif has been implicated in the cleavage of proteolytic tryptase. The RV motif is absent in α-tryptase (SEQ. ID. NO: 52), which is not cleavable, and thus does not self-assemble into tetramers.

Unlike previous recombinant tryptases, the proteolytic tryptases of the invention include the sequences before the cleavage site, the presence of which permit the proteolytic tryptases to be cleaved and self-assemble. Included in proteolytic tryptases are β-II and β-II tryptases, β-like tryptases, and transmembrane tryptases. Human β-I and β-II differ by one amino acid at position 102 (β-I has asparagine, whereas β-II has lysine). Furthermore, human β-I is glycosylated at two N-linked sites, whereas β-II at only one site. While this difference has been predicted by sequence analysis, the recombinant proteins provided by the invention are the first to demonstrate the N102 is actually glycosylated. Amino acid $N_{204}$, which is present in β-tryptase and α-tryptase, is thought to be glycosylated in all β-tryptases and α-tryptases.

Recombinant, Enzymatically-Active β-I Tryptase

Isolation of β-I Tryptase-Encoding DNA:

Referring to the construct of Example 1a, the DNA sequence encoding β-I tryptase was isolated by first collecting mast cell samples ($4 \times 10^6$, 1.1% of total cells) from a donor. Poly(A)+ RNA was then isolated by LiCl precipitation and oligo(dT)-cellulose chromatography. A cDNA library was constructed in a suitable phage vector (λ ZAP II vector, Stratagene, LaJolla, Calif., U.S.A.) and amplified once in E. coli XL1-Blue cells prior to screening.

The library of Example 1a was screened at 42° C. with a dog tryptase cDNA $^{32}$P-labeled to $2 \times 10^8$ cpm/μg by nick-translation, in conventional fashion except for using 30% formamide in the hybridization solution and 5×SSC. Positive recombinants were identified by autoradiography, plaque-purified, and re-probed. Phagemids containing inserts that hybridize to the cDNA probe were excised from the phage vector using R408 helper phage, transformed into E. coli XL1-Blue cells, and purified by alkaline lysis. The sequence of the cDNA inserts was determined by dideoxy chain termination modified for double-stranded DNA by using SEQUENASE-brand sequencing kit (United States Biochemical, Cleveland, Ohio, U.S.A.). The M13 forward, reverse, and KS primers (Stratagene) were used for the initial sequence reaction. Subsequent sequencing reactions used oligonucleotide primers designed from the previously determined sequence.

Positive clones were also used to screen commercial libraries, such as the human placental genomic library in EMBL-3 (Clontech, Palo Alto, Calif., U.S.A.). Here, the cDNA was labeled with biotin-7-dATP by nick-translation and hybridized at 50° C. to the immobilized phage DNA and visualized. Positive clones were plaque-purified and re-screened. Phage DNA was purified by the plate lysate method in conventional fashion and digested with Bam HI to yield genomic fragments. The genomic fragments were separated by agarose gel electrophoresis, transferred to nitrocellulose, and hybridized to tryptase cDNA. Hybridizing fragments were ligated into the Bam HI site of pBluescript KS(+) phagemid (Stratagene), and the nucleotide sequence determined as described for the cDNAs. See Vanderslice et al. (1990).

A DNA sequence of a β-I tryptase encoding fragment isolated as described above is depicted in SEQ. ID. NO. 5, which encodes the amino acid shown in SEQ. ID. NO. 6. The amino acid of SEQ. ID. NO. 6 is cleaved to form the mature proteolytic tryptase, which is described as SEQ. ID. NO. 2. The DNA sequence of the mature β-I tryptase encoding fragment is depicted as SEQ. ID. NO. 1 (the encoded protein is shown in SEQ. ID. NO. 2).

Incorporation of β-I Tryptase DNA Into Expression Construct:

Referring to Example 1a, the DNA encoding the β-I tryptase was then operationally linked with suitable regulatory sub-sequences to drive expression of the tryptase-coding sequence in a eukaryotic host, to yield an expression construct. Preferably, the construct also contains one or more sub-sequences to enable the easy identification of positive transformants. At a minimum, the expression construct should include, operationally linked in 5' to 3' order, a promoter sequence, a secretion signal sequence, the β-I tryptase coding sequence, and a terminator sequence. In this fashion, the promoter will initiate transcription of the downstream secretion signal sequence and β-I tryptase structural gene when incorporated into a suitable host.

Several plasmids containing the required regulatory sub-sequences, as well as sub-sequences encoding selectable antibiotic and/or auxotrophic markers and multiple cloning sites are available commercially. A preferred plasmid, pPIC9, is available from Invitrogen (San Diego, Calif., U.S.A.). A schematic of pPIC9 is provided in FIG. 2.

pPIC9 is a circular DNA plasmid of 8023 base pairs and contains a 5' AOX1 promoter fragment at bases 1–948, an α-Factor secretion signal (designated S in FIG. 2) at bases 949–1218, a multiple cloning site at bases 1192–1241, and a 3' AOX1 terminator fragment (designated 3' AOX1 (TT)) at bases 1253–1586. pPIC9 also contains an ampicillin resistance gene at bases 7713–6853 and a ColE1 origin at bases 6708–6034. The multiple cloning site includes recognition sites for Xho I, Sna BI, Eco RI, Avr II, and Not I. The plasmid also contains Bgl II, Sac I, Sal I, and Stu I recognition sites.

Other eukaryotic promoter and terminator sequences can be used with comparable success in the expression construct. Generally, the promoter should be homologous to the chosen host in order to ensure efficient expression of the encoded tryptase, although this is not required. The promoter may be constituitive or inducible. Suitable eukaryotic promoter and terminator sequences include (in addition to AOX1) GAP, MOX, FMD, ADH, LAC4, XPR2, LEU2, GAM1, PGK1, GAL7, GADPH, CYC1, CUP1, and the like. This list is illustrative, not exclusive.

As shown in Example 1a, the DNA sequence encoding the β-I tryptase was introduced into the multiple cloning site of pPIC9 by modifying the 5' and 3' ends of the isolated tryptase DNA sequence to yield complementary overhangs with the sticky ends afforded by the restriction sites contained in the multiple cloning site of pPIC9. The pPIC9 plasmid and the amplified β-I tryptase fragments were then digested with suitable restriction enzymes, hybridized, ligated (T4 DNA ligase), transformed (calcium chloride) into a suitable bacterial host (E. coli strain JM109, Promega Corporation, Madison, Wis., U.S.A. is preferred), and positive clones selected by ampicillin resistance, all in conventional and well-known fashion.

To modify the ends of the β-I tryptase encoding DNA fragment, the β-I tryptase DNA was amplified using partially homologous nucleotide primers which include suitable restriction nuclease recognition sites but which do not alter the amino acid sequence of the encoded protein. The resulting amplicon thus encodes the same protein, but includes the restriction sites needed to incorporate the β-I tryptase encoding fragment into an expression construct. Using knowledge of the β-I tryptase DNA sequence and the degeneracy of the DNA code, any number of suitable primers which will introduce an appropriate recognition site without altering the amino acid sequence of the encoded peptide can be constructed.

As described more fully in the Examples, amplifying the DNA sequence as shown in SEQ. ID. NO. 5 with the illustrative primers depicted in SEQ. ID. NO. 3 and SEQ. ID. NO. 4 yielded an amplified β-I tryptase encoding DNA fragment which includes an Xho I restriction site near the 5' end of the fragment and a Not I restriction site near the 3' end of the fragment. These two restriction sites are exemplary only. Virtually any restriction site can be introduced at the terminal ends of the β-I tryptase encoding DNA fragment without altering the sequence of the encoded β-I tryptase enzyme. The choice is up to the user, and depends almost entirely upon the nature, location, and number of the restriction sites available in the other sub-sequences which are to be incorporated into the ultimate expression construct.

The modified amplicon containing the terminal Xho I and Not I sites can then easily be inserted into any plasmid or construct containing an Xho I recognition site and a Not I recognition site, in conventional and well-known fashion.

Other sub-sequences may also be included in the expression construct. One particularly helpful sub-sequence is a secretion signal sequence encoding a signal peptide to direct the secretion of the expressed protein from the cell. The signal peptide forms no part of the mature protein—the signal peptide is cleaved from the protein as it passes through the cell wall, thereby yielding the mature protein. For purposes of the present invention, the preferred secretion signal sequence is one that encodes a KEX2 cleavage site in the unprocessed protein. The action of KEX2, a yeast signal peptidase, then will cleave the signal peptide from the remainder of the protein, thereby yielding the mature β-I tryptase enzyme. An α-Factor secretion signal sub-sequence is preferred for secretion of the recombinant β-I tryptase using a *Pichia* host.

As is detailed in Example 1a, after transforming the β-I tryptase encoding construct into a bacterial host for cloning, positive transformants were screened for the properly assembled expression construct by restriction analysis of plasmids isolated from ampicillin-resistant colonies. The expression constructs were then isolated in standard fashion and transformed into a suitable eukaryotic host for expression of the human β-I tryptase encoded thereon.

Transformation of Eukaryotic Host:

The expression construct encoding human β-I tryptase then was incorporated into a suitable eukaryotic host as described in Example 2a. The preferred host is a yeast cell. A eukaryotic host must be used so that the expressed β-I tryptase is properly processed by the cell after translation. Post-translational intracellular processing by the eukaryotic host is critical to impart enzymatic activity to the mature protein.

The preferred hosts include *Hansenula polymorpha, Kluyveromyces lactis, Pichia pastoris, Saccharomyces cerevisiae, Schizosaccharomyces pombe, Schwanniomyces occidentalis* and *Yarrowia lipolytica*. It is most preferred that the host be of the genus *Pichia*. From among *Pichia*, it is most preferred that the host cell be a *Pichia pastoris* cell having the characteristics of ATCC 20864 (strain GS 115) or KM71 (Invitrogen).

Transformation is preferably accomplished by electroporation in conventional fashion. The host cells were made electrocompetent by extensive washing with 1 M Sorbitol and then mixed with aliquots of the expression construct which have been pre-digested with a suitable single-cutting restriction enzyme (e.g., in pPIC9, Sal I or Sac I) and transformed. Successfully transformed auxotrophs were screened on minimal media, and then rescreened on fresh media to identify clones which produce high levels of tryptase.

If operationally linked to an inducible promoter, successfully transformed auxotrophs are screened in a medium containing the required inducer to initiate β-I tryptase production.

β-I tryptase can be assayed from the culture broth using an enzyme-linked immunosorbent assay as described in Niles and Haak-Frendscho, U.S. Pat. No. 5,594,116, issued Jan. 14, 1997 and assigned to Promega Corporation, and which is incorporated herein by reference. Briefly, suitable microtiter plates were coated with capture antibodies specific for human tryptase derived from immunized avians, preferably chickens. This was done by coating the microtiter plates with a solution of the capture antibody and incubating for 8 to 48 hours at 4° C. The coated plates were then thoroughly rinsed with a solution of TBST (tris-buffered saline with Tween 20. Non-specific residual binding to the microtiter plate itself was then blocked by coating the plate with a blocking buffer. A commonly used blocking buffer is a solution of 0.05% Tween 20 containing bovine serum albumin (BSA). The plates were again rinsed with TBST.

The solutions to be tested were then diluted in the blocking buffer. Preparing a number of serial dilutions is recommended. The plates were then coated with the test solutions and incubated for at least two hours at room temperature.

After incubation the plates were again rinsed with TBST. Other buffered solutions, such as phosphate-buffered saline or phosphate-buffered saline with Tween, also may be used.

The next step is to introduce a tryptase detect antibody solution which binds to the captured tryptase. The preferred detect antibody is a murine-derived monoclonal antibody specific to tryptase. A solution of the monoclonal antibody was prepared and the wells are coated and incubated for at least two hours at room temperature. After incubation, the plates were again washed with TBST.

The plates were rinsed with TBST, and were then coated with a specific antibody/horseradish peroxidase conjugate. Such antibody/horseradish peroxidase conjugates are well known in the art. A conventional method to prepare such conjugates includes using sodium periodate to oxidize the carbohydrate side chains of horseradish peroxidase, followed by the formation of a Schiff base between the activated peroxidase and amino groups of the antibody. The preferred antibody for the conjugate is goat anti-mouse IgG antibodies. The Schiff base then was reduced (sodium borohydride) to yield a stable antibody/enzyme conjugate. The wells of the microtiter plates then were incubated for at least two hours at room temperature. It is important here that the conjugate antibodies must not react with the capture antibody or the tryptase itself. It is preferred that the plates be rinsed with TBS three times prior to addition of the substrate.

A horseradish peroxidase substrate solution was then added to each well and the wells incubated for 15 min at room temperature. Acid was added to stop the color reaction. The wells then were examined spectrophotometrically at 450 nm. For colorimetric detection, horseradish peroxidase-conjugated anti-mouse antibody used in conjunction with the substrate 3,3',5,5'-tetramethylbenzidine (TMB) is preferred. Other peroxidase substrates, such as o-phenylenediamine dihydrochloride (OPD) and anti-mouse alkaline phosphatase conjugates function with equal success. This colorimetric double antibody-sandwich ELISA has a sensitivity of about 20 pg/ml, a linear response range from 15 to 2000 pg/ml, and an r≦0.99.

The CBZ Lys-Thiobenyl Ester/DNTB Coupled Cleavage Assay or other enzyme cleavage assays can also be used to assay for enzymatic activity of β-1 tryptase.

Recombinant, Enzymatically-Active β-II Tryptase

Convert Human β-I Tryptase into Recombinant Human β-II Tryptase:

Human β-I and β-II tryptase have identical amino acid sequences except for amino acid 102: β-I tryptase has an asparagine residue, whereas β-II tryptase has a lysine residue. As is explained in more detail in Example 1b, amino acid 102 was mutated in the β-I tryptase clone pPIC9-HumTry, converting asparagine to lysine, thereby changing the amino acid sequence from that of β-I tryptase to that of β-II tryptase. The new clone was designated clone pPIC9-HumTryN102K. The gene was mutated with the GeneEditor in vitro Site Directed Mutagenesis Kit™ (Promega Corporation), following the kit directions. The oligonucleotide used for this mutation was SEQ. ID. NO. 7: (5'-GAGGAGC-CGGTGAAGGTCTCCAGCCAC-3'). The resultant mutated tryptase DNA, i.e., the recombinant β-II tryptase, is shown in SEQ. ID. NO. 8, and its amino acid sequence is described in SEQ. ID. NO. 9. The peptide of SEQ. ID. NO. 9 is cleaved to form the mature β-II tryptase, which has the amino acid depicted in SEQ. ID. NO. 11. The DNA that encodes the cleaved, mature β-II tryptase is shown in SEQ. ID. NO. 10.

As detailed in Example 1b, the mutation reactions were used to transform bacterial strain BMH71-18 (contained in the kit). Other strains that contain a transposon insertion in the mutS gene, such as ES 1301, can be used with equal success. BMH71-18 mutS competent cells are preferred. DNA was isolated from the cells and was used to transform JM109 *E. coli* cells. DNA isolated from the JM109 cells was digested with restriction enzymes to confirm the mutagenesis of amino acid 102.

Transform *Pichia* with the pPIC9-HumTryN102K DNA:

The expression construct pPIC9-HumTryN102K encoding the human β-II tryptase then was incorporated into a suitable eukaryotic host, as described above. A eukaryotic host must be used so that the expressed β-II tryptase is properly processed by the cell after translation. Post-translational intracellular processing by the eukaryotic host is critical to impart enzymatic activity to the mature protein. As noted above, the expression constructs can be incorporated into any suitable eukaryotic host, yeast being preferred. The preferred hosts include *Hansenula polymorpha, Kluyveromyces lactis, Pichia pastoris, Saccharomyces cerevisiae, Schizosaccharomyces pombe, Schwanniomyces occidentalis* and *Yarrowia lipolytica*. It is most preferred that the host be of the genus *Pichia*. From among *Pichia*, it is most preferred that the host cell be a *Pichia pastoris* cell having the characteristics of ATCC 20864 (strain GS115), SMD1168 (Invitrogen), or KM71 (Invitrogen). Example 2b details the transformation of *Pichia pastoris* strains SMD1168, GS115, and KM71 with the pPIC-HumTry N102K construct. The pPIC9-HumTryN102K DNA was digested with Sal I prior to transformation into the host.

Host cells are transformed by electroporation in a conventional fashion and screened as described above. If operationally linked to an inducible promoter, successfully transformed auxotrophs are screened in a medium containing the required inducer to initiate tryptase production as described above.

Best Expression Response:

Clones can be validated for the best expression response. For this, single colonies of various clones were transferred to 50 ml YPD broth cultures (contents/L: 20 g Peptone-Y, 10 g yeast extract-Y, 20 g dextrose, pH6.5 at 30° C.). Cells were grown overnight at 30° C. with shaking. The following day, the $A_{600}$ of the overnight cultures was checked. For each clone, cells (300 $A_{600}$ units) were centrifuged in a clinical centrifuge for 10 minutes at 2500 rpm. The cells were resuspended in 25 ml BMMY (buffered minimal methanol complex media; which is BMGY containing 0.5% methanol, but without 1% glycerol). BMGY is buffered minimal glycerol complex media, which contains 100 mM potassium phosphate, pH 6.0, 10 g/L yeast extract, 20 g/L peptone, 13.4 g/L yeast nitrogen base, 0.4 mg/L biotin, and 1% glycerol. Both BMMY and BMGY are commercially available from Invitrogen. The cells were transferred to 500 ml BMMY cultures. The $A_{600}$ of the inoculated cultures were then checked. The cells were grown overnight at 30° C. with shaking.

The following day, a 5 ml sample of each culture was removed, and the $A_{600}$ of each culture was checked. Each culture was fed 2.5 ml of methanol. The media was supplemented with 5 ml of 50 mg/ml heparin (prepared in BMMY). Cells were grown overnight at 30° C. with shaking. The following day, a 5 ml sample from each culture was removed. The $A_{600}$ of each culture was checked. Each culture was then fed another 2.5 ml of methanol. Cells were grown overnight at 30° C. with shaking. The following day, a 5 ml sample from each culture was removed, and the $A_{600}$ of each culture was checked. From an analysis of the $A_{600}$, the growth curves can be compared to each other. The activity data can also be compared.

End Uses for Enzymatically-Active Recombinant Proteolytic Tryptase:

A distinct advantage of the recombinant proteolytic tryptase described herein is that it is enzymatically active. Because the recombinant proteolytic tryptase is active, it can be used in any application which would otherwise require using a cadaveric tryptase.

For instance, because the recombinant proteolytic tryptase of the invention has the same biological activity as cadaveric tryptase, it can be used as an antigen to generate anti-human tryptase antibodies in various animals. This is done in well-known and conventional fashion by inoculating a test animal, such as a mouse, rat, rabbit, guinea pig, chicken, goat, or other animal, with an initial inoculation of the recombinant tryptase, followed by a series of booster injections. The injections initiate an immunogenic reaction in the animal, resulting in the production of polyclonal antibodies to the recombinant tryptase.

To isolate the antibodies, the IgG fraction of the blood serum (or from egg yolks in the case of avians) is isolated in standard fashion. With egg yolks, this can be accomplished utilizing a commercial product such as Promega Corporation's "EGGstract" ™ IgY Purification System (Promega Corporation, Madison, Wis. U.S.A.). There also are a number of other methods for isolating immunoglobulins from serum or egg yolks, such as other sequential precipitation methods, which are well known to those skilled in the field. See, for instance, Scopes, R. K. The conventional method of protein isolation, which is completely satisfactory to isolate anti-human tryptase antibodies, is to "salt out" the protein fractions by precipitation of the proteins from a salt solution. The IgY polyclonal antibodies from the serum of the test animal can be isolated using, for instance, chromatographical methods. Again, there are a number of methods well known to those skilled in the art for isolating immunoglobulins from serum or egg yolk samples.

In the same fashion, the recombinant proteolytic tryptase described herein can be used to generate monoclonal anti-human tryptase antibodies using conventional hybridoma technology. In this technology, a mouse or other test animal is immunized with the recombinant human tryptase to initiate the required immunogenic response. For murine-derived monoclonal antibodies, pristane-primed mice are widely utilized. Spleen cells from the immunized animals are then immortalized by fusion with an immortal cell line, such as a myeloma cell line. The hybrid cells are then serially-diluted, cultured, and screened for those cells which secrete antibodies specific for the recombinant tryptase. The monoclonal antibodies so formed can be used in any number of applications, such as assaying to detect human tryptase, epitope mapping of human tryptase, or for inhibiting tryptase activity for therapeutic or other applications. Other recombinant techniques of making antibody such as those described above can be used to make antibodies to the recombinant proteolytic tryptase.

The recombinant proteolytic tryptases of the present invention can also be used in drug screening for compounds which act as tryptase inhibitors, antagonists, agonists, etc. For example, to screen for tryptase inhibitors, the recombinant proteolytic tryptase of the present invention can be contacted with a putative tryptase inhibitor. The effectiveness of the inhibitor is then determined by measuring the loss of tryptase enzymatic activity as compared to a standard curve of tryptase activity.

Likewise, the same approach can be used to screen promising drug candidates for their effects on the enzymatic activity of proteolytic tryptase. This can be done with the recombinant proteolytic tryptase in solution phase. Because the subject recombinant proteolytic tryptase is enzymatically active, the effect of any given compound on the proteolytic tryptase can easily be determined by measuring the effect the compound has on the enzymatic activity of the proteolytic tryptase.

Other uses for the recombinant proteolytic tryptase include screening chemical libraries, peptide libraries, and the like. The recombinant proteolytic tryptase can also be used for in vitro, in vivo, and ex vivo testing of substances. Additionally, modeling can be done on the recombinant proteolytic tryptase.

The recombinant proteolytic tryptase can also be used to assay for the presence of proteolytic tryptase in biological or other solutions. For example, the recombinant tryptase can be used to develop enzyme-linked immunosorbent assays (ELISAs) for human tryptase. See, for example, U.S. Pat. No. 5,744,319 to Niles and Haak-Frendscho for a description of a double antibody-sandwich ELISA, which is incorporated herein by reference. ELISAs come in many different, but related formats, all of which are exceedingly well known to those skilled in the field. A format widely used due to its relative ease of use and wide linear response range is known as the double antibody-sandwich ELISA. The basic protocol for a double antibody-sandwich ELISA is as follows: A plate is coated with antibodies (called capture antibodies) specific for the immunoglobulin being assayed. In this case, the capture antibodies are polyclonal or monoclonal antibodies specific for the recombinant tryptase which are isolated as described above. The plate then is washed with a blocking agent, such as bovine serum albumin (BSA) to block non-specific binding of immunoglobulins to the test plate. The solution to be tested for the presence of tryptase then is incubated on the plate coated with the capture antibodies. The plate then is washed, incubated with detect antibodies, washed again, and incubated with a specific antibody-enzyme conjugate. After incubation, the unbound conjugate is washed from the plate and enzyme substrate is added. The presence of the bound antibody-enzyme conjugate results in a proportional color change which can be measured and quantified.

For detecting very low levels of proteolytic tryptase, levels which might be below the detection limit of a given assay, the recombinant proteolytic tryptase can be used in known quantities (or activities) to spike samples, thereby increasing the concentration of tryptase in the samples being assayed above the detection limit and into the linear response range of the assay being used.

Because the present invention enables the production of large amounts of enzymatically active recombinant proteolytic tryptase which can be extensively characterized and subjected to quality control measures, antibodies against the recombinant tryptase can be raised and utilized in any number of assay formats to detect the presence of tryptase and to measure the effect of different compounds on the enzymatic activity of tryptase.

The recombinant proteolytic tryptases that the invention provide can be used to study homotetramers of proteolytic tryptase. Previously, enzymatically-active proteolytic tryptases were made only in vivo, where the products from the various proteolytic tryptase genes (e.g., β-I and β-II) formed heterotetrameric proteolytic tryptases. That is, a single molecule of tetrameric, enzymatically-active proteolytic tryptase was made of different monomers. In contrast, in the proteolytic tryptases provided by the invention, a single, tetrameric molecule of enzymatically-active proteolytic tryptase is made with the same monomer (e.g., only β-I monomers make up the tetramer).

Furthermore, the enzymatically-active recombinant β-II tryptase can be used as a control in experiments to decipher the differences between β-I and β-II tryptase. This is especially useful in view of the fact that tryptase prepared from cadavers is never 100% pure. Instead, human cadaveric tryptase is a mixture of α-tryptase and the various forms of β-tryptase. Thus, the enzymatically-active recombinant β-II tryptase can be used as a control in experiments to decipher the differences between α-tryptase and the various forms of β-tryptase (see FIG. 3).

Active Site Mutants of β-Tryptase

The active sites of tryptase have been predicted to be located at seven loops (A, B, C, D, 3, 1, and 2) as shown in FIG. 1. To confirm this, mutations were made to amino acids 44, 91, and 194 as shown in FIG. 1. These three residues correspond to residues 74, 121, and 224 of SEQ. ID. NO: 52. Non-conserved changes were made in various amino acids. Amino acids 44, 91, and 194 were changed to alanine. However, amino acids can be mutated to any non-charged residue. According to molecular modeling, these single point mutations were not expected to disrupt the secondary structure.

As can be seen from FIG. 1, amino acid 44 (residue 74 of SEQ. ID. NO: 52) is located within the putative B loop, amino acid 91 (residue 121 of SEQ. ID. NO: 52) is located in the C terminus direction to loop C, and amino acid 194 (residue 224 of SEQ. ID. NO: 52) is within loop 1. Amino acids 44, 91, and 194 are called the catalytic triad. To determine whether the active sites for proteolytic tryptase include histidine at residue 44, asparagine at residue 91, and serine at residue 194, mutants in the putative active sites were generated with the QuikChange™ Site Directed Mutagenesis Kit (Stratagene, LaJolla, Calif.) (described in detail in Example 1c).

As detailed in Example 1c, the mutation reactions were used to transform bacterial strain Epicurian Coli® XL1-Blue supercompetent cells. The constructs were then transformed into a suitable eukaryote host as described in Example 2c. *Pichia* cells are preferred. Briefly, the DNA was first linearized. The linearized DNA was added to the *Pichia* GS 115 cells, and electroporated as described above. The transformed *Pichia* was screened for mut⁺ and mut⁵ phenotypes.

Specific Cleavage Activity of Active Site Mutants:

As is shown in Examples 4a–4b, the specific activity of the unpurified β-I and β-II tryptase having active site mutations was determined by the CBZ-Lys-Thiobenzl Ester cleavage assay. After the proteolytic tryptase was purified as detailed in Example 5, the specific activity was assayed again. As is detailed in Example 6b, the specific activity of the active site mutants of β-I and β-II tryptase was approximately 1000-fold less than the recombinant, enymatically-active β-I and β-II tryptase proteins.

Verification of Production of Tryptase by Active Site Mutants:

To verify that the lack of specific activity of the active site mutants of β-I and β-II tryptase was due to the mutations in the active site and not due to a lack of mature, proteolytic tryptase expression, the expression in the active site mutants was verified with Western blots using antibodies to β-tryptase as is detailed in Example 3b. As is shown in Example 7, gel filtration analysis of β-I and β-II tryptase and the S194A β-I tryptase active-site mutant further confirmed that the active site mutant was a tetramer.

End Uses of Active Site Mutants of Proteolytic Tryptase:

Uses for active site mutants of proteolytic tryptase include the following. Both in vitro and in Vivo activity studies have been conducted on tryptase. Many broad spectrum protease inhibitors are known to be efficacious in vitro, but highly toxic in vivo. Unfortunately, there is no known natural inhibitor of tryptase. Therefore, data interpretation is complicated in these in vivo studies. It is difficult to fully reconcile the physiological effects of excipient buffer (including NaCl, MES, buffer, glycerol, and heparin), protein load, endogenous contaminating pyrogen or small molecule *Pichia* allergen. The active site mutants provide an inhibited form of proteolytic tryptase. Thus, in vivo studies can be conducted with the active site mutants without the complications listed above. In vitro, ex vivo, and other studies can also be performed with the active site mutants. Additionally, the active site mutants can be used for modeling studies.

Furthermore, active site mutant of the tryptase enzymes can be used to supplement further these studies. Single amino acid substitutions at amino acids 44, 91, and 194 in both recombinant human β-I and β-II tryptase isoforms reduced the specific activity of the recombinant tryptase to less than 1% of the activity of unmutagenized enzyme. These reduced-activity proteolytic tryptases provide an ideal control for in vivo experimentation because they are highly purified and can be stored in the same manner as active enzyme preparations.

The active site mutants also provide a tool with which to investigate further the structural and functional properties of this unique protease, beyond the enzymatic activity.

EXAMPLES

The following Examples are included solely to provide a more complete understanding of the subject invention. The Examples do not limit the scope of the invention described and claimed herein in any fashion.

Generation of the Constructs:

Example 1a

Construction of Human β-I Tryptase Expression Vector

The 5' and 3' ends of the human β-I tryptase gene encoded by pBSHumTry (see Vanderslice et al., 1990) were modified via PCR using a pair of partially homologous oligonucleotide primers, SEQ. ID NO. 2 and SEQ. ID NO. 3. The modified tryptase fragment was ligated to the Xho I and Not I sites of pPIC9 (Invitrogen) downstream of the α-Factor secretion signal found on pPIC9 (see "S" in FIG. 2) to yield an expression construct designated pPIC9-HumTry. *E. coli* strain JM109 (Promega Corporation, Madison, Wis., U.S.A.) was transformed with the ligation mix using standard protocols (calcium chloride) to form a library of transformants. Transformants were screened for properly constructed pPIC9-HumTry constructs by restriction analysis of the plasmid DNA isolated from ampicillin-resistant colonies.

Example 1b

Construction of Human β-II Tryptase Expression Vector

Amino acid 102 of human β-I tryptase in pPIC9-HumTry was mutated from asparagine to lysine, changing the protein from human β-I tryptase to human β-II tryptase. The gene was mutated with the GeneEditor in vitro Site Directed Mutagenesis Kit (Promega Corporation), following the kit directions. The oligonucleotide used for this mutation was SEQ. ID. NO. 7, described above.

The mutation reaction was used to transform bacterial strain BMH71-18. Other strains containing a transposon insertion in the mutS gene, such as ES 1301, can be used with equal success. DNA was isolated from the cells and was used to transform JM109 *E. coli* cells. DNA isolated from the JM109 cells was digested with restriction enzymes to confirm the mutagenesis of amino acid 102.

Example 1c

Construction of H44A, D91A and S194A Mutants

For both β-I and β-II tryptase genes, mutant constructs were generated, with each one having a mutation in one of the three putative active sites. Each of the mutations changed the amino acid residue to alanine.

Using the QuikChange™ Site Directed Mutagenesis Kit (Stratagene, La Jolla, Calif.), site-directed mutagenesis was performed. Top and bottom strand oligos were paired for each amino acid. For the S194A mutation one pair of oligos was predicted to form a loop structure. Thus, two pairs of oligos (one predicted to form the loop structure and one, not) were tested separately. Both the pPIC9-HumTry (β-I tryptase) plasmid and the pPIC9-HumTry N102K (β-II tryptase) plasmids were mutated at three of the putative active sites. A separate mutant was generated for each site.

The following oligonucleotides were used for mutagenesis:

SEQ. ID. NO. 12, top strand for H44A: (5'-GTGCTGACCGCCGCGGCGTGCGTGGGACCGGAC-3');

SEQ. ID. NO. 13, bottom strand for H44A: (5'-GTCCGGTCCCACGCACGCCGCGGCGGTCAGCAC-3');

SEQ. ID. NO. 14, top strand for D91A: (5'-GCCCAGATCGGAGCGGCAATCGCCCTGCTGGAG-3');

SEQ. ID. NO. 15, bottom strand for D91A: (5'-CTCCAGCAGGGCGATTGCCGCTCCGATCTGGGC-3');

SEQ. ID. NO. 16, first top strand for S194A, which formed a loop at 44° C.: (5'-TGTCAAGGCGACGCCGGCGGACCTCTGGTG3');

SEQ. ID. NO. 17, first bottom strand for S194A: (5'-CACCAGAGGTCCGCCGGCGTCGCCTTGACA-3');

SEQ. ID. NO. 18, second top strand for S194A, which did not form a loop: (5'-CAAGGAGACGCCGGCGGACCACTGGTGT-3');

SEQ. ID. NO. 19, second bottom strand for S194A: (5'-GCACACCAGGGGCCCGCCGGCGTCGCCCTGGCATGA-3').

The mutants generated with the oligos above had the sequences shown in Table 1:

TABLE 1

| SEQ. ID. NO. | Description |
| --- | --- |
| 20 | β-II DNA for active site mutant H44A pre-cleavage |
| 21 | β-II amino acid for active site mutant H44A pre-cleavage |
| 22 | β-II DNA for active site mutant D91A pre-cleavage |
| 23 | β-II amino acid for active site mutant D91A pre-cleavage |
| 24 | β-II DNA for active site mutant S194A pre-cleavage (+loop) |
| 25 | β-II amino acid for active site mutant S194A pre-cleavage |
| 26 | β-II DNA for active site mutant S194A pre-cleavage (−loop) |
| 27 | β-II amino acid for active site mutant S194A pre-cleavage |
| 28 | β-II DNA for active site mutant H44A mature |
| 29 | β-II amino acid for active site mutant H44A mature |
| 30 | β-II DNA for active site mutant D91A mature |
| 31 | β-II amino acid for active site mutant D91A mature |
| 32 | β-II DNA for active site mutant S194A mature (+loop) |
| 33 | β-II amino acid for active site mutant S194A mature (+loop) |
| 34 | β-II DNA for active site mutant S194A mature (−loop) |
| 35 | β-II amino acid for active site mutant S194A mature (−loop) |
| 36 | β-I DNA for active site mutant H44A pre-cleavage |
| 37 | β-I amino acid for active site mutant H44A pre-cleavage |
| 38 | β-I DNA for active site mutant D91A pre-cleavage |
| 39 | β-I amino acid for active site mutant D91A pre-cleavage |
| 40 | β-I DNA for active site mutant S194A pre-cleavage (+loop) |
| 41 | β-I amino acid for active site mutant S194A pre-cleavage |
| 42 | β-I DNA for active site mutant S194A pre-cleavage (−loop) |
| 43 | β-I amino acid for active site mutant S194A pre-cleavage |
| 44 | β-I DNA for active site mutant H44A mature |
| 45 | β-I amino acid for active site mutant H44A mature |
| 46 | β-I DNA for active site mutant D91A mature |
| 47 | β-I amino acid for active site mutant D91A mature |
| 48 | β-I DNA for active site mutant S194A mature (+loop) |
| 49 | β-I amino acid for active site mutant S194A mature (+loop) |
| 50 | β-I DNA for active site mutant S194A mature (−loop) |
| 51 | β-I amino acid for active site mutant S194A mature (−loop) |

All mutants were transformed into the cells included in the QuikChange Kit: Epicurian Coli® XL1-Blue supercompetent cells. Kit instructions were followed with the following exceptions. The pPIC9HumTryN102K plasmid template was used at 16, 32, and 64 ng per reaction. Also, the reaction was cycled as described in the kit, except that the last extension was 18 minutes at 68° C.

Epicurian Coli® XL1-Blue supercompetent cells were transformed with the mutation reactions. From each mutation, nine colonies were picked and grown overnight in LB with 100 μg/ml ampicillin. Plasmids were isolated using Wizard S/V (Promega, Madison, Wis.). To confirm the mutations, restriction enzyme digests were conducted in 20 μl final volume with 5 μl of each DNA using Sac I or Nae I Turbo. DNA was then sequenced to verify the mutations.

Transformation of *Pichia pastoris* with the Constructs

Example 2a

Human β-I Tryptase

Fresh cultures of *Pichia pastoris* strains GS 115 (ATCC 20864) and KM71 (Invitrogen) were prepared for electroporation by extensive washing with 1M Sorbitol. Electrocompetent cells were mixed with aliquots of pPIC9-HumTry DNA produced according to Example 1a that had been digested with one of either Sal I, Bgl II, or Sac I, and transformed. Transformants were initially identified as His+ prototrophs on minimal media. Methanol utilization phenotypes were analyzed via replica plating on both minimal dextrose and minimal methanol grid plates.

Example 2b

Human β-II Tryptase

The pPIC9-HumTryN102K DNA was digested with Sal I. The digestion was incubated for 90 minutes at 37° C., and was stopped by incubating the mix at 65° C. The mixture was then ethanol precipitated, and the pellet was resuspended in 50 μl of water.

*Pichia* cells (SMD1168, Invitrogen; GS115, ATCC 20864; and KM71, Invitrogen) were transformed with the DNA by electroporation with the following protocol. Cuvettes were prechilled in the refrigerator. 80 μl of electrocompetent cells were transferred to the cuvettes. 10 μl of the Sal I cut DNA was added. The cells were pulsed according to the following parameters: gap equals 0.2 cm, voltage equals 1,500 volts, capacitance equals 25 μF, and resistance equals 200 Ω. One ml of prechilled 1M sorbitol was added. 200 μl of electroporated cells was spread on minimal dextrose plates. The plates were incubated at 30° C.

*Pichia* clones were screened for Mut+ and Mut$^S$ transformants as described in the Invitrogen *Pichia* Expression Manual.

Example 2c

H44A, D91A and S194A Mutants

The active site mutants were partially cut with Sac I. *P. pastoris* GS115 were transformed with the partially-cut active site constructs by electroporation and screened as is described in Example 2b.

Western Blot Analysis

Example 3a

Human β-I and β-II Tryptases

Figure 3:
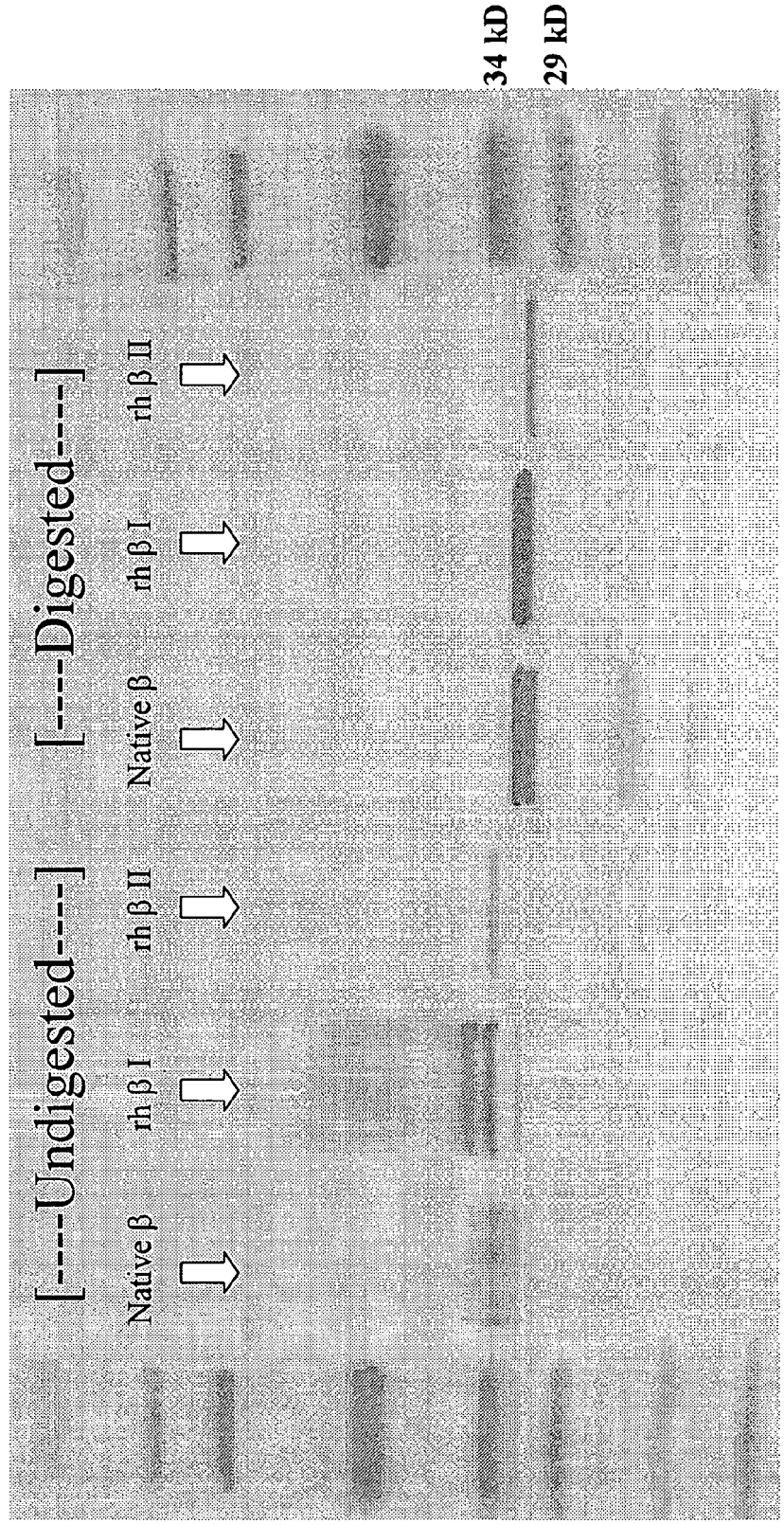
FIG. 3 is a Western blot of human β-I tryptase (rh β I), β-II tryptase (rh β II), and β-tryptase isolated from a cadaver (native β). The gel was visualized by probing with biotinylated anti-human tryptase AA5 monoclonal antibody (Promega Corporation). Glycosidase digestions with PGNase F were performed on the samples. The first three lanes contain the undigested tryptases. The second three lanes contain the digested tryptases. The glycosidase digestion yields a single tryptase core protein.

Glycosidase digestions with PGNase F were performed on β-I and β-II tryptases. FIG. 3 is a Western blot of β-I tryptase (rh β II) β-II tryptase (rh β II), and β-tryptase isolated from a cadaver (native β). The transferred tryptase was visualized by probing with biotinylated anti-human tryptase AA5 monoclonal antibody (Promega Corporation). The undigested tryptases (see the first three lanes) were compared to the digested tryptases (see the second three lanes). As shown in FIG. 3, the glycosidase digestion yields a single tryptase core protein for the recombinant proteolytic tryptases. Note the presence of likely degradation products of native tryptase.

Figure 4:
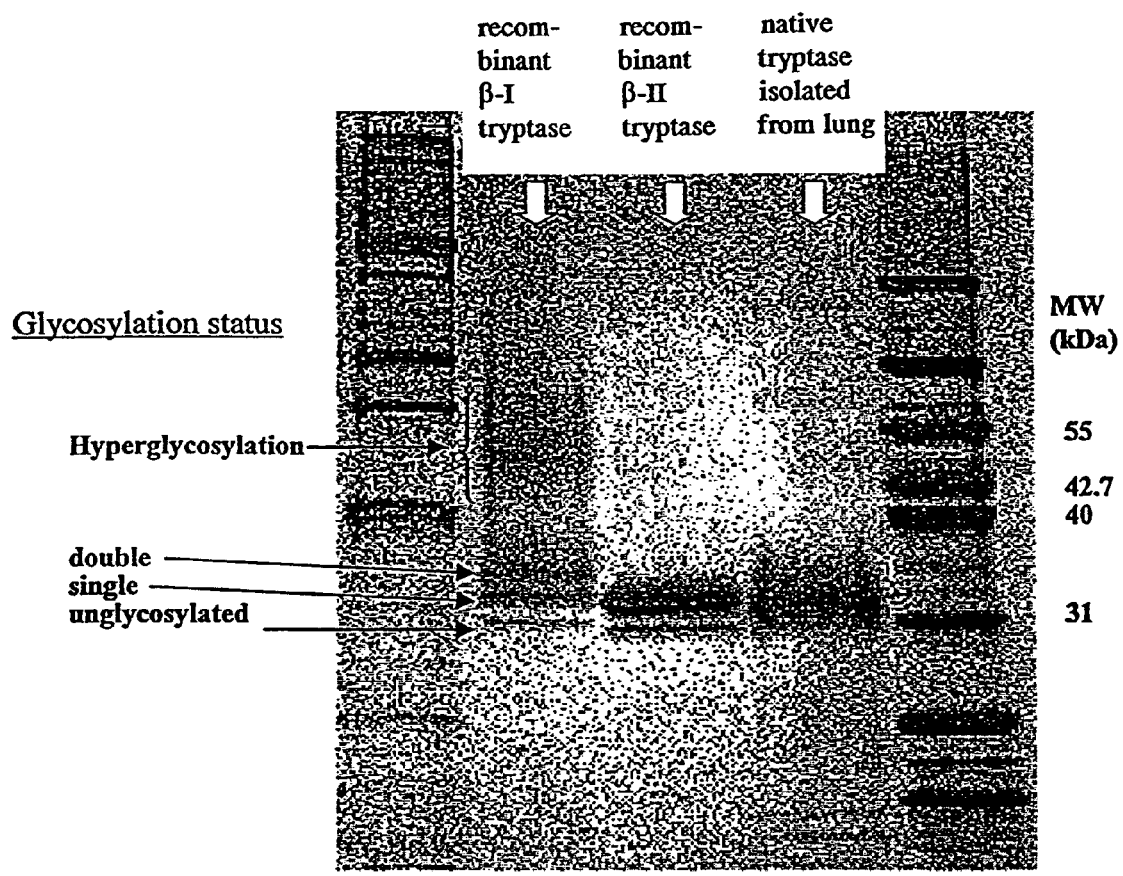
FIG. 4 is a COOMASSIE-brand dye stained SDS-PAGE of recombinant human β-I and β-II tryptases and native tryptases showing the glycosylation status of the proteins.

Recombinant β-I tryptase, recombinant β-II tryptase, and cadaveric lung tryptase were loaded onto a COOMASSIE®-stained SDS PAGE to show the glycosylation status of the proteins. Referring to FIG. 4, the β-II tryptase generated from pPIC9-HumTryN102K has one less glycosylation site than recombinant β-I tryptase. When digested with either PNGase F or Endo H, the β-II tryptase generated from pPIC9-HumTryN102K behaves like β-I tryptase derived from pPIC9-HumTry tryptase (reduced to 1 core) (data not shown). Cadaveric tryptase is not digested by addition of Endo H (data not shown).

Example 3b

H44A, D91A, and S194A Mutants

Figure 5:
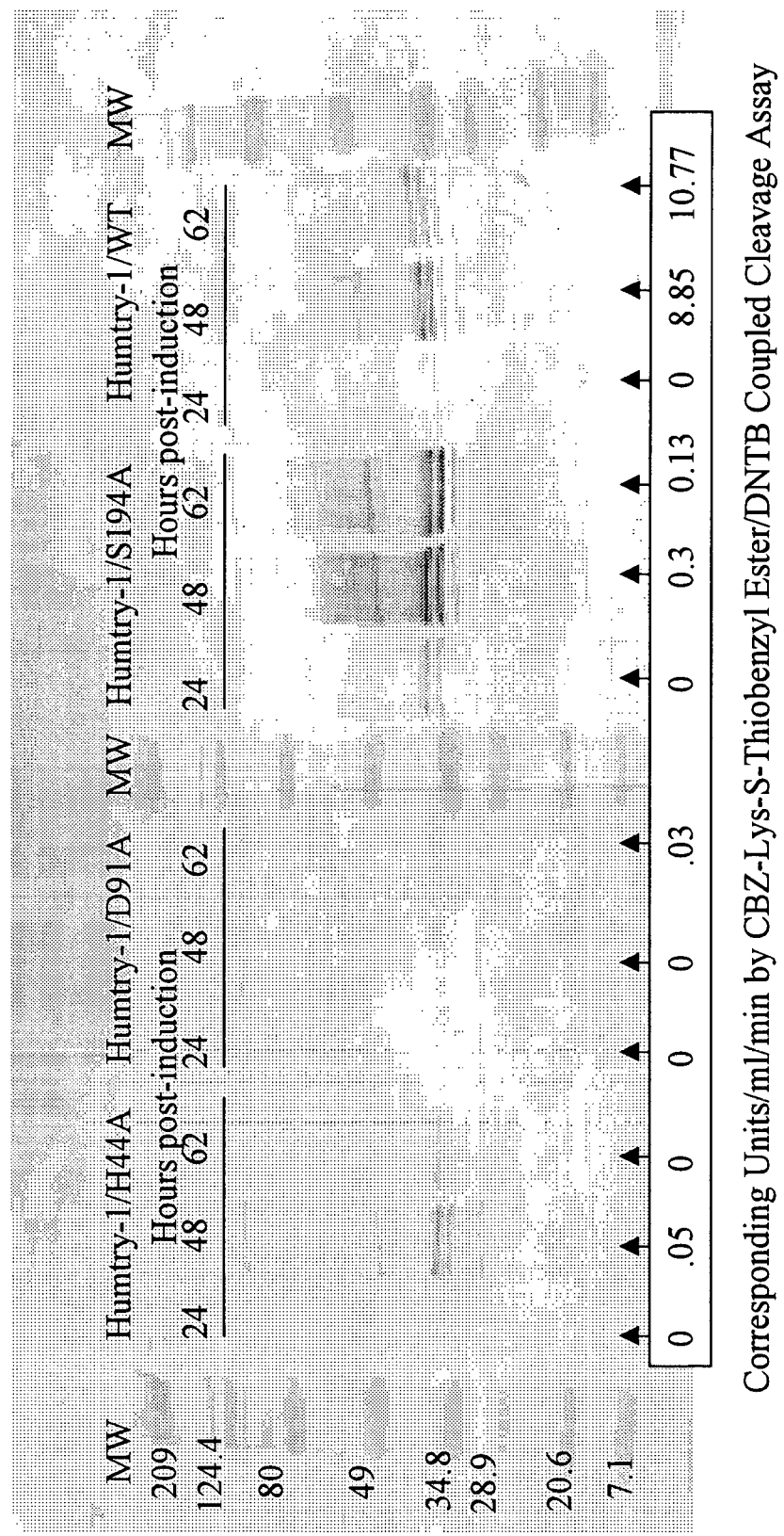
FIG. 5 is a Western blot of *Pichia pastoris* fermentation induction of human β-1 tryptase and two of its active site mutants (H44A and S194A). The gel was visualized by probing with biotinylated anti-human tryptase AA5 monoclonal antibody (Promega Corporation). A CBZ-Lys-S-Thiobenzyl Ester/DNTB Coupled Cleave Assay was performed on the loaded samples. The corresponding units/ml/min from the Assay are shown at the bottom of the gel.

FIG. 5 is a Western blot of *Pichia pastoris* fermentation induction of β-I tryptase and two of its active site mutants (H44A and S194A). The gel was visualized by probing with biotinylated anti-human tryptase AA5 monoclonal antibody (Promega Corporation). Although glycosylation studies were not performed on the active site mutants, as is shown in FIG. 5, the active site mutants migrated at the same molecular weights as their active counterparts.

Enzyme Assay (with Unpurified Enzyme)

Example 4a

Human β-I Tryptase and H44A and S194A Mutants Thereof

Unpurified samples from the active site mutants H44A and S 194A of β-I tryptase and the recombinant β-I tryptase were analyzed with the CBZ-Lys-S-Thiobenzyl Ester/DNTB Coupled Cleavage Assay. The results of the assay (in units/ml/min) are shown at the bottom of the gel of FIG. 5.

Example 4b

Human β-II Tryptase and S194A Mutant Thereof

Figure 6:
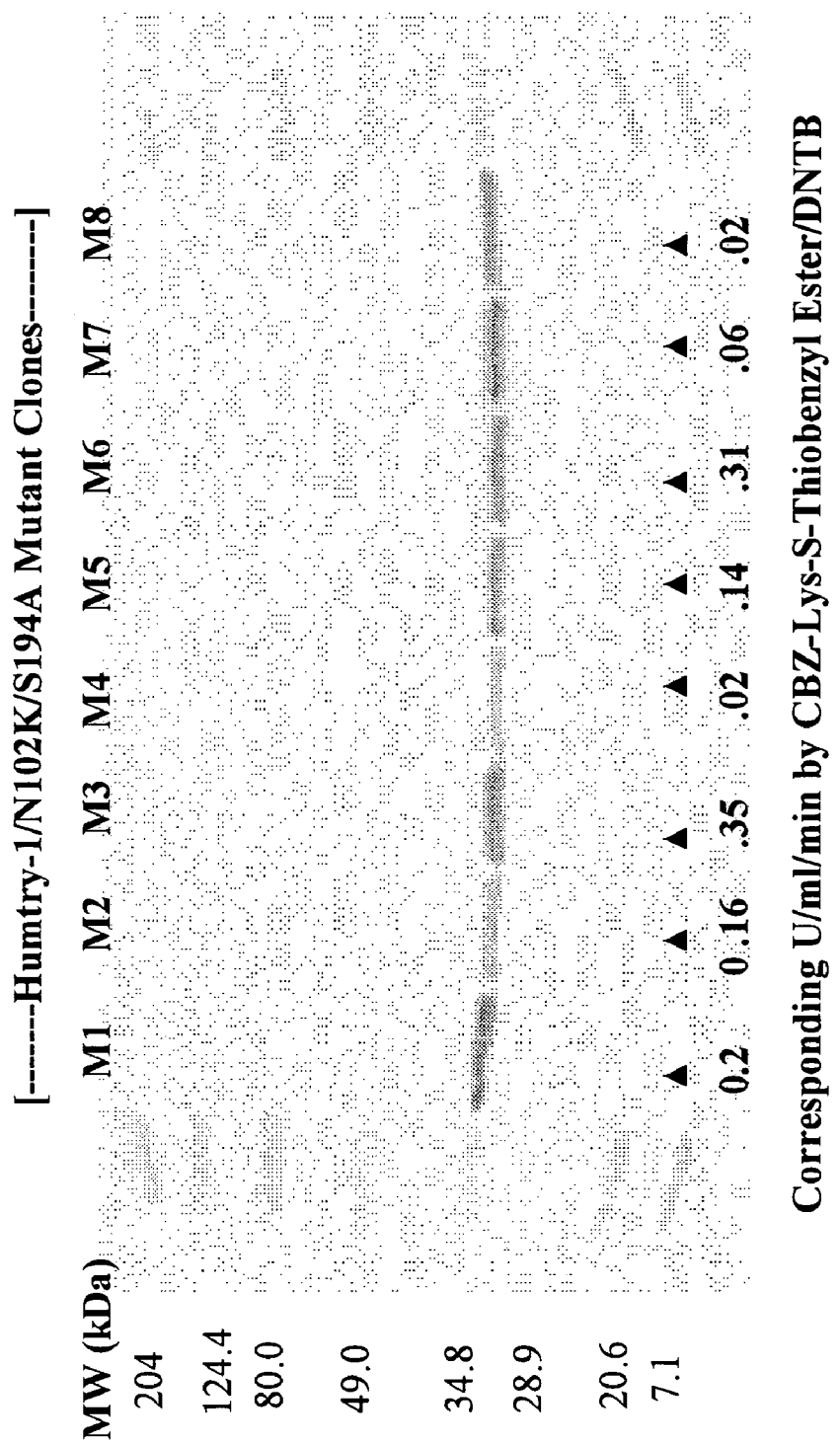
FIG. 6 is a Western blot of *Pichia pastoris* induction supernatant at 64 hours from eight different human β-II S194A active site mutant clones. A CBZ-Lys-S-Thiobenzyl Ester/DNTB coupled cleavage assay was performed on the loaded samples. The corresponding units/ml/min from the assay are shown at the bottom of the gel.

*Pichia pastoris* transformed with the active site mutant S 194A of β-II tryptase was grown and the tryptase induced. FIG. 6 is a Western blot of the *Pichia pastoris* induction supernatant at 64 hours from this clone. A CBZ-Lys-S-Thiobenzyl Ester/DNTB coupled cleavage assay was performed on the loaded samples. The corresponding units/ml/min from the Assay are shown at the bottom of the gel.

Tryptase Purification Scheme

Example 5

Purification of Recombinant Proteolytic Tryptases

The following example was performed on a β-I tryptase clone. This purification scheme was also used on β-II tryptase and active site mutations of both β-I and β-II tryptase.

The *Pichia pastoris* clone expressing β-I tryptase was grown in BMMY medium in a fermentor at 30° C. with a stirring rate of 250 revolutions per minute. The pH of the medium was maintained at 5.0–5.1 and expression was induced by the addition of methanol to 0.5% (v/v). After 72 h. the cell-free medium was collected by centrifugation at 400 g to pellet the cells, then stored at −70° C. Purification of β-I tryptase was begun with 112 ml of cell-free medium containing β-I tryptase, which was thawed at 37° C. in a shaking incubator and assayed for activity. All subsequent enzyme purification steps were conducted at room temperature. Established hydrophobic and heparin-binding properties of cadaveric human lung tryptase were exploited to devise a simple scheme for the affinity purification of β-I tryptase. The supernatant was made 2.0 M in $(NH_4)_2SO_4$ by slowly adding solid with magnetic stirring over a 30 minute period. After centrifugation at 20,000 g for 15 minute the supernatant was sampled and assayed for activity. The supernatant containing 2 M $(NH_4)_2SO_4$ was then mixed with a 60 ml bed volume of Toyopearl butyl 650 M hydrophobic interaction gel matrix pre-equillibrated with 10 mM Mes/2 M $(NH_4)_2SO_4$/0.5 M NaCl/10% (v/v) glycerol/0.02% $NaN_3$ (pH 6.1). This mixture was shaken gently at room temperature for 1 hour to allow binding of the enzyme.

Periodically the gel matrix supernatant was sampled and assayed to determine binding efficiency. When no appreciable activity remained unbound, the resin was loaded in a column and washed with 1 liter of pre-equilibration buffer. The bound protein was eluted from the column by the addition of 10 mM Mes/0.2 M NaCl/10% (v/v) glycerol/0.02% $NaN_3$ (pH 5.5). Fractions (5 ml) were collected and assayed for activity, and those containing more than 2 units/ml were pooled. Although several non-tryptase proteins, including a green *Pichia* pigment, were co-purified during butyl column chromatography, this step served to concentrate the β-I tryptase activity while removing residual components in the *Pichia* fermentation medium. Active fractions from the butyl column were pooled, assayed, diluted 1:2 in nanopure water to reduce the salt concentration and mixed with a 60 ml bed volume of Toyopearl AF-Heparin 650 M, pre-equilibrated with 10 mM Mes/0.2 M NaCl/10% (v/v) glycerol/0.02% $NaN_3$ (pH 5.5).

During a 1 hour incubation at room temperature the supernatant was asayed periodically to determine binding efficiency. When no appreciable activity remained unbound, the resin was loaded in a column and washed with 1 liter of pre-equilibration buffer. Enzyme elution was achieved with 10 mM Mes/2 M NaCl/10% (v/v) glycerol/0.02% $NaN_3$ (pH 6.1). Fractions (5 ml) were collected and those containing at least 2 units/ml activity were pooled. After assay for activity, the β-I tryptase was dialysed and concentrated with an AMICON-brand stirred-cell concentrator equipped with a 10 kDa cut-off membrane. The purified β-I tryptase was stored in the heparin column elution buffer.

The heparin affinity column provided the greatest enrichment of β-I tryptase activity. An SDS/PAGE analysis of the purified β-I tryptase showed that the purified β-I tryptase contained two major bands with estimated molecular masses of 35,900 and 34,200 Da, a faint band at 33,000 Da and a diffuse region at approximately 50,000 Da. Image analysis of band intensities and areas showed that the two major bands accounted for more than 90% of the total reactive protein. The specific activity of the purified β-I tryptase was consistently greater than 1000 units/mg by an α-N-benzyloxycarbonyl-lysine thiobenzyl ester cleavage assay, which was approximately twice that of pure, fully active natural cadaveric human lung tryptase. The concentration of β-I tryptase was calculated by taking 27,500 Da as the molecular mass of the unglycosylated protein subunits, and a $A_{280}$ (1%) of 28.1 as determined for pure cadaveric human lung tryptase. Active-site titrations with the fluorescent 4-methylumbelliferyl p-guanidinobenzoate titrant showed that two preparations of β-I tryptase contained 94% and 96% active subunits. Two preparations of cadaveric human lung tryptase titrated at the same time contained 88% and 96% active sites.

Enzyme Assay (with Purified Enzyme)

Example 6a

Human β-I Tryptase

In this Example, the yield and activity of purified tryptase from a 112 ml sample of media from a fermentation of the β-I tryptase clone GS 115/HumTry 5–37 is presented. Specific activity was determined by the CBZ-Lys-S-Thiobenzyl Ester/DNTB coupled cleavage assay. Table 2 summarizes the results. This Example demonstrates the ease of purification and high recovery of tryptase using the subject invention:

TABLE 2

Purification Data from 112 ml conditioned media preparation

| Step | Total Protein ($A_{280}$) | Total Activity (Units) | Specific Activity (Units/mg) | Yield (%) |
| --- | --- | --- | --- | --- |
| Media: raw supernatant | 3424 | 732 | 0.21 | 100 |
| Butyl HIC resin | 68.7 | 721 | 10.5 | 98.5 |
| Heparin resin | 0.69 | 817 | 1177 | 111 |

Example 6b

Active Site Mutants of β-I and β-II Tryptase

Purified tryptase from β-I tryptase and β-II tryptase and their respective S 194A active site mutants were assayed by CBZ-Lys-Thiobenzyl Ester/DNTB assay. Results showed that the β-I and β-II tryptase had activity, whereas active site mutants of β-I and β-II tryptase had minimal or no activity, suggesting that the amino acids 44, 91, and 194 were imperative for proteolytic tryptase activity.

The specific cleavage activity of purified enzyme from both β-I and β-II tryptase and active site mutants thereof were determined by CBZ-Lys-Thiobenzyl Ester/DNTB assay. Table 3 summarizes the results.

TABLE 3

Specific Activity of Proteoltyic Tryptases (β-I and β-II) and S194A Active Site Mutants Thereof:

| Proteolytic Tryptase | Specific Activity (U/mg) |
| --- | --- |
| β-I | 1300 |
| β-I S194A active site mutant | 1.85 |
| β-II | 1950 |
| β-II S194A active site mutant | 1.1 |

Clearly, the results shown in Table 3 show the obliteration of the specific cleavage activity due to the active site mutations.

To verify that expressed tryptase active site mutants lacked activity due to the active site mutations and not to a lack of expression, SDS-PAGE were run on the active site mutants (H44A and S194A) of β-I tryptase and the enzymatically-active form of recombinant β-I tryptase. Proteins were transferred to membranes and blotted with biotinylated anti-human tryptase AA5 monoclonal antibody (Promega Corporation), as described above. FIG. 5 shows the Western blot results of this study, which demonstrates that the active site mutants express tryptase protein. Thus, the lack of specific activity in these mutants is due to the mutation of the active sites and not due to a lack of protein production.

Example 6c

Comparision of Kinetics Between Recombinant β-I Tryptase and Human Cadaveric Tryptase In this Example, the kinetics of the recombinant human β-I tryptase according to the present invention (rHT) were compared to the kinetics of cadaveric human tryptase isolated from lung (HLT). The results are shown in Table 4:

TABLE 4

Kinetic Data — rHT v. HLT:

| | $K_m$ ($\mu M$) | $k_{cat}$ ($S^{-1}$) | $k_{cat}/K_m$ ($M^{-1} S^{-1}$) |
| --- | --- | --- | --- |
| rHT (β-I) (pPIC9-HumTry) | 67 | 110 | $1.64 \times 10^6$ |
| HLT (cadaveric) | 55 | 46 | $0.84 \times 10^6$ |

Example 6d

$K_m$ Determination of the Recombinant β-I and β-II Tryptase

The $K_m$ of the recombinant β-I and β-II tryptase isoforms were determined by both the Lineweaver-Burk Plot (LBP) and the Eadie-Hofstee Plot (EHP). The values obtained were: tryptase β-I=36 $\mu M$ (LBP) and 24.5 $\mu M$ (EHP); and β-II tryptase=30 $\mu M$ (LBP) and 29.1 $\mu M$ (EHP).

Gel Filtration Assay

Example 7

Figure 7:
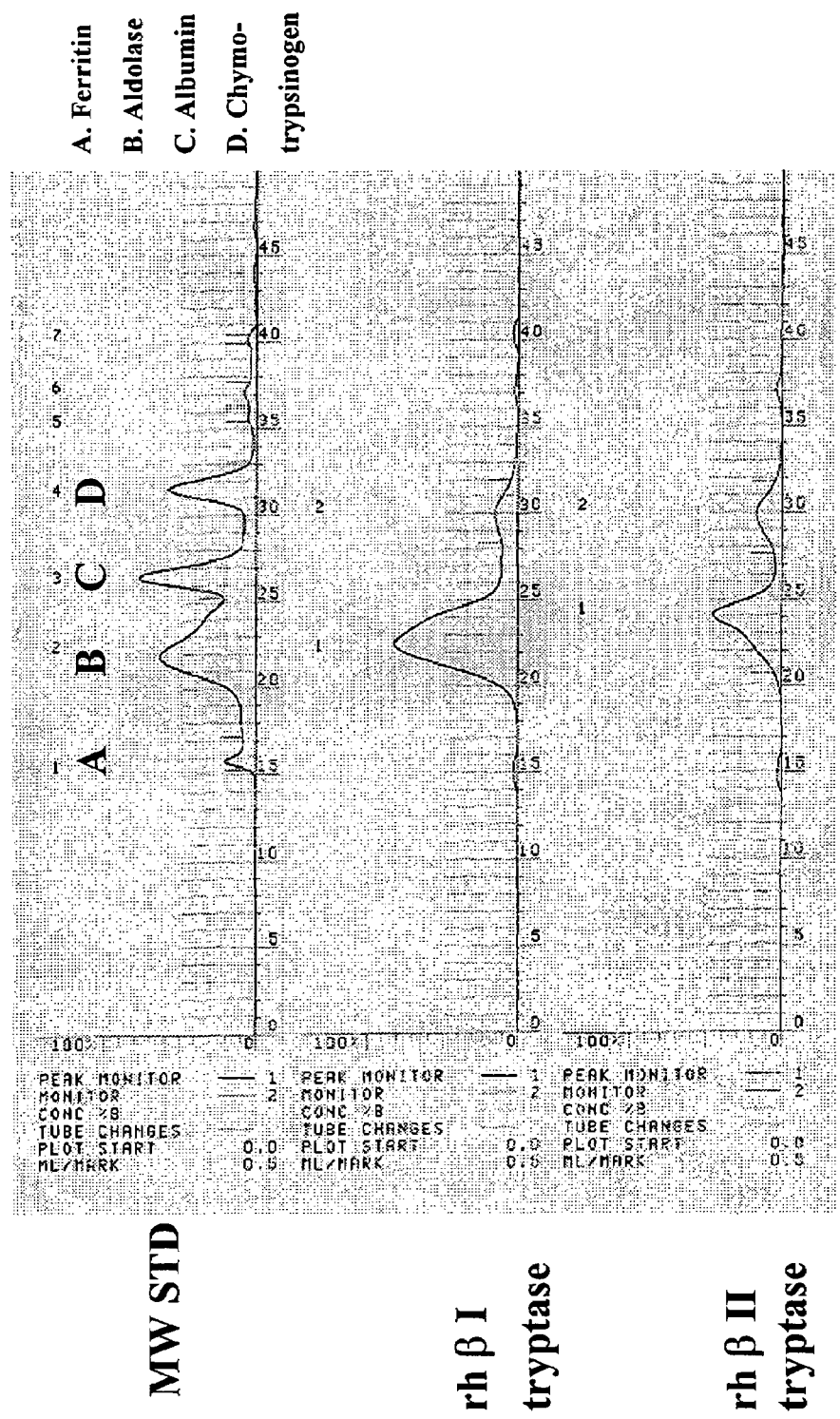
FIG. 7 shows molecular weight determinations for human β-I and β-II tryptase and a β-I tryptase mutant, S194A, by gel filtration.

Gel Filtration of β-I and β-II Tryptases and a β-I Tryptase Active Site Mutant Gel filtration analysis of the β-I and β-I tryptases and a β-I tryptase active site mutant was conducted to confirm further the tetrameric structure of these recombinant homomeric enzymes. FIG. 7 shows that the β-I and β-II tryptases and the S194A β-I tryptase active site mutant all have the same molecular weight, confirming that all were tetramers. Because there are no known natural physiological inhibitors of tryptase, the enzymes are thought to be regulated by disassociation from the active tetrameric form to the inactive disassociation products. See Schwartz L. and Bradford T. (1986). Therefore, it was important to correlate the β-I and β-II tryptase activity to the tetrameric form as well as to confirm that the mutation introduced in the β-I tryptase effected the enzyme's catalytic site, not its ability to form a tetramer.

Inhibition Assay:

Example 8a

β-I and β-II Tryptase Inhibition with AEBSF

A study was done to determine whether AEBSF (A.G. Scientific Inc., San Diego, Calif.), an inhibitor of serine proteases, inhibits recombinant human β-I and β-II tryptase and to determine if there were any inhibition differences between the two isoforms. Samples of β-I and β-II tryptase at 200 μg/ml were treated with either 0.1 mM or 1.0 mM (final) AEBSF in water and monitored after a 60 minute period by the CBZ-Lys-Thiobenyl Ester/DNTB coupled cleavage assay.

Figure 8:
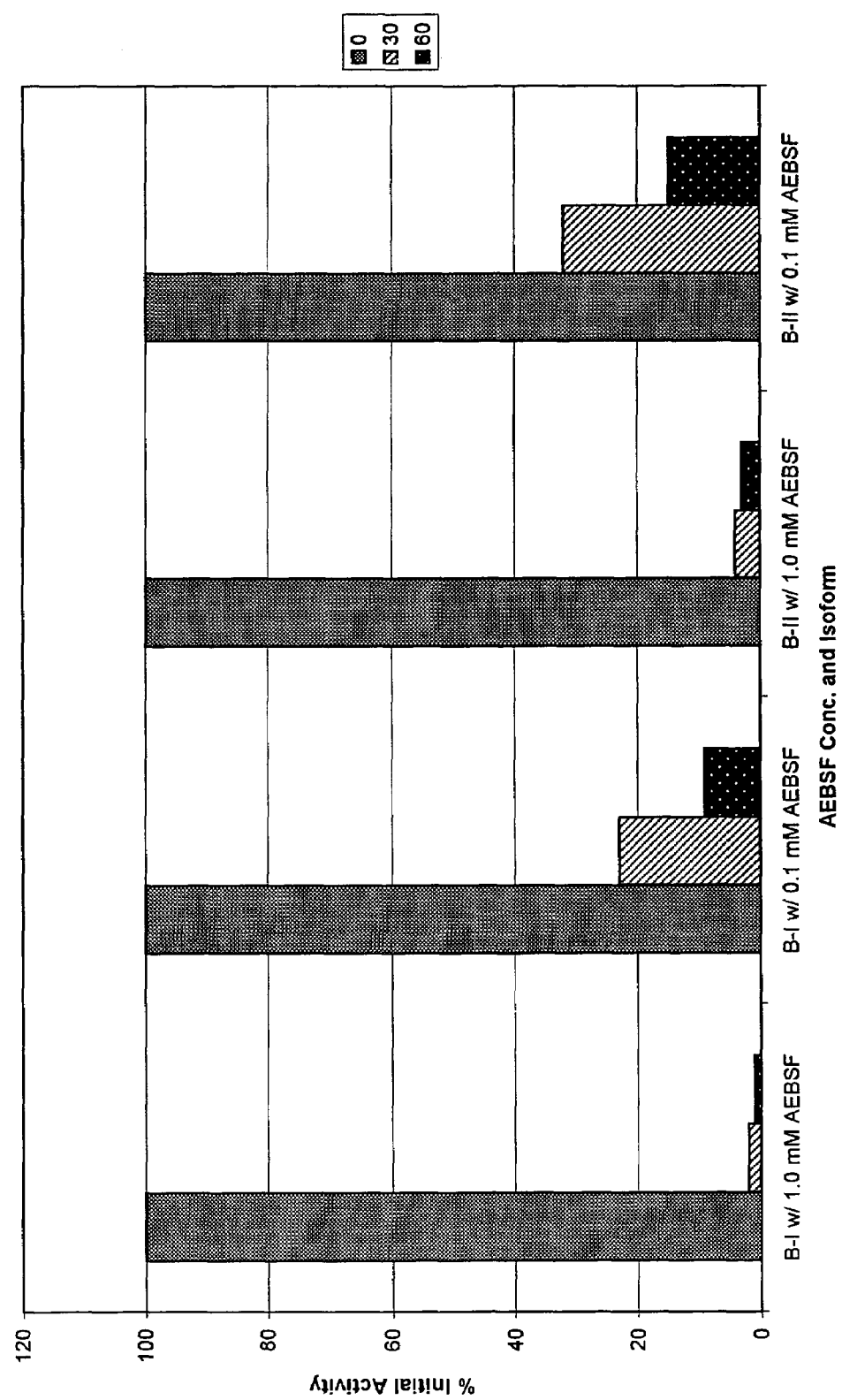
FIG. 8 is a graph illustrating the inhibition of human β-I and β-II tryptase by the irreversible serine protease inhibitor AEBSF.

As FIG. 8 shows, AEBSF is a very potent inhibitor of the recombinant human isoforms, particularly when used at 1 mM final concentration. No apparent differences between the two isoforms were found.

Example 8b

ELMIRON™ Assay

ELMIRON™ (Alza, Mountain View, Calif.) is a drug that lessens the symptomology of inflammation in the bladder and gastrointestinal tract (GI). It is believed that tryptase mediates a great deal of inflammation in the bladder and the GI. Thus, ELMIRON™ was tested for its direct effect on the enzymatic inhibition of recombinant β-II tryptase generated from pPIC9-HumTryN102K by titrating the drug on tryptase.

β-II tryptase was diluted into 201 g per ml fractions in 10 mM MES, 0.2 M NaCl, and 0.5 mg/ml heparin, pH 6.1, in 10 full dilutions of ELMIRON™ (suspended in water pH 6.0 at a stock concentration of 50 mg/ml). Various concentrations (25, 2.5, 0.25 and 0.025 mg/ml) were incubated with the β-II tryptase for 3 hours. Activity was assayed by CBZ-Lys-Thiobenzl Ester/DNTB coupled cleavage. It was found that ELMIRON™ did not inhibit β-II tryptase at the tested concentration range of 25 to 0.025 mg/ml.

Fibrinogen Cleavage Assay

Example 9

The Fibrinogenolytic Activity of Recombinant and Native β-tryptases

Figure 9:
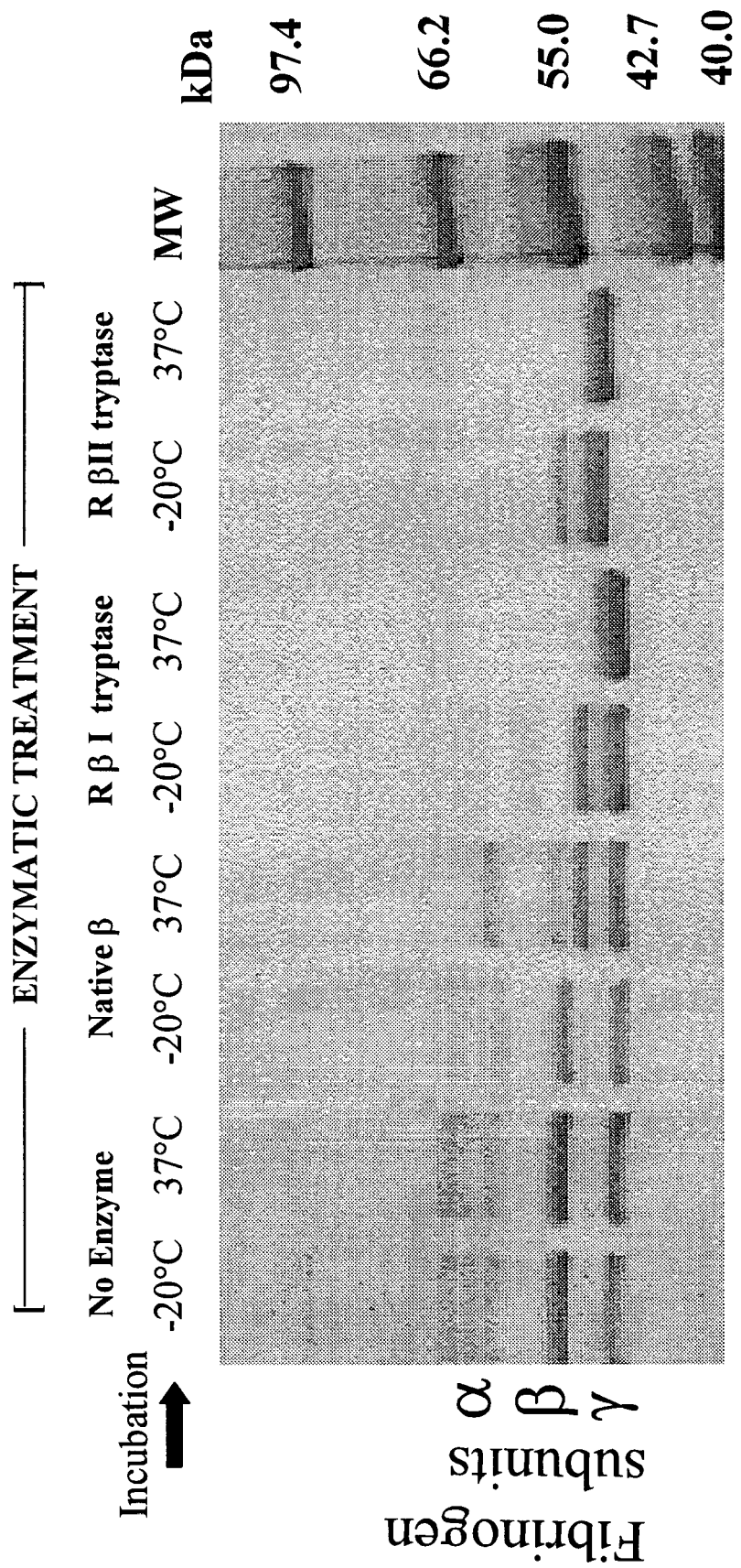
FIG. 9 shows a bioassay comparison of the cleavage and inactivation of fibrinogen by human β-tryptases.

Referring to FIG. 9, purified native and recombinant β-tryptases were evaluated for their capacity to metabolize human fibrinogen as described by Schwartz et al. (1985). Lyophilized fibrinogen was resuspended at a concentration of 1.0 mg/ml in 10 mM Tris, pH 7.4, containing 10 mM $CaCl_2$ and 150 mM NaCl with 0.5 mg/ml heparin. The fibrinogen master mix was divided into four 100 ml aliquots and either 5 μg recombinant β-I tryptase (R βI tryptase), recombinant β-II tryptase (R βII tryptase), or native β-tryptase (Native β) was added to one of three tubes. The remaining tube served as a control (no enzyme). The tubes containing the tryptase and fibrinogen were further divided into two tubes with one incubated at −20° C. and the other at 37° C. for a period of 60 minutes. The reactions were then analyzed by loading 2 μg equivalents of protein on a 4–20% Tris Glycine SDS-PAGE gel by standard electrophoretic methods. The gel was stained by Gel Code, dried, and imaged by scanning.

As FIG. 9 shows, the fibrinogen α, β, γ subunits were not degraded in the absence of tryptase enzyme with either incubation treatment. The α and β subunits were efficiently hydrolyzed by the recombinant β-I and β-II tryptase enzymes even during cold incubation. Native β-tryptase was less efficient at fibrinogeneolysis, but this was expected due to overall lower specific activity with synthetic substrates in comparison to the recombinant enzymes.

It is understood that the recombinant human tryptase and the methods to obtain the recombinant human tryptase are not confined to the particular reagents, host organisms, and genetic manipulations expressly illustrated and described herein, but embrace all modified and equivalent forms thereof as come within the scope of the attached claims.

BIBLIOGRAPHY

Blom, T. and Hellman, L. (1993), *Scand. J. Immunol.* 37:203–208.

Buckholz, R. G. and Gleeson, M. A. G. (1991), *Biotechnology* 9:1067–1072.

Chan, H.; Elrod, K. C.; Numerof, R. P. Sideris, S; and Clark, J. M. (1999), *Protein Express. & Purif.* 15:251–257.

Clark J. M.; Abraham, W. M.; Fishman, C. E.; Foreza, R. Ahmed, A.; Cortes, A.; Warne, R. L.; Moore, W. R; and Tanaka, R. D. (1995), *Am. J. Respir. Crit. Care Med.* 152:2076–2083.

Holgate S. T. and Church, M. K. (1992), *Br. Med. Bull UK* 48:40–50.

Huang C.; Li, L.; Krilis, S. A.; Chanasyk, K.; Tang, Y.; Li, Z.; Hunt, J. E.; and Stevens, R. L. (1999), *J. Biol. Chem.* 274:19670–19676.

Faber K. N.; Harder, W.; Ab, G.; and Veenhuis, M. (1995), *Yeast* 11:1331–1344.

Harvima, I. T.; Schechter N. M.; Harvima, R. J.; and Fräki, J. E. (1988) Human Skin Tryptase: Purification, Partial Characterization and Comparison with Human Lung Tryptase, *Biochimica et Biophysica Acta,* 957:71–80.

Huang, C.; Li, L.; Krilis, S. A.; Chanasyk, K.; Tang, Y.; Li, Z.; Hunt, J. E.; and Stevens, R. L. (1999) Human Tryptase α and β/II are Functionally Distinct Due, in Part, to a Single Amino Acid Difference in One of the Surface Loops that Forms the Substrate-binding Cleft, *J. Biol. Chem.* 274:19670–19676.

Huang, C.; Guillermo, M.; Vagi, A.; Chanasyk, K.; Ferrazzi, M.; Burklow, C.; Qiu, W.; Feyfant, E.; Sali, A.; and Stevens, R. L., (2000) Formation of Enzymatically Active, Homotypic, and Heterotypic Tetramers of Mouse Mast Cell Tryptases, *J. Biol. Chem.* 275:351–358.

Ide, H.; Itoh, H.; Tomita, M.; Murakumo, Y.; Kobayashi, T.; Maruyama, H.; Osada, Y.; and Nawa, Y. (1995), *J. Biochem.* 118:210–215.

Miller, J. S.; Moxley, G.; and Schwartz, L. B. (1990), *J. Clin. Invest.* 86:864–870.

Niles, A. L.; Maffitt, M.; Haak-Frendscho, M.; Wheeless, C. J.; and Johnson, D. A. (1998), Recombinant Human Mast Cell Tryptase: Stable Expression in *Pichia pastoris* and Purification of Fully Active Enzyme, Biotechnol. Appl. Biochem. 28:125–131.

Nilsson and Schwartz (1994), Mast-Cell Heterogeneity: Structure and Mediators, Blackwell Scientific Publications, Boston, pp. 195–208.

Pallaoro, M.; Fejzo, M. S.; Shayesteh, L; Blount, J. L.; and Caughey, G. H. (1999), Characterization of Genes Encoding Known and Novel Human Mast Cell Tryptases on Chromosome 16p13.3, *J. Biol. Chem.* 6:3355–3362.

Sakai K.; Long, S. D.; Dove-Pettit, D. A.; Cabral, G. A.; and Schwartz, L. B. (1996), *Protein Express. & Purif.* 7:67–73.

Sambrook, J.; Fritsch, E. F.; and Maniatis, T. (1989), *Molecular Cloning: A Laboratory Manual*; Cold Spring Harbor Laboratory Press: New York, N.Y.

Schwartz L. B.; Bradford, T. R.; Littman, B. H.; and Wintroub, B. U. (1985), *J. Immun.* 135:2762–2767.

Schwartz L and Bradford T. (1986) Regulation of tryptase from human lung mast cells by heparin: Stabilization of the active tetramer, *J. Biol. Chem.* 256: 7372–7379.

Schwartz (1995), Structure and Function of Human Mast Cell Tryptase, *Biological and Molecular Aspects of Mast Cell and Basophil Differentiation and Function*, chapter 14:161–173, Raven Press, Ltd: New York.

Scopes, R. K., (1994), Protein Purification, Principles and Practice, Springer-Verlag: New York.

Smith, T. J.; Hougland, M. W.; and Johnson, D. A. (1984), *J. Biol. Chem.* 259(17):11045–11051.

Sommerhoff, C. P.; Bode, W.; Pereira, P. J. B.; Stubbs, M. T.; Stürzebecher, J.; Piechottka, G. P.; Matschiner, G.; and Bergner, A. (1999), "The Structure of the Human βII-tryptase Tetramer: Fo(u)$_r$ Better or Worse," *Proc. Natl. Acad. Sci. USA* 96:10984–10991.

Vanderslice P.; Ballinger, S. M.; Tam, E. K.; Goldstein, S. M.; Craik, C. S.; and Caughey, G. H. (1990), *Biochemistry* 87:3811–3815.

Wung, J. L. and Gascoigne, R. J. (1996), *BioTechniques* 21:808–812.

What is claimed is:

1. A DNA expression construct comprising, in 5' to 3' order: a promoter, the promoter operationally linked to a secretion signal sequence, the secretion signal sequence operationally-linked to a DNA sequence encoding a proteolytic tryptase as shown in FIG. 1 having an active site mutation at an amino acid position selected from positions 44, 91, and 194, and wherein the expression construct drives expression of a mature proteolytic tryptase that lacks enzymatic activity in eukaryotic host cells transformed to contain the expression construct, the lack of enzymatic activity being due to the active site mutation.

2. The DNA expression construct according to claim 1, wherein the DNA sequence encoding the proteolytic tryptase having an active site mutation encodes skin tryptase.

3. The DNA expression construct according to claim 1, wherein the DNA sequence encoding the proteolytic tryptase having an active site mutation encodes lung tryptase.

4. The DNA expression construct according to claim 1, wherein the DNA sequence encoding the proteolytic tryptase having an active site mutation encodes a human proteolytic tryptase.

5. The DNA expression construct according to claim 1, wherein the active site mutation changes a native amino acid to a non-charged amino acid.

6. The DNA expression construct according to claim 5, wherein the active site mutation changes a native amino acid to an alanine.

7. The DNA expression construct according to claim 1, wherein the secretion signal sequence encodes a KEX2 cleavage site.

8. The DNA expression construct according to claim 1, wherein the secretion signal sequence includes a 3' terminus encoding amino acid residues Leu-Glu-Lys-Arg.

9. The DNA expression construct according to claim 1, wherein the promoter is a constitutive promoter.

10. The DNA expression construct according to claim 1, wherein the promoter is an inducible promoter.

11. A DNA expression construct comprising, in 5' to 3' order: a promoter selected from the group consisting of AOX1, GAP, MOX, FMD, ADH, LAC4, XPR2, LEU2, GAM1, PGK1, GAL 7, GADPR, CYC1, and CUP1, the promoter operationally linked to a secretion signal sequence, the secretion signal sequence operationally-linked to a DNA sequence encoding proteolytic tryptase having an active site mutation, the DNA sequence operationally linked to a terminator sequence, wherein the DNA sequence encoding the proteolytic tryptase having an active site mutation is a DNA sequence selected from the group consisting of SEQ. ID. NO. 20, SEQ. ID. NO. 22, SEQ. ID. NO. 24, SEQ. ID. NO. 26, SEQ. ID. NO. 36, SEQ. ID. NO. 38, SEQ. ID. NO. 40, and SEQ. ID. NO. 42.

12. A DNA expression construct comprising, in 5' to 3' order: a promoter selected from the group consisting of AOXY, GAP, MOX, FMD, ADH, LAC4, XPR12, LEU2, GAM1, PGK1, GAL7, GADPH, CYC1, and CUP1, the promoter operationally linked to a secretion signal sequence, the secretion signal sequence operationally-linked to a DNA sequence encoding proteolytic tryptase having an active site mutation, the DNA sequence operationally linked to a terminator sequence, wherein the DNA sequence encoding the proteolytic tryptase having an active site mutation encodes an amino acid sequence selected from the group consisting of SEQ. ID. NO. 21, SEQ. ID, NO. 23, SEQ. ID. NO. 25, SEQ. ID. NO. 27, SEQ. ID. NO. 37, SEQ. ID, NO. 39, SEQ. ID. NO. 41, and SEQ. ID. NO. 43.

13. The DNA expression construct according to claim 12, wherein the secretion signal sequence encodes a KEX2 cleavage site.

14. A method of producing enzymatically inactive proteolytic tryptases comprising transforming a eukaryotic host cell with an expression construct according to claim 1, wherein the mutation causes the eukaryotic host cell to express enzymatically-inactive proteolytic tryptase.

15. The method according to claim 14, wherein a yeast host cell is transformed.

16. The method according to claim 15, wherein the transformed yeast host cell is of the genus *Pichia*.

17. The method according to claim 16, wherein the transformed yeast host cell is Pichia pastoris.

18. The method according to claim 17, wherein the transformed yeast host cell has the characteristics of *Pichia pastoris* ATCC 20864 or *Pichia pastoris* strain KM71.

19. The method according to claim 14, further comprising isolating the enzymatically-inactive proteolytic tryptase produced.

20. A genetically-engineered eukaryotic cell which expresses enzymatically-inactive proteolytic tryptase wherein the eukaryotic host cell is transformed to contain and express an expression construct according to claim 1.

21. The genetically engineered eukaryotic cell of claim 20, wherein the eukaryotic cell is a yeast cell.

22. The genetically-engineered eukaryotic cell of claim 21, wherein the yeast cell is of the genus *Pichia*.

23. A DNA expression construct comprising, in 5' to 3' order: a promoter, the promoter operationally linked to a secretion signal sequence, the secretion signal sequence operationally-linked to a DNA sequence encoding proteolytic tryptase, wherein the DNA sequence comprises SEQ. ID. NO. 8, and wherein the expression construct drives the expression of mature lung tryptase that has enzymatic activity in hosts transformed to contain the expression construct.

24. A method of producing enzymatically-active lung tryptase comprising transforming a eukaryotic host cell with an expression construct according to claim 23, wherein the host cell expresses enzymatically-active lung tryptase.

25. The method according to claim 24, further comprising isolating the enzymatically-active proteolytic tryptase produced.

26. The method of claim 24, wherein a yeast host is transformed.

27. The method of claim 26, wherein the transformed yeast host is a *Pichia* host.

28. A genetically-engineered eukaryotic cell which expresses enzymatically-active lung tryptase wherein the eukaryotic host cell is transformed to contain and express an expression construct according to claim 23.

29. The genetically engineered eukaryotic cell of claim 28, wherein the eukaryotic cell is a yeast cell.

30. The genetically-engineered eukaryotic cell of claim 29, wherein the yeast cell is a *Pichia* cell.

* * * * *